US011534501B2

(12) United States Patent
Rodino-Klapac et al.

(10) Patent No.: US 11,534,501 B2
(45) Date of Patent: *Dec. 27, 2022

(54) ADENO-ASSOCIATED VIRUS VECTOR DELIVERY OF MUSCLE SPECIFIC MICRO-DYSTROPHIN TO TREAT MUSCULAR DYSTROPHY

(71) Applicant: RESEARCH INSTITUTE AT NATIONWIDE CHILDREN'S HOSPITAL, Columbus, OH (US)

(72) Inventors: Louise Rodino-Klapac, E. Groveport, OH (US); Jerry R. Mendell, Columbus, OH (US)

(73) Assignee: RESEARCH INSTITUTE AT NATIONWIDE CHILDREN'S HOSPITAL, Columbus, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/757,207

(22) PCT Filed: Mar. 16, 2018

(86) PCT No.: PCT/US2018/022853
§ 371 (c)(1),
(2) Date: Apr. 17, 2020

(87) PCT Pub. No.: WO2019/078916
PCT Pub. Date: Apr. 25, 2019

(65) Prior Publication Data
US 2021/0128749 A1  May 6, 2021

Related U.S. Application Data

(60) Provisional application No. 62/573,955, filed on Oct. 18, 2017.

(51) Int. Cl.
*C12N 15/11* (2006.01)
*A61K 48/00* (2006.01)
*A61P 21/00* (2006.01)
*C12N 15/86* (2006.01)

(52) U.S. Cl.
CPC .......... *A61K 48/0058* (2013.01); *A61P 21/00* (2018.01); *C12N 15/86* (2013.01)

(58) Field of Classification Search
None
See application file for complete search history.

(56) References Cited

U.S. PATENT DOCUMENTS

| | | |
|---|---|---|
| 5,173,414 A | 12/1992 | Lebkowski et al. |
| 5,658,776 A | 8/1997 | Flotte et al. |
| 5,786,211 A | 7/1998 | Johnson |
| 5,871,982 A | 2/1999 | Wilson et al. |
| 6,258,595 B1 | 7/2001 | Gao et al. |
| 6,310,196 B1 | 10/2001 | Ricigliano et al. |
| 6,566,118 B1 | 5/2003 | Atkinson et al. |
| 6,869,777 B2 | 3/2005 | Chamberlain et al. |
| 7,001,761 B2 | 2/2006 | Xiao |
| 7,282,199 B2 | 10/2007 | Gao et al. |
| 7,790,449 B2 | 9/2010 | Gao et al. |
| 10,166,272 B2 | 1/2019 | Dickson et al. |
| 2008/0044393 A1 | 2/2008 | White et al. |
| 2008/0249052 A1 | 10/2008 | Duan et al. |
| 2010/0003218 A1 | 1/2010 | Duan et al. |
| 2010/0184209 A1 | 7/2010 | Vermeulen et al. |
| 2014/0234255 A1 | 8/2014 | Lai et al. |
| 2014/0256802 A1 | 9/2014 | Boye et al. |
| 2015/0368647 A1 | 12/2015 | Croce et al. |
| 2016/0317680 A1 | 11/2016 | Liu et al. |
| 2017/0088837 A1 | 3/2017 | Singer et al. |
| 2018/0250423 A1 | 9/2018 | Martin |
| 2019/0117795 A1 | 4/2019 | Rodino-Klapac et al. |
| 2019/0167762 A1 | 6/2019 | Dickson et al. |

FOREIGN PATENT DOCUMENTS

| | | |
|---|---|---|
| CA | 2985000 A1 | 11/2016 |
| CO | 2019000395 A2 | 4/2019 |
| CO | 2021000227 A2 | 1/2021 |
| JP | 11-512297 A | 10/1999 |
| JP | 11-318467 A | 11/1999 |
| JP | 2010-535247 A | 11/2010 |
| JP | 2014-198728 A | 10/2014 |
| WO | 1995/13365 A1 | 5/1995 |
| WO | 1995/13392 A1 | 5/1995 |
| WO | 1996/17947 A1 | 6/1996 |
| WO | 1997/06243 A1 | 2/1997 |
| WO | 1997/08298 A1 | 3/1997 |
| WO | 1997/09441 A2 | 3/1997 |

(Continued)

OTHER PUBLICATIONS

European Application No. 17783236, European Search Report and Opinion, dated Oct. 24, 2019.
Heller et al., Alternative to gene replacement for duchenne muscular dystrophy using human alpha7 integrin (ITGA7), Doctoral dissertation abstract only, 1-2 (2014).
International Application No. PCT/US2017/027635, International Preliminary Report on Patentability, dated Oct. 16, 2018.
Kriegel et al., The miR-29 family: genomics, cell biology, and relevance to renal and cardiovascular injury, Physiological Genomics, 44:237-244 (2012).
Naso et al., Adeno-associated virus (AAV) as a vector for gene therapy, Bio. Drugs, 31:317-334 (2017).
International Application No. PCT/US17/27636, International Search Report and Written Opinion, dated Jul. 5, 2017.

(Continued)

*Primary Examiner* — Ekaterina Poliakova-Georgantas
(74) *Attorney, Agent, or Firm* — Marshall, Gerstein & Borun LLP

(57) ABSTRACT

The invention provides gene therapy vectors, such as adeno-associated virus (AAV) vectors, expressing a miniaturized human micro-dystrophin gene and method of using these vectors to express micro-dystrophin in skeletal muscle including diaphragm and cardiac muscle and to protect muscle fibers from injury, increase muscle strength and reduce and/or prevent fibrosis in subjects suffering from muscular dystrophy.

16 Claims, 23 Drawing Sheets
Specification includes a Sequence Listing.

(56) References Cited

FOREIGN PATENT DOCUMENTS

| WO | 1997/11190 A2 | 3/1997 |
|---|---|---|
| WO | 1997/21825 A1 | 6/1997 |
| WO | 1998/09657 A2 | 3/1998 |
| WO | 1999/11764 A2 | 3/1999 |
| WO | 2001/83692 A2 | 11/2001 |
| WO | 2002/06495 A2 | 1/2002 |
| WO | 2002/53703 A2 | 7/2002 |
| WO | 2008/088895 A2 | 7/2008 |
| WO | 2009/018493 A1 | 2/2009 |
| WO | 2010/071454 A1 | 6/2010 |
| WO | 2013/016352 A1 | 1/2013 |
| WO | 2013/078316 A1 | 5/2013 |
| WO | 2013/102904 A1 | 7/2013 |
| WO | 2015/107340 A1 | 7/2015 |
| WO | 2015/110449 A1 | 7/2015 |
| WO | 2015/161255 A1 | 10/2015 |
| WO | 2015/197232 A1 | 12/2015 |
| WO | 2015/197869 A1 | 12/2015 |
| WO | 2016/115543 A2 | 7/2016 |
| WO | 2016/177911 A1 | 11/2016 |
| WO | 2017/165859 A1 | 9/2017 |
| WO | 2017/181011 A1 | 10/2017 |
| WO | 2017/181014 A1 | 10/2017 |
| WO | 2017/181015 A1 | 10/2017 |
| WO | 2017/221145 A1 | 12/2017 |
| WO | 2019/245973 A1 | 12/2019 |

OTHER PUBLICATIONS

International Application No. PCT/US2018/022853, International Preliminary Report on Patentability, dated May 28, 2020.
International Application No. PCT/US2018/022853, International Search Report and Written Opinion, dated Jun. 6, 2018.
International Preliminary Report on Patentability for Corresponding International Application No. PCT/IB18/001201, dated Sep. 26, 2019.
International Preliminary Report on Patentability for Corresponding International Application No. PCT/US18/22881, dated Jan. 7, 2020.
International Preliminary Report on Patentability, PCT/US2017/027635, dated Oct. 16, 2018.
International Search Report and Written Opinion for Corresponding International Application No. PCT/IB2018/001201, dated Feb. 5, 2019.
International Search Report and Written Opinion for Corresponding International Application No. PCT/US18/22881, dated May 22, 2018.
International Search Report and Written Opinion, PCT/US2017/027635, dated Jul. 19, 2017.
Jaynes et al., Transcriptional Regulation of the Muscle Creatine Kinase Gene and Regulated Expression in Transfected Mouse Myoblasts, Mol. Cell. Biol., 6 (8): 2855-64 (1986).
Jiang et al., MicroRNAs and the regulation of fibrosis, FEBS J., 277:2015-2021 (2010).
Johnson et al., Muscle creatine kinase sequence elements regulating skeletal and cardiac muscle expression in transgenic mice, Mol. Cell. Biol., 9(8):3393-3399 (1989).
Kawecka et al., Adeno-Associated Virus (AAV) Mediated Dystrophin Gene Transfer Studies and Exon Skipping Strategies for Duchenne Muscular Dystrophy (DMD), Curr. Gene. Ther., 15(4):395-415 (2015).
Kessler et al., Gene delivery to skeletal muscle results in sustained expression and systemic delivery of a therapeutic protein, Proc. Nat. Acad. Sc. U.S.A., 93:14082-14087 (1996).
Kim et al., microRNA-directed cleavage of ATHB15 mRNA regulates vascular development in *Arabidopsis inflorescence* stems, Plant J., 42:84-94 (2005).
Koo et al., Long-term functional adeno-associated virus-microdystrophin expression in the dystrophic CXMDj dog, J. Gene. Med., 13(9):497-506 (2011).

Laughlin et al., Cloning of infectious adeno-associated virus genomes in bacterial plasmids, Gene., 23(1):65-73 (1983).
Lebkowski et al., Adena-associated vims: a vector system for efficient introduction and integration of DNA into a variety of mammalian cell types, Mol. Cell. Biol., 7:3988-96 (1988).
Lederfein et al., Kilodalton Protein is a Major Product of the Duchenne Muscular Dystrophy Gene in Brain and Other Nonmuscle Tissues, Proc. Natl. Acad. Sci. USA., 89(12):5346-5350 (1992).
Lewis et al., Generation of neutralizing activity against human immunodeficiency vims type 1 in serum by antibody gene transfer, J. Virol., 76:8769-8775 (2002).
Liu et al., Adeno-associated Virus-Mediated Microdystrophin Expression Protects Young MDX Muscle From Contraction-Induced Injury, Mol. Ther., 11:245-256 (2005).
Love et al., An autosomal transcript in skeletal muscle with homology to dystrophin, Nature, 339:55-58 (1989).
Mader et al., A steroid-inducible promoter for the controlled overexpression of cloned genes in eukaryotic cells, Proc. Natl. Acad. Sci. U.S.A., 90(12):5603-5607 (1993).
Marsic et al., Vector Design Tour De Force: Integrating Combinatorial and Rational Approaches to Derive Novel Adeno-Associated Virus Variants, Molecular Therapy, 22:1900-1909 (2014).
Martin et al., Translational Studies of GLAGT2 Gene Therapy for Duchenne Muscular Dystrophy, https://apps.dtic.mil/dtic/tr/fulltext/u2a613577.pdf (2018).
McLaughlin et al., Adeno-associated virus general transduction vectors: analysis of proviral structures, J. Virol., 62(6):1963-73 (1988).
Meadows et al., Reducing skeletal muscle fibrosis with AAV-Oelivered miR-29 (P04.089), Neurology. 78:1-2 (2012).
Mendell et al., A phase 1/2a follistatin gene therapy trial for becker muscular dystrophy, Molecular therapy : the journal of the American Society of Gene Therapy, 23:192-201 (2015).
Mendell et al., Evidence-based path to newborn screening for Ouchenne muscular dystrophy, Ann. Neural. 71:304-13 (2012).
Mendell et al., Limb-girdle muscular dystrophy type 2D gene therapy restores alpha-sarcoglycan and associated proteins., Ann. Neurol., 66(3):290-297 (2009).
Mendell et al., Sustained alpha-sarcoglycan gene expression after gene transfer in limb-girdle muscular dystrophy, type 2D. Ann. Neurol. 68:629-638 (2010).
Mori et al., Two Novel Adeno-Associated Viruses From Cynomolgus Monkey: Pseudotyping Characterization of Capsid Protein, Virology, 330:375-383 (2004).
Mulieri et al., Protection of human left ventricular myocardium from cutting injury with 2,3-butanedione monoxime, Circ. Res., 65(5):1441-1449 (1989).
Murphy et al., Long-term correction of obesity and diabetes in genetically obese mice by a single intramuscular injection of recombinant adeno-associated virus encoding mouse leptin, Proc. Natl. Acad. Sci. U.S.A., 94:13921-13926 (1997).
Muscat et al., Multiple 5'-flanking regions of the human alpha-skeletal actin gene synergistically modulate muscle-specific expression, Mol. Cell Biol., 7(11):4089-4099 (1987).
Muzyczka, Use of Adeno-Associated Virus as a General Transduction Vector for Mammalian Cells, Current Topics in Microbiology and Immunology, 158:97-129 (1992).
Nevo et al., The Ras antagonist, famesylthiosalicylic acid (FTS), decreases fibrosis and improves muscle strength in dy/dy mouse model of muscular dystrophy, PloS One, 6(3):e18049 (2011).
Paul et al., Increased viral titer through concentration of viral harvests from retroviral packaging lines, Human Gene Therapy, 4(5):609-615 (1993).
Perrin et al., An experimental rabies vaccine produced with a new BHK-21 suspension cell culture process: use of serum-free medium and perfusion-reactor system, Vaccine, 13(13):1244-1250 (1995).
Pozsgai et al., Systemic AAV-mediated (Beta)-sarcoglycan delivery targeting cardiac and Skeletal muscle ameliorates histological and functional deficits in LGMD2E mice, Mol. Ther., 25(4):855-869 (2017).
Rafael et al., Skeletal muscle-specific expression of a utrophin transgene rescues utrophin-dystrophin deficient mice, Nat. Genet., 19:79-82 (1998).

(56) References Cited

OTHER PUBLICATIONS

Roderburg et al., Micro-RNA profiling reveals a role for miR-29 in human and murine liver fibrosis, Hepatology. 53:209-18 (2011).
Rodino-Klapac et al., A translational approach for limb vascular delivery of the micro-dystrophin gene without high volume or high pressure for treatment of Duchenne muscular dystrophy, J. Transl. Med., 5:45 (2007).
Rodino-Klapac et al., Micro-dystrophin and follistatin co-delivery restores muscle function in aged DMD model, Hum. Mol. Gen., 22:4929-4937 (2013).
Rodino-Klapac et al., Persistent expression of FLAG-tagged micro dystrophin in nonhuman primates following intramuscular and vascular delivery, Molecular therapy : the journal of the American Society of Gene Therapy, 18:109-117 (2010).
Rooij et al., Dysregulation of microRNAs after myocardial infarction reveals a role of miR-29 in cardiac fibrosis, Proc. Natl. Acad. Sci. USA. 105:13027-32 (2008).
Ruffing et al., Mutations in the carboxy terminus of adeno-associated virus 2 capsid proteins affect viral infectivity: Lack of an RGD integrin-binding motif, J. Gen. Virol., 75:3385-3392 (1994).
Sacco et al., Short telomeres and stem cell exhaustion model Duchenne muscular dystrophy in mdx/mTR mice, Cell., 143:1059-1071 (2010).
Salva et al. Design of tissue-specific regulatory cassettes for high-level rAAV-mediated expression in skeletal and cardiac muscle, Mol. Ther., 15(2):320-329 (2007).
Sambrook et al., Molecular cloning: A laboratory manual, 2nd Ed., Cold Spring Harbor Laboratory (1989).
Samulski et al., A Recombinant Plasmid From Which an Infectious Adeno-Associated Virus Genome Can Be Excised in Vitro and Its Use to Study Viral Replication, J. Virol., 61:3096-3101 (1987).
Samulski et al., Cloning of adeno-associated virus into pBR322: rescue of intact virus from the recombinant plasmid in human cells, Proc. Natl. Acad. Sci. U.S.A., 79(6):2077-2081 (1982).
Samulski et al., Helper-free stocks of recombinant adeno-associated viruses: normal integration does not require viral gene expression, J. Virol., 63(9):3822-3828 (1989).
Schnepp et al., Highly purified recombinant adeno-associated virus vectors. Preparation and quantitation, Methods Mol. Med., 69:427-443 (2002).
Semenza et al., Hypoxia-inducible nuclear factors bind to an enhancer element located 3' to the human erythropoietin gene, Proc. Natl. Acad. Sci. U.S.A., 88(13):5680-5684 (1991).
Senapathy et al., Molecular cloning of adeno-associated virus variant genomes and generation of infectious virus by recombination in mammalian cells, J. Biol. Chem., 259:4661-4666 (1984).
Sicinski et al., The molecular basis of muscular dystrophy in the mdx mouse: a point mutation, Science, 30:244(4912):1578-80 (1989).
Sondergaard et al., AAV.Dysferlin Overlap Vectors Restore Function in Dysferlinopathy Animal Models, Annals of Clinical and Translational Neurology, 2:256-270 (2015).
Squire et al., Prevention of pathology in mdx mice by expression of utrophin: analysis using an inducible transgenic expression system, Hum. Mol. Genet., 11(26):3333-3344 (2002).
Srivastava et al., Nucleotide Sequence and Organization of the Adeno-Associated Virus 2 Genome, J. Virol., 45:555-564 (1983).
Stedman et al., The mdx mouse diaphragm reproduces the degenerative changes of duchenne muscular dystrophy, Nature, 352:536-539 (1991).
Straub et al., Muscular dystrophies and the dystrophinglycoprotein complex, Curr. Opin. Neurol., 10:168-175 (1997).
Tinsley et al., Expression of full-length utrophin prevents muscular dystrophy in mdx mice, Nat. Med., 4(2):1441-1444 (1998).
Tinsley et al., Primary structure of dystrophin-related protein, Nature, 360:591-593 (1992).
Tratschin et al., A human parvovirus, adeno-associated virus, as a eucaryotic vector: transient expression and encapsidation of the procaryotic gene for chloramphenicol acetyltransferase, Mol. Cell. Biol., 4(10):2072-2081 (1984).

Tratschin et al., Adeno-associated virus vector for high-frequency integration, expression, and rescue of genes in mammalian cells, Mol. Cell. Biol., 5(11):3251-3260 (1985).
Wallace et al., Mechanisms of muscle degeneration, regeneration, and repair in the muscular dystrophies, Annu. Rev. Physiol., 71:37-57 (2009).
Weintraub et al., The myoD gene family: nodal point during specification of the muscle cell lineage, Science, 251:761-766 (1991).
Xiao et al., Efficient long-term gene transfer in to muscle tissue of immunocompetent mice by adeno-associated virus vector, J. Virol., 70:8098-8108 (1996).
Xiao et al., Production of high-titer recombinant adeno-associated virus vectors in the absence of helper adenovirus, J. Virol., 12:2224-2232 (1998).
Zhou et al., Haploinsufficiency of utrophin gene worsens skeletal muscle inflammation and fibrosis in mdx mice, J. Neurol. Sci., 264:106-111 (2008).
Zhou et al., Targeting fibrosis in duchenne muscular dystrophy, J. Neuropathol. Exp. Neurol., 69(8):771-776 (2010).
Ambros, MicroRNA pathways in flies and worms: growth, death, fat, stress, and timing, Cell., 113:673-6 (2003).
Anderson et al., Nucleic acid hybridisation: A practical approach, Ch. 4, IRL Press Limited (Oxford, England).
Bulfield et al., X chromosome-linked muscular dystrophy (mdx) in the mouse, Proc. Natl. Acad. Sci. USA., 81(4):1189-1192 (1984).
Cacchiarelli et al., MicroRNAs involved in molecular circuitries relevant for the Duchenne muscular dystrophy pathogenesis are controlled by the dystrophin/nNOS pathway, Cell Metab., 12:341-51 (2010).
Carnwath et al., Muscular dystrophy in the mdx mouse: histopathology of the soleus and extensor digitorum longus muscles, J. Neural. Sci., 80:39-54 (1987).
Carter, Adeno-associated virus vectors, Current Opinions in Biotechnology, 3(5):533-539 (1992).
Chao et al., Several log increase in therapeutic transgene delivery by distinct adeno-associated viral serotype vectors, Mol. Ther., 2:619-623 (2000).
Chao et al., Sustained and complete phenotype correction of hemophilia b mice following intramuscular injection of aav1 serotype vectors, Mol. Ther., 4:217-222 (2001).
Chicoine et al., Plasmapheresis Eliminates the Negative Impact of AAV Antibodies on Microdystrophin Gene Expression Following Vascular Delivery, Mol Ther., 22(2): 338-347 (2014).
Clark et al., A Stable Cell Line Carrying Adenovirus-Inducible Rep and Cap Genes Allows for Infectivity Titration of Adeno-Associated Virus Vectors, Gene Therapy, 3:1124-1132 (1996).
Clark et al., Highly purified recombinant adeno-associated virus vectors are biologically active and free of detectable helper and wild-type viruses, Hum. Gene. Ther., 10(6):1031-1039 (1999).
Clark et al., Recombinant adeno-associated viral vectors mediate long-term transgene expression in muscle, Hum. Gene. Ther., 8:659-669 (1997).
Coulton et al., The mdx mouse skeletal muscle myopathy: I. A histological, morphometric and biochemical investigation, Neuropathol. Appl. Neurobiol., 14:53-70 (1988).
Cserjesi et al., Myogenin induces the myocyte-specific enhancer binding factor MEF-2 independently of other muscle-specific gene products, Mol. Cell. Biol., 11(10):4854-4862 (1991).
Cullen et al., Ultrastructure of the skeletal muscle in the X chromosome-linked dystrophic (mdx) mouse, Comparison with duchenne muscular dystrophy, Acta. Neuropathol., 77:69-81 (1988).
Cushing et al., miR-29 is a major regulator of genes associated with pulmonary fibrosis, Am. J. Respir. Cell. Mol. Biol. 45:287-94 (2011).
De et al., High levels of persistent expression of alpha1-antitrypsin mediated by the nonhuman primate serotype rh.10 adeno-associated virus despite preexisting immunity to common human adeno-associated viruses, Mol. Ther., 13(1):67-76 (2006).
Deconinck et al., Utrophin-dystrophin-deficient mice as a model for Duchenne muscular dystrophy, Cell., 90:717-727 (1997).

(56) References Cited

OTHER PUBLICATIONS

Desguerre et al. Endomysial fibrosis in Duchenne muscular dystrophy: a marker of poor outcome associated with macrophage alternative activation, J. Neuropathol. Exp. Neural., 68:762-773 (2009).
Diprimio et al., Adena-associated virus for the treatment of muscle diseases: toward clinical trials, Curr. Opin. Mol. Ther., 12:553-560 (2010).
Dupont-Versteegden et al., Differential expression of muscular dystrophy in diaphragm versus hindlimb muscles of mdx mice, Muscle Nerve., 15:1105-1110 (1992).
Eisenberg et al. Distinctive Patterns of microRNA Expression in Primary Muscular Disorders, Proc. Natl. Acad. Sci. USA., 104:17016-21 (2007).
Extended European Search Report, Application No. 17783236.7 dated Oct. 24, 2019.
Flotte et al., Gene Expression from Adeno-associated Virus Vectors in Airway Epithelial Cells, Am. J. Respir. Cell Mol. Biol., 7:349-356 (1992).
Foster et al., Codon and mRNA sequence optimization of microdystrophin transgenes improves expression and physiological outcome in dystrophic mdx mice following AAV2/8 gene transfer, Mol. Ther., 16(11):1825-1832 (2008).
Franz et al., Association of nonsense mutation of dystrophin gene with disruption of sarcoglycan complex in X-linked dilated cardiomyopathy, Lanc., 355(9217):1781-1785 (2000).
Gao et al., Clades of Adeno-associated viruses are widely disseminated in human tissues, J. Virol., 78:6381-6388 (2004).
Genbank Accession No. AF085716, Adena-associated virus 5 DNA binding trs helicase (Rep22) and capsid protein (VP1) aenes, complete eds (1999).
GenBank Accession No. AX753246, Version AX753246, Sequence 1 from Patent EP1310571, located at < https://www.ncbi.nlm.nih.gov/nuccore/AX753246 > (2003).
Genbank Accession No. AX753249, Sequence 4 from Patent EP1310571 (2003).
Genbank Accession No. NC_001729, Adena-associated virus-3, complete genome (2018).
GenBank Accession No. NC_001829, Version NC_001829, Adeno-associated virus-4, complete genome, located at < https://www.ncbi.nlm.nih.gov/nuccore/NC_001829 > (2018).
GenBank Accession No. NC_001862, Version NC_001862, Adeno-associated virus 6, complete genome, located at < https://www.ncbi.nlm.nih.gov/nuccore/NC_001862.1?report=genbank > (2004).
GenBank Accession No. NC_002077, Version NC_002077, Adeno-associated virus-1, complete genome, located at < https://www.ncbi.nlm.nih.gov/nuccore/NC_002077 > (2018).
Grady et al., Skeletal and cardiac myopathies in mice lacking utrophin and dystrophin: a model for Duchenne muscular dystrophy, Cell., 90:729-738 (1997).
Grose et al., Homologous recombination mediates functional recovery of dysferlin deficiency following AA VS gene transfer, PloS One, 7(6):e39233 (2012).
Guan et al., Gene therapy in monogenic congenital myopathies, Methods, 99:91-8 (2015).
Gutpell et al., Skeletal muscle fibrosis in the mdx/utm+/− Mouse validates Its suitability as a murine model of duchenne muscular dystrophy, PloS One, 10:e0117306 (2015).
Hakim et al., Monitoring murine skeletal muscle function for muscle gene therapy, Methods. Mol. Biol. 709:75-89 (2011).
Harper et al., Modular flexibility of dystrophin: implications for gene therapy of Duchenne muscular dystrophy, Nature Medicine, 8(3):253-261 (2002).
Hayashita-Kinoh et al., Intra-Amniotic rAAV-Mediated Microdystrophin Gene Transfer Improves Canine X-Linked Muscular Dystrophy and May Induce Immune Tolerance, Mol. Ther., 23(4):627-637 (2015).
Heller et al., MicroRNA-29 and Micro-Dystrophin Combinatorial Therapy Suppresses Fibrosis and Restores Function to mdx/utm+/− Mice, Mol. Ther., 24(1): S151 (2016).
Hermonat et al., Use of adeno-associated vims as a mammalian DNA cloning vector: transduction of neomycin resistance into mammalian tissue culture cells, Proc. Natl. Acad. Sci. U.S.A., 81(20):6466-6470 (1984).
Herzog et al., Stable gene transfer and expression of human blood coagulation factor IX after intramuscular injection of recombinant adeno-associated virus, Proc. Natl. Acad. Sci. U.S.A., 94(11):5804-5809 (1997).
Hoffman et al., Dystrophin: the protein product of the duchenne muscular dystrophy locus, Cell., 51:919-928 (1987).
International Application No. PCT/US19/037489, International Search Report and Written Opinion, dated Sep. 6, 2019.
International Application No. PCT/US19/37489, International Preliminary Report on Patentability, dated Dec. 30, 2020.
International Application No. PCT/US17/27630, International Preliminary Report on Patentability, dated Oct. 25, 2018.
International Application No. PCT/US17/27630, International Search Report and Written Opinion, dated Jul. 14, 2017.
International Application No. PCT/US17/27636, International Preliminary Report on Patentability, dated Oct. 25, 2018.
Clemens et al., Recombinant truncated dystrophin minigenes: construction, expression, and adenoviral delivery, Hum. Gene Ther., 6:1477-1485 (1995).
Dong et al., Quantitative analysis of the packaging capacity of recombinant adeno-associated virus, Human Gene Therapy, 7:2101-2112 (1996).
Douglas Ingram, JP Morgan 39th Annual Healthcare Conference, Jan. 11, 2021.
Hartigan-O'Connor et al., Progress toward gene therapy of duchenne muscular dystrophy, Seminars in Neurology, 19(3):323-332 (1999).
Hauser et al., Functional analysis of truncated dystrophin minigenes in the muscles of mdx mice, Abstract 2081, The American Journal of Human Genetics, S61(4) (1997).
Heller et al., 379. Mi croRNA-29 and Micro-Dystrophin Combinatorial Therapy Suppresses Fibrosis and Restores Function to mdx/utm+/− Mice, Mol. Ther., 24(1): S151 (2016).
Martin, Translational Studies of GALGT2 Gene Therapy for Duchenne Muscular Dystrophy, Annual Report, Approved for Public Release Distribution Unlimited The Research Institute at Nationwide Children's Hospital Columbus (2013).
Mauro et al., A critical analysis of codon optimization in human therapeutics, Trends in Molecular Medicine, 20(11):604-13 (2014).
Mendell et al, A randomized, double blind, placebo-controlled, gene-delivery clinical trial of rAAVrh74.MHCK7.micro-dystrophin for Duchenne muscular dystrophy; ASGCT Virtual Annual Meeting (2021).
Phelps et al., Expression of full-length and truncated dystrophin mini-genes in transgenic mdx mice, Human Molecular Genetics, 4(8):1251-1258 (1995).
Recan et al., Are cysteine-rich and COOH-terminal domains of dystrophin critical for sarcolemmal localization?, J. Clin. Invest., 89:712-716 (1992).
Rodino-Klapac et al., Development of AAVrh74 Micro-dystrophin gene transfer therapy for duchenne, Muscular dystrophy association (MDA) Virtual Clinical and Scientific Conference (2021).
Sakamoto et al., Micro-dystrophin cDNA ameliorates dystrophic phenotypes when introduced into mdx mice as a transgene, Biochem. and Biophysical Research Comm., 293:1265-1272 (2002).
Wang et al., Adena-associated virus vector carrying human minidystrophin genes effectively ameliorates muscular dystrophy in mdx mouse model, PNAS, 97:13714-13719 (2000).
Wells et al., Expression of human full-length and minidystrophin in transgenic rndx mice: implications for gene therapy of duchenne muscular dystrophy, Hum. Mol. Gene., 4(8):1245-2250 (1995).
Yuasa et al., Effective restoration of dystrophin-associated proteins in vivo by adenovirus-mediated transfer of truncated dystrophin cDNAs, FEBS Letters, 425:329-336 (1998).
Gupta et al., Codon optimization, Project Report, 1-11 (2003).
Heller et al., MicroRNA-29 overexpression by adeno-associated virus suppresses fibrosis and restores muscle function in combination with micro-dystrophin, JCI Insight., 2(9): 1-13 (2017).

FIG. 3
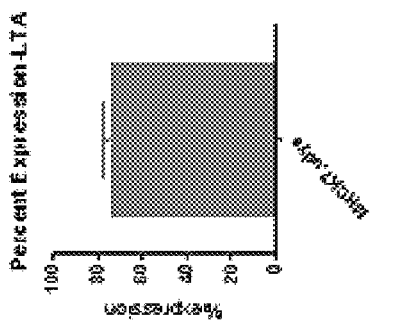
FIG. 3A
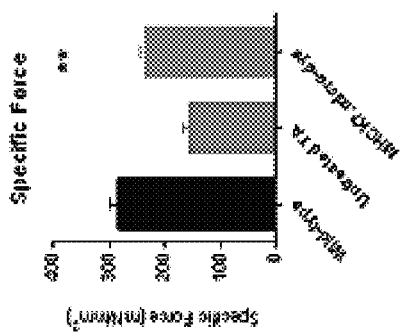
FIG. 3B
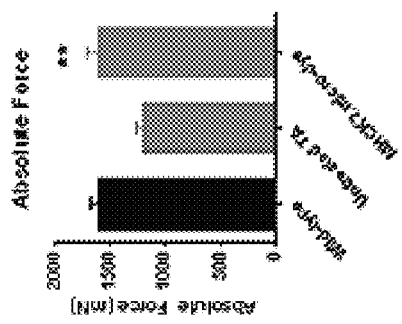
FIG. 3C

FIG. 10

SEQ ID NO: 3 rAAVrh74.MHCK7.micro-dystrophin

Main features:
MHCK7 promoter
Chimeric intron sequence
Human micro-dystrophin sequence
Poly A tail
Ampicillin resistance
pGEX plasmid backbone with pBR322 origin of replication GCCCAATACGCAAACCGCCTCTCCCCGCGCGTTGGCCGATTCATTAATGCAGCTGGCGCGCTCGCTCGCTCACTGA
GGCCGCCCGGGCAAAGCCCGGGCGTCGGGCGACCTTTGGTCGCCCGGCCTCAGTGAGCGAGCGAGCGCGCAGA
GAGGGAGTGGCCAACTCCATCACTAGGGGTTCCTTGTAGTTAATGATTAACCCGCCATGCTAATTATCTACGTAGC
CATGTCTAGAgtttaaacaagcttgcatgtctaagctagacccttcagattaaaaataactgaggtaagggcctggtagggagtggtgtgag
acgctcctgtctctcctctatctgcccatcggcccttggggaggaggaatgtgcccaaggactaaaaaaggccatggagccagaggggcgagggc
aacagaccttcatgggcaaaccttggggccctgctgtctagcatgccccactacgggtctaggctgcccatgtaaggaggcaaggcctggggacacc
cgagatgcctggttataattaacccagacatgtggctgccccccccccccaacacctgctgcctctaaaaataaccctgtccctggtggatccctgca
tgcgaagatcttcgaacaaggctgtgggggactgagggcaggctgtaacaggcttgggggccagggcttatacgtgcctgggactcccaaagtatta
ctgttccatgttcccggcgaagggccagctgtccccgccagctagactcagcacttagtttaggaaccagtgagcaagtcagcccttggggcagccc
atacaaggccatggggctgggcaagctgcacgcctgggtccggggtgggcacggtgcccggggcaacgagctgaaagctcatctgctctcagggcc
ctccctggggacagcccctcctggctagtcacaccctgtaggctcctctatataacccaggggcacaggggctgccctcattctaccaccacctccaca
gcacagacagacactcaggagccagccagcggcgcgcccAGGTAAGTTTAGTCTTTTTGTCTTTTATTTCAGGTCCCGGATCCGG
TGGTGGTGCAAATCAAAGAACTGCTCCTCAGTGGATGTTGCCTTTACTTCTAGGCCTGTACGGAAGTGTTACTTCT
GCTCTAAAAGCTGCGGAATTGTACCCGCGGCCGCCACCATGCTGTGGTGGGAGGAGGTGGAGGATTGTTATGAA
AGGGAGGACGTGCAGAAGAAGACTTTTACCAAGTGGGTGAACGCTCAGTTCAGCAAATTTGGGAAGCAGCACA
TCGAGAATCTGTTTTCCGACCTGCAGGATGGGAGACGGCTGCTGGATCTGCTGGAAGGACTGACTGGCCAGAA
GCTGCCCAAAGAGAAGGGGAGCACTAGGGTGCACGCCCTGAACAACGTGAACAAAGCTCTGAGAGTGCTGCA
GAACAACAACGTGGATCTGGTGAATATTGGCAGTACTGATATCGTGGACGGGAACCACAAACTGACACTGGGC
CTGATCTGGAACATTATTCTGCACTGGCAGGTGAAAAATGTGATGAAGAACATCATGGCCGGGCTGCAGCAGA
CCAATTCCGAGAAGATCCTGCTGTCTTGGGTGCGGCAGAGCACCCGCAACTATCCCCAGGTGAACGTGATTAAC
TTCACTACATCCTGGAGCGACGGGCTGGCCCTGAATGCTCTGATTCACAGCCACAGGCCTGATCTGTTCGACTGG
AATAGCGTGGTGTGCCAGCAGTCTGCCACACAGCGCCTGGAACATGCCTTCAATATCGCTCGGTACCAGCTGGG
GATCGAAAAACTGCTGGACCCAGAGGATGTGGACACTACATACCCAGATAAAAAGTCTATTCTGATGTACATTA
CTAGCCTGTTCCAGGTGCTGCCACAGCAGGTGTCTATTGAAGCCATTCAGGAGGTGGAAATGCTGCCCCGCCCCC
CCAAAGTGACTAAAGAGGAGCATTTTCAGCTGCATCATCAGATGCATTACAGCCAGCAGATTACCGTGAGCCTG
GCTCAGGGATATGAGCGCACCAGTAGTCCAAAACCACGGTTCAAGTCCTACGCTTATACCCAGGCTGCCTACGT
GACAACTAGCGACCCTACTAGATCCCCCTTTCCATCCCAGCACCTGGAGGCCCCAGAGGACAAGAGCTTTGGGTC
CAGCCTGATGGAAAGCGAGGTGAATCTGGATCGGTACCAGACAGCCCTGGAGGAGGTGCTGAGCTGGCTGCTG

FIG. 10 (cont.)

AGTGCTGAAGACACACTGCAGGCCCAGGGCGAAATTTCCAATGACGTGGAAGTGGTGAAGGATCAGTTCCACA
CACACGAGGGCTATATGATGGACCTGACAGCTCACCAGGGGCGCGTGGGCAATATCCTGCAGCTGGGCTCTAA
ACTGATCGGCACCGGGAAACTGAGTGAGGACGAGGAAACAGAAGTGCAGGAGCAGATGAACCTGCTGAACAG
CCGCTGGGAGTGTCTGAGAGTGGCTAGTATGGAGAAGCAGTCCAACCTGCACCGGGTGCTGATGGACCTGCAG
AACCAGAAACTGAAAGAGCTGAACGACTGGCTGACAAAGACTGAGGAACGCACAAGGAAGATGGAGGAGGA
GCCACTGGGACCCGACCTGGAGGATCTGAAGAGACAGGTGCAGCAGCATAAGGTGCTGCAGGAGGATCTGGA
ACAGGAGCAGGTGCGGGTGAACTCCCTGACACATATGGTGGTGGTGGTGGACGAATCTAGTGGAGATCACGCC
ACCGCCGCCCTGGAGGAACAGCTGAAGGTGCTGGGGGACCGGTGGGCCAACATTTGCCGGTGGACCGAGGAC
AGGTGGGTGCTGCTGCAGGACATCCTGCTGAAATGGCAGAGGCTGACCGAGGAGCAGTGTCTGTTTAGTGCTT
GGCTGAGCGAGAAAGAGGACGCCGTGAACAAGATCCACACAACCGGCTTTAAGGATCAGAACGAAATGCTGTC
TAGCCTGCAGAAACTGGCTGTGCTGAAGGCCGATCTGGAGAAAAAGAAGCAGAGCATGGGCAAACTGTATAG
CCTGAAACAGGACCTGCTGAGCACCCTGAAGAACAAGAGCGTGACCCAGAAGACAGAAGCCTGGCTGGATAAC
TTTGCCCGCTGCTGGGACAACCTGGTGCAGAAACTGGAGAAAAGTACAGCTCAGATCTCTCAGGCTGTGACCAC
AACCCAGCCTAGCCTGACCCAGACAACCGTGATGGAAACCGTGACCACCGTGACAACCCGCGAACAGATCCTGG
TGAAACATGCCCAGGAAGAGCTGCCACCTCCACCTCCCCAGAAGAAGAGAACCCTGGAGCGGCTGCAGGAGCT
GCAGGAAGCCACTGACGAACTGGACCTGAAGCTGAGGCAGGCCGAAGTGATTAAGGGGTCTTGGCAGCCTGTG
GGCGATCTGCTGATTGATTCCCTGCAGGACCACCTGGAAAAGGTGAAGGCTCTGAGAGGCGAAATTGCTCCACT
GAAGGAGAACGTGAGTCATGTGAACGATCTGGCTAGACAGCTGACAACACTGGGCATCCAGCTGAGCCCATAC
AATCTGAGCACACTGGAGGACCTGAATACCAGGTGGAAGCTGCTGCAGGTGGCTGTGGAAGACGGGTGCGG
CAGCTGCATGAGGCCCATCGCGACTTCGGACCAGCCAGCCAGCACTTTCTGAGCACATCCGTGCAGGGGCCCTG
GGAGAGGGCCATTTCTCCCAACAAGGTGCCCTACTATATTAATCACGAGACCCAGACCACTTGTTGGGACCATCC
CAAGATGACAGAACTGTACCAGTCCCTGGCCGATCTGAACAACGTGAGGTTTAGCGCTTACAGAACCGCTATGA
AGCTGAGACGGCTGCAGAAGGCCCTGTGCCTGGATCTGCTGTCCCTGTCCGCCGCCTGCGATGCCCTGGATCAGC
ATAATCTGAAGCAGAACGATCAGCCAATGGATATCCTGCAGATCATCAACTGCCTGACCACTATCTACGACAGG
CTGGAGCAGGAGCACAACAACCTGGTGAACGTGCCTCTGTGCGTGGATATGTGCCTGAACTGGCTGCTGAACGT
GTATGACACTGGGCGCACCGGCCGGATCAGAGTGCTGAGTTTTAAAACTGGGATTATCTCCCTGTGTAAGGCCC
ACCTGGAGGACAAGTACAGGTACCTGTTCAAGCAGGTGGCTAGTAGCACTGGATTTTGTGACCAGCGCCGCCTG
GGACTGCTGCTGCATGATAGTATCCAGATTCCTAGACAGCTGGGAGAGGTGGCTAGTTTCGGAGGATCTAACAT
CGAACCCAGCGTGCGCAGCTGTTTCCAGTTTGCCAATAACAAACCTGAAATCGAGGCTGCTCTGTTCCTGGATTG
GATGCGCCTGGAACCACAGAGCATGGTGTGGCTGCCTGTGCTGCACAGAGTGGCTGCCGCCGAAACTGCCAAG
CACCAGGCTAAATGCAACATCTGCAAGGAATGTCCCATTATCGGCTTTCGCTACAGGAGTCTGAAACATTTTAAC
TACGATATTTGCCAGAGCTGCTTCTTTTCCGGAAGAGTGGCCAAAGGACACAAGATGCACTACCCTATGGTGGA
ATATTGCACCCCAACTACATCTGGCGAAGATGTGCGCGATTTTGCCAAGGTGCTGAAGAATAAGTTTCGGACTA
AGAGGTACTTCGCCAAGCACCCCCGCATGGGGTATCTGCCAGTGCAGACAGTGCTGGAAGGAGACAATATGGA
GACCGATACAATGTGAGCGGCCGCAATAAAAGATCTTTATTTTCATTAGATCTGTGTGTTGGTTTTTTGTGTGTCTA
GAGCATGGCTACGTAGATAAGTAGCATGGCGGGTTAATCATTAACTACAAGGAACCCCTAGTGATGGAGTTGGCC
ACTCCCTCTCTGCGCGCTCGCTCGCTCACTGAGGCCGGGCGACCAAAGGTCGCCCGACGCCCGGGCTTTGCCCGG
GCGGCCTCAGTGAGCGAGCGAGCGCGCCAGCTGGCGTAATAGCGAAGAGGCCCGCACCGATCGCCCTTCCCAAC
AGTTGCGCAGCCTGAATGGCGAATGGAAGTTCCAGACGATTGAGCGTCAAAATGTAGGTATTTCCATGAGCGTTT
TTCCTGTTGCAATGGCTGGCGGTAATATTGTTCTGGATATTACCAGCAAGGCCGATAGTTTGAGTTCTTCTACTCAG
GCAAGTGATGTTATTACTAATCAAAGAAGTATTGCGACAACGGTTAATTTGCGTGATGGACAGACTCTTTTACTCG
GTGGCCTCACTGATTATAAAAACACTTCTCAGGATTCTGGCGTACCGTTCCTGTCTAAAATCCCTTTAATCGGCCTC

FIG. 10 (continued)

CTGTTTAGCTCCCGCTCTGATTCTAACGAGGAAAGCACGTTATACGTGCTCGTCAAAGCAACCATAGTACGCGCCC
TGTAGCGGCGCATTAAGCGCGGCGGGTGTGGTGGTTACGCGCAGCGTGACCGCTACACTTGCCAGCGCCCTAGC
GCCCGCTCCTTTCGCTTTCTTCCCTTCCTTTCTCGCCACGTTCGCCGGCTTTCCCCGTCAAGCTCTAAATCGGGGGCT
CCCTTTAGGGTTCCGATTTAGTGATTTACGGCACCTCGACCCCAAAAAACTTGATTAGGGTGATGGTTCACGTAGT
GGGCCATCGCCCTGATAGACGGTTTTTCGCCCTTTGACGTTGGAGTCCACGTTCTTTAATAGTGGACTCTTGTTCCA
AACTGGAACAACACTCAACCCTATCTCGGTCTATTCTTTTGATTTATAAGGGATTTTGCCGATTTCGGCCTATTGGTT
AAAAAATGAGCTGATTTAACAAAAATTTAACGCGAATTTTAACAAAATATTAACGTTTACAATTTAAATATTTGCTT
ATACAATCTTCCTGTTTTTGGGGCTTTTCTGATTATCAACCGGGGTACATATGATTGACATGCTAGTTTTACGATTAC
CGTTCATCGATTCTCTTGTTTGCTCCAGACTCTCAGGCAATGACCTGATAGCCTTTGTAGAGACCTCTCAAAAATAG
CTACCCTCTCCGGCATGAATTTATCAGCTAGAACGGTTGAATATCATATTGATGGTGATTTGACTGTCTCCGGCCTT
TCTCACCCGTTTGAATCTTTACCTACACATTACTCAGGCATTGCATTTAAAATATATGAGGGTTCTAAAAATTTTTAT
CCTTGCGTTGAAATAAAGGCTTCTCCCGCAAAAGTATTACAGGGTCATAATGTTTTTGGTACAACCGATTTAGCTTT
ATGCTCTGAGGCTTTATTGCTTAATTTTGCTAATTCTTTGCCTTGCCTGTATGATTTATTGGATGTTGGAAGTTCCTG
ATGCGGTATTTTCTCCTTACGCATCTGTGCGGTATTTCACACCGCATATGGTGCACTCTCAGTACAATCTGCTCTGAT
GCCGCATAGTTAAGCCAGCCCCGACACCCGCCAACACCCGCTGACGCGCCCTGACGGGCTTGTCTGCTCCCGGCAT
CCGCTTACAGACAAGCTGTGACCGTCTCCGGGAGCTGCATGTGTCAGAGGTTTTCACCGTCATCACCGAAACGCGC
GAGACGAAAGGGCCTCGTGATACGCCTATTTTTATAGGTTAATGTCATGATAATAATGGTTTCTTAGACGTCAGGT
GGCACTTTTCGGGGAAATGTGCGCGGAACCCCTATTTGTTTATTTTTCTAAATACATTCAAATATGTATCCGCTCAT
GAGACAATAACCCTGATAAATGCTTCAATAATATTGAAAAAGGAAGAG<u>TATGAGTATTCAACATTTCCGTGTCGCC</u>
<u>CTTATTCCCTTTTTTGCGGCATTTTGCCTTCCTGTTTTTGCTCACCCAGAAACGCTGGTGAAAGTAAAAGATGCTGAA</u>
<u>GATCAGTTGGGTGCACGAGTGGGTTACATCGAACTGGATCTCAACAGCGGTAAGATCCTTGAGAGTTTTCGCCCC</u>
<u>GAAGAACGTTTTCCAATGATGAGCACTTTTAAAGTTCTGCTATGTGGCGCGGTATTATCCCGTATTGACGCCGGGC</u>
<u>AAGAGCAACTCGGTCGCCGCATACACTATTCTCAGAATGACTTGGTTGAGTACTCACCAGTCACAGAAAAGCATCT</u>
<u>TACGGATGGCATGACAGTAAGAGAATTATGCAGTGCTGCCATAACCATGAGTGATAACACTGCGGCCAACTTACTT</u>
<u>CTGACAACGATCGGAGGACCGAAGGAGCTAACCGCTTTTTTGCACAACATGGGGGATCATGTAACTCGCCTTGAT</u>
<u>CGTTGGGAACCGGAGCTGAATGAAGCCATACCAAACGACGAGCGTGACACCACGATGCCTGTAGCAATGGCAAC</u>
<u>AACGTTGCGCAAACTATTAACTGGCGAACTACTTACTCTAGCTTCCCGGCAACAATTAATAGACTGGATGGAGGCG</u>
<u>GATAAAGTTGCAGGACCACTTCTGCGCTCGGCCCTTCCGGCTGGCTGGTTTATTGCTGATAAATCTGGAGCCGGTG</u>
<u>AGCGTGGGTCTCGCGGTATCATTGCAGCACTGGGGCCAGATGGTAAGCCCTCCCGTATCGTAGTTATCTACACGAC</u>
<u>GGGGAGTCAGGCAACTATGGATGAACGAAATAGACAGATCGCTGAGATAGGTGCCTCACTGATTAAGCATTGGT</u>
<u>AA</u>CTGTCAGACCAAGTTTACTCATATATACTTTAGATTGATTTAAAACTTCATTTTTAATTTAAAAGGATCTAGGTGA
AGATCCTTTTTGATAATCTCATGACCAAAATCCCTTAACGTGAGTTTTCGTTCCACTGAGCGTCAGACCCCGTAGAA
AAGATCAAAGGATCTTCTTGAGATCCTTTTTTTCTGCGCGTAATCTGCTGCTTGCAAACAAAAAAACCACCGCTACC
AGCGGTGGTTTGTTTGCCGGATCAAGAGCTACCAACTCTTTTTCCGAAGGTAACTGGCTTCAGCAGAGCGCAGATA
CCAAATACTGTCCTTCTAGTGTAGCCGTAGTTAGGCCACCACTTCAAGAACTCTGTAGCACCGCGTACATACCTCGC
TCTGCTAATCCTGTTACCAGTGGCTGCTGCCAGTGGCGATAAGTCGTGTCTTACCGGGTTGGACTCAAGACGATAG
TTACCGGATAAGGCGCAGCGGTCGGGCTGAACGGGGGGTTCGTGCACACAGCCCAGCTTGGAGCGAACGACCTA
CACCGAACTGAGATACCTACAGCGTGAGCTATGAGAAAGCGCCACGCTTCCCGAAGGGAGAAAGGCGGACAGGT
ATCCGGTAAGCGGCAGGGTCGGAACAGGAGAGCGCACGAGGGAGCTTCCAGGGGGAAACGCCTGGTATCTTTAT
AGTCCTGTCGGGTTTCGCCACCTCTGACTTGAGCGTCGATTTTTGTGATGCTCGTCAGGGGGCGGAGCCTATGGA
AAAACGCCAGCAACGCGGCCTTTTTACGGTTCCTGGCCTTTTGCTGGCCTTTTGCTCACATGTTCTTTCCTGCGTTAT

FIG. 10 (continued)

CCCCTGATTCTGTGGATAACCGTATTACCGGGTTTGAGTGAGCTGATACCGCTCGCCGCAGCCGAACGACCGAGC
GCAGCGAGTCAGTGAGCGACCAAGCGGAAGAGC

FIG. 11

SEQ ID NO: 5 rAAVrh74.MCK.micro-dystrophin

Main features:
MCK promoter
Chimeric intron sequence
Human codon optimized micro-dystrophin sequence -
Poly A tail
Ampicillin resistance
pGEX plasmid backbone with pBR322 origin or replication GCCCAATACGCAAACCGCCTCTCCCCGCGCGTTGGCCGATTCATTAATGCAGCTGGCGCGCTCGCTCGCTCACTGA
GGCCGCCCGGGCAAAGCCCGGGCGTCGGGCGACCTTTGGTCGCCCGGCCTCAGTGAGCGAGCGAGCGCGCAGA
GAGGGAGTGGCCAACTCCATCACTAGGGGTTCCTTGTAGTTAATGATTAACCCGCCATGCTAATTATCTACGTAGC
CATGTCTAGACAGCCACTATGGGTCTAGGCTGCCCATGTAAGGAGGCAAGGCCTGGGGACACCCGAGATGCCTG
GTTATAATTAACCCAGACATGTGGCTGCTCCCCCCCCCAACACCTGCTGCCTGAGCCTCACCCCCACCCCGGTGCC
TGGGTCTTAGGCTCTGTACACCATGGAGGAGAAGCTCGCTCTAAAAATAACCCTGTCCCTGGTGGGCTGTGGGGG
ACTGAGGGCAGGCTGTAACAGGCTTGGGGGCCAGGGCTTATACGTGCCTGGGACTCCCAAAGTATTACTGTTCCA
TGTTCCCGGCGAAGGGCCAGCTGTCCCCGCCAGCTAGACTCAGCACTTAGTTTAGGAACCAGTGAGCAAGTCAG
CCCTTGGGGCAGCCCATACAAGGCCATGGGGCTGGGCAAGCTGCACGCCTGGGTCCGGGGTGGGCACGGTGCCC
GGGCAACGAGCTGAAAGCTCATCTGCTCTCAGGGGCCCCTCCCTGGGGACAGCCCCTCCTGGCTAGTCACACCCT
GTAGGCTCCTCTATATAACCCAGGGGCACAGGGGCTGCCCCCGGGTCACCACCACCTCCACAGCACAGACAGACA
CTCAGGAGCCAGCCAGCCAGGTAAGTTTAGTCTTTTTGTCTTTTATTTCAGGTCCCGGATCCGGTGGTGGTGCAAA
TCAAAGAACTGCTCCTCAGTGGATGTTGCCTTTACTTCTAGGCCTGTACGGAAGTGTTACTTCTGCTCTAAAAGCTG
CGGAATTGTACCCGCGGCCGCCACCATGCTGTGGTGGGAGGAGGTGGAGGATTGTTATGAAAGGGAGGACGTG
CAGAAGAAGACTTTTACCAAGTGGGTGAACGCTCAGTTCAGCAAATTTGGGAAGCAGCACATCGAGAATCTGTT
TTCCGACCTGCAGGATGGGAGACGGCTGCTGGATCTGCTGGAAGGACTGACTGGCCAGAAGCTGCCCAAAGAG
AAGGGGAGCACTAGGGTGCACGCCCTGAACAACGTGAACAAAGCTCTGAGAGTGCTGCAGAACAACAACGTG
GATCTGGTGAATATTGGCAGTACTGATATCGTGGACGGGAACCACAAACTGACACTGGGCCTGATCTGGAACAT
TATTCTGCACTGGCAGGTGAAAAATGTGATGAAGAACATCATGGCCGGGCTGCAGCAGACCAATTCCGAGAAG
ATCCTGCTGTCTTGGGTGCGGCAGAGCACCCGCAACTATCCCCAGGTGAACGTGATTAACTTCACTACATCCTGG
AGCGACGGGCTGGCCCTGAATGCTCTGATTCACAGCCACAGGCCTGATCTGTTCGACTGGAATAGCGTGGTGTG FIG. 11 (continued)

CCAGCAGTCTGCCACACAGCGCCTGGAACATGCCTTCAATATCGCTCGGTACCAGCTGGGGATCGAAAAACTGC
TGGACCCAGAGGATGTGGACACTACATACCCAGATAAAAAGTCTATTCTGATGTACATTACTAGCCTGTTCCAGG
TGCTGCCACAGCAGGTGTCTATTGAAGCCATTCAGGAGGTGGAAATGCTGCCCCGCCCCCCCAAAGTGACTAAA
GAGGAGCATTTTCAGCTGCATCATCAGATGCATTACAGCCAGCAGATTACCGTGAGCCTGGCTCAGGGATATGA
GCGCACCAGTAGTCCAAAACCACGGTTCAAGTCCTACGCTTATACCCAGGCTGCCTACGTGACAACTAGCGACCC
TACTAGATCCCCCTTTCCATCCCAGCACCTGGAGGCCCCAGAGGACAAGAGCTTTGGGTCCAGCCTGATGGAAA
GCGAGGTGAATCTGGATCGGTACCAGACAGCCCTGGAGGAGGTGCTGAGCTGGCTGCTGAGTGCTGAAGACAC
ACTGCAGGCCCAGGGCGAAATTTCCAATGACGTGGAAGTGGTGAAGGATCAGTTCCACACACACGAGGGCTAT
ATGATGGACCTGACAGCTCACCAGGGGCGCGTGGGCAATATCCTGCAGCTGGGCTCTAAACTGATCGGCACCGG
GAAACTGAGTGAGGACGAGGAAACAGAAGTGCAGGAGCAGATGAACCTGCTGAACAGCCGCTGGGAGTGTCT
GAGAGTGGCTAGTATGGAGAAGCAGTCCAACCTGCACCGGGTGCTGATGGACCTGCAGAACCAGAAACTGAAA
GAGCTGAACGACTGGCTGACAAAGACTGAGGAACGCACAAGGAAGATGGAGGAGGAGCCACTGGGACCCGA
CCTGGAGGATCTGAAGAGACAGGTGCAGCAGCATAAGGTGCTGCAGGAGGATCTGGAACAGGAGCAGGTGCG
GGTGAACTCCCTGACACATATGGTGGTGGTGGTGGACGAATCTAGTGGAGATCACGCCACCGCCGCCCTGGAG
GAACAGCTGAAGGTGCTGGGGGACCGGTGGGCCAACATTTGCCGGTGGACCGAGGACAGGTGGGTGCTGCTG
CAGGACATCCTGCTGAAATGGCAGAGGCTGACCGAGGAGCAGTGTCTGTTTAGTGCTTGGCTGAGCGAGAAAG
AGGACGCCGTGAACAAGATCCACACAACCGGCTTTAAGGATCAGAACGAAATGCTGTCTAGCCTGCAGAAACT
GGCTGTGCTGAAGGCCGATCTGGAGAAAAAGAAGCAGAGCATGGGCAAACTGTATAGCCTGAAACAGGACCT
GCTGAGCACCCTGAAGAACAAGAGCGTGACCCAGAAGACAGAAGCCTGGCTGGATAACTTTGCCCGCTGCTGG
GACAACCTGGTGCAGAAACTGGAGAAAAGTACAGCTCAGATCTCTCAGGCTGTGACCACAACCCAGCCTAGCCT
GACCCAGACAACCGTGATGGAAACCGTGACCACCGTGACAACCCGCGAACAGATCCTGGTGAAACATGCCCAG
GAAGAGCTGCCACCTCCACCTCCCCAGAAGAAGAGAACCCTGGAGCGGCTGCAGGAGCTGCAGGAAGCCACTG
ACGAACTGGACCTGAAGCTGAGGCAGGCCGAAGTGATTAAGGGGTCTTGGCAGCCTGTGGGCGATCTGCTGAT
TGATTCCCTGCAGGACCACCTGGAAAAGGTGAAGGCTCTGAGAGGCGAAATTGCTCCACTGAAGGAGAACGTG
AGTCATGTGAACGATCTGGCTAGACAGCTGACAACACTGGGCATCCAGCTGAGCCCATACAATCTGAGCACACT
GGAGGACCTGAATACCAGGTGGAAGCTGCTGCAGGTGGCTGTGGAAGACCGGGTGCGGCAGCTGCATGAGGC
CCATCGCGACTTCGGACCAGCCAGCCAGCACTTTCTGAGCACATCCGTGCAGGGGCCCTGGGAGAGGGCCATTT
CTCCCAACAAGGTGCCCTACTATATTAATCACGAGACCCAGACCACTTGTTGGGACCATCCCAAGATGACAGAAC
TGTACCAGTCCCTGGCCGATCTGAACAACGTGAGGTTTAGCGCTTACAGAACCGCTATGAAGCTGAGACGGCTG
CAGAAGGCCCTGTGCCTGGATCTGCTGTCCCTGTCCGCCGCCTGCGATGCCCTGGATCAGCATAATCTGAAGCAG
AACGATCAGCCAATGGATATCCTGCAGATCATCAACTGCCTGACCACTATCTACGACAGGCTGGAGCAGGAGCA
CAACAACCTGGTGAACGTGCCTCTGTGCGTGGATATGTGCCTGAACTGGCTGCTGAACGTGTATGACACTGGGC

FIG. 11 (continued)

GCACCGGCCGGATCAGAGTGCTGAGTTTTAAAACTGGGATTATCTCCCTGTGTAAGGCCCACCTGGAGGACAAG
TACAGGTACCTGTTCAAGCAGGTGGCTAGTAGCACTGGATTTTGTGACCAGCGCCGCCTGGGACTGCTGCTGCA
TGATAGTATCCAGATTCCTAGACAGCTGGGAGAGGTGGCTAGTTTCGGAGGATCTAACATCGAACCCAGCGTGC
GCAGCTGTTTCCAGTTTGCCAATAACAAACCTGAAATCGAGGCTGCTCTGTTCCTGGATTGGATGCGCCTGGAAC
CACAGAGCATGGTGTGGCTGCCTGTGCTGCACAGAGTGGCTGCCGCCGAAACTGCCAAGCACCAGGCTAAATGC
AACATCTGCAAGGAATGTCCCATTATCGGCTTTCGCTACAGGAGTCTGAAACATTTTAACTACGATATTTGCCAG
AGCTGCTTCTTTTCCGGAAGAGTGGCCAAAGGACACAAGATGCACTACCCTATGGTGGAATATTGCACCCCAAC
TACATCTGGCGAAGATGTGCGCGATTTTGCCAAGGTGCTGAAGAATAAGTTTCGGACTAAGAGGTACTTCGCCA
AGCACCCCGCATGGGGTATCTGCCAGTGCAGACAGTGCTGGAAGGAGACAATATGGAGACCGATACAATGTG
AGCGGCCGCAATAAAAGATCTTTATTTTCATTAGATCTGTGTGTTGGTTTTTTGTGTGTCTAGAGCATGGCTACGTA
GATAAGTAGCATGGCGGGTTAATCATTAACTACAAGGAACCCCTAGTGATGGAGTTGGCCACTCCCTCTCTGCGCG
CTCGCTCGCTCACTGAGGCCGGGCGACCAAAGGTCGCCCGACGCCCGGGCTTTGCCCGGGCGGCCTCAGTGAGC
GAGCGAGCGCGCCAGCTGGCGTAATAGCGAAGAGGCCCGCACCGATCGCCCTTCCCAACAGTTGCGCAGCCTGA
ATGGCGAATGGAAGTTCCAGACGATTGAGCGTCAAAATGTAGGTATTTCCATGAGCGTTTTTCCTGTTGCAATGGC
TGGCGGTAATATTGTTCTGGATATTACCAGCAAGGCCGATAGTTTGAGTTCTTCTACTCAGGCAAGTGATGTTATTA
CTAATCAAAGAAGTATTGCGACAACGGTTAATTTGCGTGATGGACAGACTCTTTTACTCGGTGGCCTCACTGATTA
TAAAAACACTTCTCAGGATTCTGGCGTACCGTTCCTGTCTAAAATCCCTTTAATCGGCCTCCTGTTTAGCTCCCGCTC
TGATTCTAACGAGGAAAGCACGTTATACGTGCTCGTCAAAGCAACCATAGTACGCGCCCTGTAGCGGCGCATTAA
GCGCGGCGGGTGTGGTGGTTACGCGCAGCGTGACCGCTACACTTGCCAGCGCCCTAGCGCCCGCTCCTTTCGCTTT
CTTCCCTTCCTTTCTCGCCACGTTCGCCGGCTTTCCCCGTCAAGCTCTAAATCGGGGGCTCCCTTTAGGGTTCCGATT
TAGTGATTTACGGCACCTCGACCCCAAAAAACTTGATTAGGGTGATGGTTCACGTAGTGGGCCATCGCCCTGATAG
ACGGTTTTTCGCCCTTTGACGTTGGAGTCCACGTTCTTTAATAGTGGACTCTTGTTCCAAACTGGAACAACACTCAA
CCCTATCTCGGTCTATTCTTTTGATTTATAAGGGATTTTGCCGATTTCGGCCTATTGGTTAAAAAATGAGCTGATTTA
ACAAAAATTTAACGCGAATTTTAACAAAATATTAACGTTTACAATTTAAATATTTGCTTATACAATCTTCCTGTTTTT
GGGGCTTTTCTGATTATCAACCGGGGTACATATGATTGACATGCTAGTTTTACGATTACCGTTCATCGATTCTCTTG
TTTGCTCCAGACTCTCAGGCAATGACCTGATAGCCTTTGTAGAGACCTCTCAAAAATAGCTACCCTCTCCGGCATGA
ATTTATCAGCTAGAACGGTTGAATATCATATTGATGGTGATTTGACTGTCTCCGGCCTTTCTCACCCGTTTGAATCTT
TACCTACACATTACTCAGGCATTGCATTTAAAATATATGAGGGTTCTAAAAATTTTTATCCTTGCGTTGAAATAAAG
GCTTCTCCCGCAAAAGTATTACAGGGTCATAATGTTTTTGGTACAACCGATTTAGCTTTATGCTCTGAGGCTTTATT
GCTTAATTTTGCTAATTCTTTGCCTTGCCTGTATGATTTATTGGATGTTGGAAGTTCCTGATGCGGTATTTTCTCCTT
ACGCATCTGTGCGGTATTTCACACCGCATATGGTGCACTCTCAGTACAATCTGCTCTGATGCCGCATAGTTAAGCCA
GCCCCGACACCCGCCAACACCCGCTGACGCGCCCTGACGGGCTTGTCTGCTCCCGGCATCCGCTTACAGACAAGCT

FIG. 11 (continued)

GTGACCGTCTCCGGGAGCTGCATGTGTCAGAGGTTTTCACCGTCATCACCGAAACGCGCGAGACGAAAGGGCCTC
GTGATACGCCTATTTTTATAGGTTAATGTCATGATAATAATGGTTTCTTAGACGTCAGGTGGCACTTTTCGGGGAAA
TGTGCGCGGAACCCCTATTTGTTTATTTTTCTAAATACATTCAAATATGTATCCGCTCATGAGACAATAACCCTGATA
AATGCTTCAATAATATTGAAAAAGGAAGAGTATGAGTATTCAACATTTCCGTGTCGCCCTTATTCCCTTTTTTGCGG
CATTTTGCCTTCCTGTTTTTGCTCACCCAGAAACGCTGGTGAAAGTAAAAGATGCTGAAGATCAGTTGGGTGCACG
AGTGGGTTACATCGAACTGGATCTCAACAGCGGTAAGATCCTTGAGAGTTTTCGCCCCGAAGAACGTTTTCCAATG
ATGAGCACTTTTAAAGTTCTGCTATGTGGCGCGGTATTATCCCGTATTGACGCCGGGCAAGAGCAACTCGGTCGCC
GCATACACTATTCTCAGAATGACTTGGTTGAGTACTCACCAGTCACAGAAAAGCATCTTACGGATGGCATGACAGT
AAGAGAATTATGCAGTGCTGCCATAACCATGAGTGATAACACTGCGGCCAACTTACTTCTGACAACGATCGGAGG
ACCGAAGGAGCTAACCGCTTTTTTGCACAACATGGGGGATCATGTAACTCGCCTTGATCGTTGGGAACCGGAGCT
GAATGAAGCCATACCAAACGACGAGCGTGACACCACGATGCCTGTAGCAATGGCAACAACGTTGCGCAAACTATT
AACTGGCGAACTACTTACTCTAGCTTCCCGGCAACAATTAATAGACTGGATGGAGGCGGATAAAGTTGCAGGACC
ACTTCTGCGCTCGGCCCTTCCGGCTGGCTGGTTTATTGCTGATAAATCTGGAGCCGGTGAGCGTGGGTCTCGCGGT
ATCATTGCAGCACTGGGGCCAGATGGTAAGCCCTCCCGTATCGTAGTTATCTACACGACGGGGAGTCAGGCAACT
ATGGATGAACGAAATAGACAGATCGCTGAGATAGGTGCCTCACTGATTAAGCATTGGTAACTGTCAGACCAAGTT
TACTCATATATACTTTAGATTGATTTAAAACTTCATTTTTAATTTAAAAGGATCTAGGTGAAGATCCTTTTTGATAAT
CTCATGACCAAAATCCCTTAACGTGAGTTTTCGTTCCACTGAGCGTCAGACCCCGTAGAAAAGATCAAAGGATCTT
CTTGAGATCCTTTTTTTCTGCGCGTAATCTGCTGCTTGCAAACAAAAAAACCACCGCTACCAGCGGTGGTTTGTTTG
CCGGATCAAGAGCTACCAACTCTTTTTCCGAAGGTAACTGGCTTCAGCAGAGCGCAGATACCAAATACTGTCCTTC
TAGTGTAGCCGTAGTTAGGCCACCACTTCAAGAACTCTGTAGCACCGCGTACATACCTCGCTCTGCTAATCCTGTTA
CCAGTGGCTGCTGCCAGTGGCGATAAGTCGTGTCTTACCGGGTTGGACTCAAGACGATAGTTACCGGATAAGGCG
CAGCGGTCGGGCTGAACGGGGGGTTCGTGCACACAGCCCAGCTTGGAGCGAACGACCTACACCGAACTGAGATA
CCTACAGCGTGAGCTATGAGAAAGCGCCACGCTTCCCGAAGGGAGAAAGGCGGACAGGTATCCGGTAAGCGGCA
GGGTCGGAACAGGAGAGCGCACGAGGGAGCTTCCAGGGGGAAACGCCTGGTATCTTTATAGTCCTGTCGGGTTT
CGCCACCTCTGACTTGAGCGTCGATTTTTGTGATGCTCGTCAGGGGGCGGAGCCTATGGAAAAACGCCAGCAAC
GCGGCCTTTTTACGGTTCCTGGCCTTTTGCTGGCCTTTTGCTCACATGTTCTTTCCTGCGTTATCCCCTGATTCTGTG
GATAACCGTATTACCGGGTTTGAGTGAGCTGATACCGCTCGCCGCAGCCGAACGACCGAGCGCAGCGAGTCAGTG
AGCGACCAAGCGGAAGAGC

FIG. 12 pAAV.CMV.miR29C Sequence (SEQ ID NO: 6)

Main features:
CMV promoter- 120-526
EF1a Intron- 927-1087, 1380-1854
miR-29c- 1257-1284
shRNA-miR29-c with primary seed sequence- 1088-1375
PolyA- 1896-2091

CAGCAGCTGCGCGCTCGCTCGCTCACTGAGGCCGCCCGGGCAAAGCCCGGGCGTCGGGCGACCTTTGGTCGCCCG
GCCTCAGTGAGCGAGCGAGCGCGCAGAGAGGGAGTGGGGTTAAACTCGTTACATAACTTACGGTAAATGGCCCG
CCTGGCTGACCGCCCAACGACCCCGCCCATTGACGTCAATAATGACGTATGTTCCCATAGTAACGCCAATAGGGA
CTTTCCATTGACGTCAATGGGTGGAGTATTTACGGTAAACTGCCCACTTGGCAGTACATCAAGTGTATCATATGCC
AAGTACGCCCCCTATTGACGTCAATGACGGTAAATGGCCCGCCTGGCATTATGCCCAGTACATGACCTTATGGGAC
TTTCCTACTTGGCAGTACATCTACGTATTAGTCATCGCTATTACCATGGTGATGCGGTTTTGGCAGTACATCAATGG
GCGTGGATAGCGGTTTGACTCACGGGGATTTCCAAGTCTCCACCCCATTGACGTCAATGGGAGTTTGTTTTGGCAC
CAAAATCAACGGGACTTTCCAAAATGTCGTAACAACTCCGCCCCATTGACGCAAATGGGCGGTAGGCGTGTACGG
TGGGAGGTCTATATAAGCAGAGCTCGTTTAGTGAACCGTCAGATCGCCTGGAGACGCCATCCACGCTGTTTTGACC
TCCATAGAAGACACCGGGACCGATCCAGCCTCCGGACTCTAGAGGATCCGGTACTCGAGGAACTGAAAAACCAGA
AAGTTAACTGGTAAGTTTAGTCTTTTTGTCTTTTATTTCAGGTCCCGGATCCGGTGGTGGTGCAAATCAAAGAACTG
CTCCTCAGTGGATGTTGCCTTTACTTCTAGGCCTGTACGGAAGTGTTACTTCTGCTCTAAAAGCTGCGGAATTGTAC
CCGGGGCCGATCCACCGGTCTTTTTCGCAACGGGTTTGCCGCCAGAACACAGGTAAGTGCCGTGTGTGGTTCCCG
CGGGCGGCGACGGGGCCCGTGCGTCCCAGCGCACATGTTCGGCGAGGCGGGGCCTGCGAGCGCGGCCACCGAG
AATCGGACGGGGGTAGTCTCAAGCTGGCC**GGCCTGTTTGAATGAGGCTTCAGTACTTTACAGAATCGTTGCCTGC
ACATCTTGGAAACACTTGCTGGGATTACTTCTTCAGGTTAACCCAACAGAAGGCTCGAGAAGGTATATTGCTGTT
GACAGTGAGCGCAACCGATTTCAAATGGTGCTAGAGTGAAGCCACAGATG**TCTAGCACCATTTGAAATCGGTTA
TGCCTACTGCCTCGGAATTCAAGGGGCTACTTTAGGAGCAATTATCTTGTTTACTAAAACTGAATACCTTGCTATC
TCTTTGATACATTGGCCGGCCTGCTCTGGTGCCTGGCCTCGCGCCGCCGTGTATCGCCCCGCCCTGGGCGGCAAG
GCTGGCCCGGTCGGCACCAGTTGCGTGAGCGGAAAGATGGCCGCTTCCCGGCCCTGCTGCAGGGAGCTCAAAAT
GGAGGACGCGGCGCTCGGGAGAGCGGGCGGGTGAGTCACCCACACAAAGGAAAAGGGCCTTTCCGTCCTCAGC
CGTCGCTTCATGTGACTCCACGAGTACCGGGCGCCGTCCAGGCACCTCGATTAGTTCTCGAGCTTTTGGAGTACG
TCGTCTTTAGGTTGGGGGAGGGGTTTATGCGATGGAGTTTCCCCACACTGAGTGGGTGGAGACTGAAGTTAGG
CCAGCTTGGCACTTGATGTAATTCTCCTTGGAATTTGCCCTTTTTGAGTTTGGATCTTGGTTCATTCTCAAGCCTCAG
ACAGTGGTTCAAAGTTTTTTTCTTCCATTTCAGGTGTCGTGAAAAGCTAGCGCTACCGGACTCAGATCTCGAGCTCA
AGCTGCGGGGATCCAGACATGATAAGATACATTGATGAGTTTGGACAAACCACAACTAGAATGCAGTGAAAAAAA
TGCTTTATTTGTGAAATTTGTGATGCTATTGCTTTATTTGTAACCATTATAAGCTGCAATAAACAAGTTAACAACAAC
AATTGCATTCATTTTATGTTTCAGGTTCAGGGGGAGGTGTGGGAGGTTTTTTCACTAGTAGCATGGCTACGTAGAT
AAGTAGCATGGCGGGTTAATCATTAACTACAAGGAACCCCTAGTGATGGAGTTGGCCACTCCCTCTCTGCGCGCTC
GCTCGCTCACTGAGGCCGGGCGACCAAAGGTCGCCCGACGCCCGGGCTTTGCCCGGGCGGCCTCAGTGAGCGAG
CGAGCGCGCCAGCTGGCGTAATAGCGAAGAGGCCCGCACCGATCGCCCTTCCCAACAGTTGCGCAGCCTGAATGG
CGAATGGAATTCCAGACGATTGAGCGTCAAAATGTAGGTATTTCCATGAGCGTTTTTCCTGTTGCAATGGCTGGCG
GTAATATTGTTCTGGATATTACCAGCAAGGCCGATAGTTTGAGTTCTTCTACTCAGGCAAGTGATGTTATTACTAAT
CAAAGAAGTATTGCGACAACGGTTAATTTGCGTGATGGACAGACTCTTTTACTCGGTGGCCTCACTGATTATAAAA

FIG. 12 (continued)

ACACTTCTCAGGATTCTGGCGTACCGTTCCTGTCTAAAATCCCTTTAATCGGCCTCCTGTTTAGCTCCCGCTCTGATT
CTAACGAGGAAAGCACGTTATACGTGCTCGTCAAAGCAAC
CATAGTACGCGCCCTGTAGCGGCGCATTAAGCGCGGCGGGTGTGGTGGTTACGCGCAGCGTGACCGCTACACTTG
CCAGCGCCCTAGCGCCCGCTCCTTTCGCTTTCTTCCCTTCCTTTCTCGCCACGTTCGCCGGCTTTCCCCGTCAAGCTCT
AAATCGGGGGCTCCCTTTAGGGTTCCGATTTAGTGCTTTACGGCACCTCGACCCCAAAAAACTTGATTAGGGTGAT
GGTTCACGTAGTGGGCCATCGCCCTGATAGACGGTTTTTCGCCCTTTGACGTTGGAGTCCACGTTCTTTAATAGTG
GACTCTTGTTCCAAACTGGAACAACACTCAACCCTATCTCGGTCTATTCTTTTGATTTATAAGGGATTTTGCCGATTT
CGGCCTATTGGTTAAAAAATGAGCTGATTTAACAAAAATTTAACGCGAATTTTAACAAAATATTAACGTTTACAATT
TAAATATTTGCTTATACAATCTTCCTGTTTTTGGGGCTTTTCTGATTATCAACCGGGGTACATATGATTGACATGCTA
GTTTTACGATTACCGTTCATCGATTCTCTTGTTTGCTCCAGACTCTCAGGCAATGACCTGATAGCCTTTGTAGAGACC
TCTCAAAAATAGCTACCCTCTCCGGCATGAATTTATCAGCTAGAACGGTTGAATATCATATTGATGGTGATTTGACT
GTCTCCGGCCTTTCTCACCCGTTTGAATCTTTACCTACACATTACTCAGGCATTGCATTTAAAATATATGAGGGTTCT
AAAAATTTTTATCCTTGCGTTGAAATAAAGGCTTCTCCCGCAAAAGTATTACAGGGTCATAATGTTTTTGGTACAAC
CGATTTAGCTTTATGCTCTGAGGCTTTATTGCTTAATTTTGCTAATTCTTTGCCTTGCCTGTATGATTTATTGGATGTT
GGAATTCCTGATGCGGTATTTTCTCCTTACGCATCTGTGCGGTATTTCACACCGCATATGGTGCACTCTCAGTACAA
TCTGCTCTGATGCCGCATAGTTAAGCCAGCCCCGACACCCGCCAACACCCGCTGACGCGCCCTGACGGGCTTGTCT
GCTCCCGGCATCCGCTTACAGACAAGCTGTGACCGTCTCCGGGAGCTGCATGTGTCAGAGGTTTTCACCGTCATCA
CCGAAACGCGCGAGACGAAAGGGCCTCGTGATACGCCTATTTTTATAGGTTAATGTCATGATAATAATGGTTTCTT
AGACGTCAGGTGGCACTTTTCGGGGAAATGTGCGCGGAACCCCTATTTGTTTATTTTTCTAAATACATTCAAATATG
TATCCGCTCATGAGACAATAACCCTGATAAATGCTTCAATAATATTGAAAAAGGAAGAGTATGAGTATTCAACATT
TCCGTGTCGCCCTTATTCCCTTTTTTGCGGCATTTTGCCTTCCTGTTTTTGCTCACCCAGAAACGCTGGTGAAAGTAA
AAGATGCTGAAGATCAGTTGGGTGCACGAGTGGGTTACATCGAACTGGATCTCAACAGCGGTAAGATCCTTGAGA
GTTTTCGCCCCGAAGAACGTTTTCCAATGATGAGCACTTTTAAAGTTCTGCTATGTGGCGCGGTATTATCCCGTATT
GACGCCGGGCAAGAGCAACTCGGTCGCCGCATACACTATTCTCAGAATGACTTGGTTGAGTACTCACCAGTCACA
GAAAAGCATCTTACGGATGGCATGACAGTAAGAGAATTATGCAGTGCTGCCATAACCATGAGTGATAACACTGCG
GCCAACTTACTTCTGACAACGATCGGAGGACCGAAGGAGCTAACCGCTTTTTTGCACAACATGGGGGATCATGTA
ACTCGCCTTGATCGTTGGGAACCGGAGCTGAATGAAGCCATACCAAACGACGAGCGTGACACCACGATGCCTGTA
GCAATGGCAACAACGTTGCGCAAACTATTAACTGGCGAACTACTTACTCTAGCTTCCCGGCAACAATTAATAGACT
GGATGGAGGCGGATAAAGTTGCAGGACCACTTCTGCGCTCGGCCCTTCCGGCTGGCTGGTTTATTGCTGATAAAT
CTGGAGCCGGTGAGCGTGGGTCTCGCGGTATCATTGCAGCACTGGGGCCAGATGGTAAGCCCTCCCGTATCGTAG
TTATCTACACGACGGGGAGTCAGGCAACTATGGATGAACGAAATAGACAGATCGCTGAGATAGGTGCCTCACTGA
TTAAGCATTGGTAACTGTCAGACCAAGTTTACTCATATATACTTTAGATTGATTTAAAACTTCATTTTTAATTTAAAA
GGATCTAGGTGAAGATCCTTTTTGATAATCTCATGACCAAAATCCCTTAACGTGAGTTTTCGTTCCACTGAGCGTCA
GACCCCGTAGAAAAGATCAAAGGATCTTCTTGAGATCCTTTTTTTCTGCGCGTAATCTGCTGCTTGCAAACAAAAAA
ACCACCGCTACCAGCGGTGGTTTGTTTGCCGGATCAAGAGCTACCAACTCTTTTTCCGAAGGTAACTGGCTTCAGC
AGAGCGCAGATACCAAATACTGTCCTTCTAGTGTAGCCGTAGTTAGGCCACCACTTCAAGAACTCTGTAGCACCGC
CTACATACCTCGCTCTGCTAATCCTGTTACCAGTGGCTGCTGCCAGTGGCGATAAGTCGTGTCTTACCGGGTTGGA
CTCAAGACGATAGTTACCGGATAAGGCGCAGCGGTCGGGCTGAACGGGGGGTTCGTGCACACAGCCCAGCTTGG
AGCGAACGACCTACACCGAACTGAGATACCTACAGCGTGAGCTATGAGAAAGCGCCACGCTTCCCGAAGGGAGA
AAGGCGGACAGGTATCCGGTAAGCGGCAGGGTCGGAACAGGAGAGCGCACGAGGGAGCTTCCAGGGGGAAAC
GCCTGGTATCTTTATAGTCCTGTCGGGTTTCGCCACCTCTGACTTGAGCGTCGATTTTTGTGATGCTCGTCAGGGGG
GCGGAGCCTATGGAAAAACGCCAGCAACGCGGCCTTTTTACGGTTCCTGGCCTTTTGCTGGCCTTTTGCTCACATG
TTCTTTCCTGCGTTATCCCCTGATTCTGTGGATAACCGTATTACCGCCTTTGAGTGAGCTGATACCGCTCGCCGCAG
CCGAACGACCGAGCGCAGCGAGTCAGTGAGCGAGGAAGCGGAAGAGCGCCCAATACGCAAACCGCCTCTCCCCG
CGCGTTGGCCGATTCATTAATG

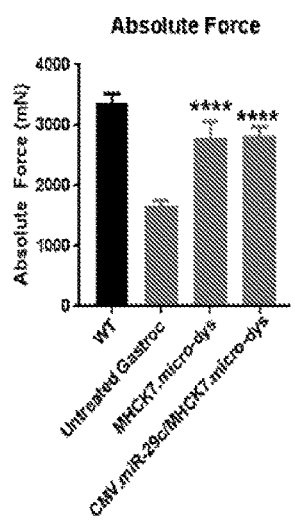
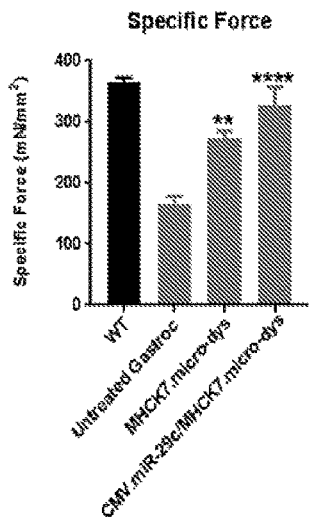
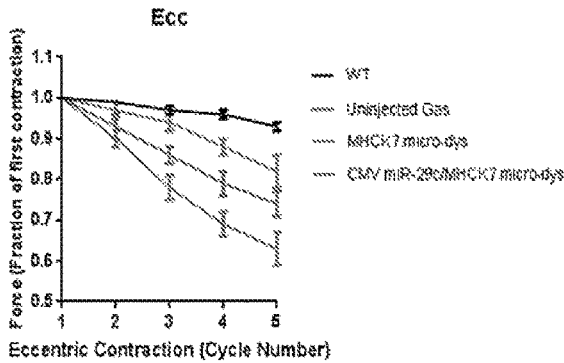
FIG. 13A  FIG. 13B  FIG. 13C
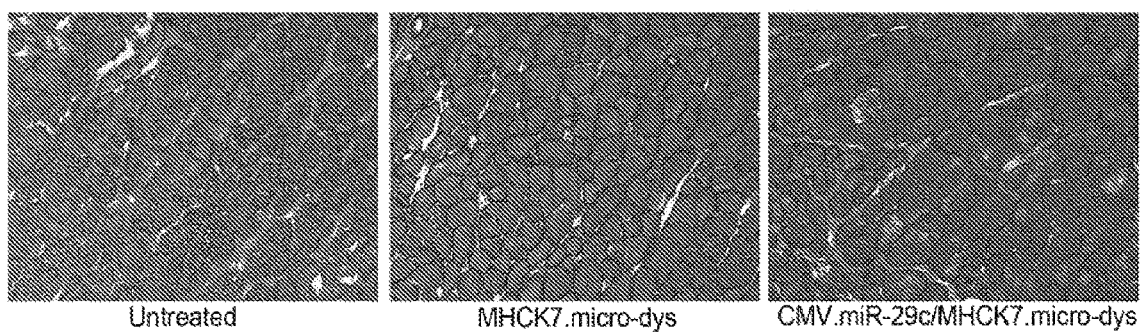

ADENO-ASSOCIATED VIRUS VECTOR DELIVERY OF MUSCLE SPECIFIC MICRO-DYSTROPHIN TO TREAT MUSCULAR DYSTROPHY

This application is a national phase application of International Patent Application No. PCT/US2018/022853, filed Mar. 16, 2018, which claims priority to U.S. Provisional Patent Application No. 62/573,955, filed Oct. 18, 2017, both of which are incorporated by reference in their entirety.

This invention was made with Government support under NS055958 awarded by the National Institutes of Health. The government has certain rights in the invention.

INCORPORATION BY REFERENCE OF MATERIAL SUBMITTED ELECTRONICALLY

This application contains, as a separate part of the disclosure, a Sequence Listing in computer-readable form which is incorporated by reference in its entirety and identified as follows: Filename: 52822_Seqlisting.txt; Size: 39,851 bytes, created; Mar. 13, 2018.

FIELD OF INVENTION

The invention provides a combination gene therapy comprising vectors, such as adeno-associated virus (AAV) vectors, expressing a miniaturized human micro-dystrophin gene and vectors such as adeno-associated virus (AAV) vectors, expressing miR29. The invention also provides method of using this combination therapy to express micro-dystrophin and miR29 in skeletal muscles including diaphragm and cardiac muscle and to protect muscle fibers from injury, increase muscle strength and reduce and/or prevent fibrosis in subjects suffering from muscular dystrophy.

BACKGROUND

The importance of muscle mass and strength for daily activities, such as locomotion and breathing, and for whole body metabolism is unequivocal. Deficits in muscle function produce muscular dystrophies (MDs) that are characterized by muscle weakness and wasting and have serious impacts on quality of life. The most well-characterized MDs result from mutations in genes encoding members of the dystrophin-associated protein complex (DAPC). These MDs result from membrane fragility associated with the loss of sarcolemmal-cytoskeleton tethering by the DAPC. Duchenne Muscular Dystrophy (DMD) is one of the most devastating muscle diseases affecting 1 in 5000 newborn males.

DMD is caused by mutations in the DMD gene leading to reductions in mRNA and the absence of dystrophin, a 427 kD sarcolemmal protein associated with the dystrophin-associated protein complex (DAPC) (Hoffman et al., Cell 51(6):919-28, 1987). The DAPC is composed of multiple proteins at the muscle sarcolemma that form a structural link between the extra-cellular matrix (ECM) and the cytoskeleton via dystrophin, an actin binding protein, and alpha-dystroglycan, a laminin-binding protein. These structural links act to stabilize the muscle cell membrane during contraction and protect against contraction-induced damage. With dystrophin loss, membrane fragility results in sarcolemmal tears and an influx of calcium, triggering calcium-activated proteases and segmental fiber necrosis (Straub et al., Curr Opin. Neurol. 10(2): 168-75, 1997). This uncontrolled cycle of muscle degeneration and regeneration ultimately exhausts the muscle stem cell population (Sacco et al., Cell, 2010. 143(7): p. 1059-71; Wallace et al., Annu Rev Physiol, 2009. 71: p. 37-57), resulting in progressive muscle weakness, endomysial inflammation, and fibrotic scarring.

Without membrane stabilization from dystrophin or a micro-dystrophin, DMD will manifest uncontrolled cycles of tissue injury and repair ultimately replaces lost muscle fibers with fibrotic scar tissue through connective tissue proliferation. Fibrosis is characterized by the excessive deposits of ECM matrix proteins, including collagen and elastin. ECM proteins are primarily produced from cytokines such as TGFβ that is released by activated fibroblasts responding to stress and inflammation. Although the primary pathological feature of DMD is myofiber degeneration and necrosis, fibrosis as a pathological consequence has equal repercussions. The over-production of fibrotic tissue restricts muscle regeneration and contributes to progressive muscle weakness in the DMD patient. In one study, the presence of fibrosis on initial DMD muscle biopsies was highly correlated with poor motor outcome at a 10-year follow-up (Desguerre et al., J Neuropathol Exp Neurol, 2009. 68(7): p. 762-7). These results point to fibrosis as a major contributor to DMD muscle dysfunction and highlight the need for early intervention prior to overt fibrosis.

Most anti-fibrotic therapies that have been tested in mdx mice act to block fibrotic cytokine signaling through inhibition of the TGFβ pathway. MicroRNAs (miRNAs) are single-stranded RNAs of ~22 nucleotides that mediate gene silencing at the post-transcriptional level by pairing with bases within the 3' UTR of mRNA, inhibiting translation or promoting mRNA degradation. A seed sequence of 7 bp at the 5' end of the miRNA targets the miRNA; additional recognition is provided by the remainder of the targeted sequence, as well as its secondary structure. MiRNAs play an important role in muscle disease pathology and exhibit expression profiles that are uniquely dependent on the type of muscular dystrophy in question (Eisenberg et al. Proc Natl Acad Sci USA, 2007. 104(43): p. 17016-21). A growing body of evidence suggests that miRNAs are involved in the fibrotic process in many organs including heart, liver, kidney, and lung (Jiang et al., Proc Natl Acad Sci USA, 2007. 104(43): p. 17016-21). Recently, the down-regulation of miR-29 was shown to contribute to cardiac fibrosis (Cacchiarelli et al., Cell Metab, 2010. 12(4): p. 341-51) and reduced expression of miR-29 was genetically linked with human DMD patient muscles (Eisenberg et al. Proc Natl Acad Sci USA, 2007. 104(43): p. 17016-2). The miR-29 family consists of three family members expressed from two bicistronic miRNA clusters. MiR-29a is coexpressed with miR-29b (miR-29b-1); miR-29c is coexpressed with a second copy of miR-29b (miR-29b-2). The miR-29 family shares a conserved seed sequence and miR-29a and miR-29b each differ by only one base from miR-29c. Furthermore, electroporation of miR-29 plasmid (a cluster of miR-29a and miR-29b-1) into mdx mouse muscle reduced the expression levels of ECM components, collagen and elastin, and strongly decreased collagen deposition in muscle sections within 25 days post-treatment (Cacchiarelli et al., Cell Metab, 2010. 12(4): p. 341-51).

Adeno-associated virus (AAV) is a replication-deficient parvovirus, the single-stranded DNA genome of which is about 4.7 kb in length including 145 nucleotide inverted terminal repeat (ITRs). There are multiple serotypes of AAV. The nucleotide sequences of the genomes of the AAV serotypes are known. For example, the nucleotide sequence of the AAV serotype 2 (AAV2) genome is presented in Srivastava et al., J Virol, 45: 555-564 (1983) as corrected by Ruffing et al., *J Gen Virol*, 75: 3385-3392 (1994). As other examples, the complete genome of AAV-1 is provided in GenBank Accession No. NC_002077; the complete genome of AAV-3 is provided in GenBank Accession No. NC_1829; the complete genome of AAV-4 is provided in GenBank Accession No. NC_001829; the AAV-5 genome is provided in GenBank Accession No. AF085716; the complete genome of AAV-6 is provided in GenBank Accession No. NC_00 1862; at least portions of AAV-7 and AAV-8 genomes are provided in GenBank Accession Nos. AX753246 and AX753249, respectively (see also U.S. Pat. Nos. 7,282,199 and 7,790,449 relating to AAV-8); the AAV-9 genome is provided in Gao et al., *J. Virol.*, 78: 6381-6388 (2004); the AAV-10 genome is provided in *Mol. Ther.*, 13(1): 67-76 (2006); and the AAV-11 genome is provided in *Virology*, 330(2): 375-383 (2004). Cloning of the AAVrh.74 serotype is described in Rodino-Klapac, et al. *Journal of translational medicine* 5, 45 (2007). Cis-acting sequences directing viral DNA replication (rep), encapsidation/packaging and host cell chromosome integration are contained within the ITRs. Three AAV promoters (named p5, p19, and p40 for their relative map locations) drive the expression of the two AAV internal open reading frames encoding rep and cap genes. The two rep promoters (p5 and p19), coupled with the differential splicing of the single AAV intron (e.g., at AAV2 nucleotides 2107 and 2227), result in the production of four rep proteins (rep 78, rep 68, rep 52, and rep 40) from the rep gene. Rep proteins possess multiple enzymatic properties that are ultimately responsible for replicating the viral genome. The cap gene is expressed from the p40 promoter and it encodes the three capsid proteins VP1, VP2, and VP3. Alternative splicing and non-consensus translational start sites are responsible for the production of the three related capsid proteins. A single consensus polyadenylation site is located at map position 95 of the AAV genome. The life cycle and genetics of AAV are reviewed in Muzyczka, *Current Topics in Microbiology and Immunology*, 158: 97-129 (1992).

AAV possesses unique features that make it attractive as a vector for delivering foreign DNA to cells, for example, in gene therapy. AAV infection of cells in culture is noncytopathic, and natural infection of humans and other animals is silent and asymptomatic. Moreover, AAV infects many mammalian cells allowing the possibility of targeting many different tissues in vivo. Moreover, AAV transduces slowly dividing and non-dividing cells, and can persist essentially for the lifetime of those cells as a transcriptionally active nuclear episome (extrachromosomal element). The AAV proviral genome is infectious as cloned DNA in plasmids which makes construction of recombinant genomes feasible. Furthermore, because the signals directing AAV replication, genome encapsidation and integration are contained within the ITRs of the AAV genome, some or all of the internal approximately 4.3 kb of the genome (encoding replication and structural capsid proteins, rep-cap) may be replaced with foreign DNA such as a gene cassette containing a promoter, a DNA of interest and a polyadenylation signal. The rep and cap proteins may be provided in trans. Another significant feature of AAV is that it is an extremely stable and hearty virus. It easily withstands the conditions used to inactivate adenovirus (56° C. to 65° C. for several hours), making cold preservation of AAV less critical. AAV may even be lyophilized. Finally, AAV-infected cells are not resistant to superinfection.

Multiple studies have demonstrated long-term (>1.5 years) recombinant AAV-mediated protein expression in muscle. See, Clark et al., *Hum Gene Ther*, 8: 659-669 (1997); Kessler et al., *Proc Nat. Acad Sc. USA*, 93: 14082-14087 (1996); and Xiao et al., *J Virol*, 70: 8098-8108 (1996). See also, Chao et al., *Mol Ther*, 2:619-623 (2000) and Chao et al., *Mol Ther*, 4:217-222 (2001). Moreover, because muscle is highly vascularized, recombinant AAV transduction has resulted in the appearance of transgene products in the systemic circulation following intramuscular injection as described in Herzog et al., *Proc Natl Acad Sci USA*, 94: 5804-5809 (1997) and Murphy et al., *Proc Natl Acad Sci USA*, 94: 13921-13926 (1997). Moreover, Lewis et al., *J Virol*, 76: 8769-8775 (2002) demonstrated that skeletal myofibers possess the necessary cellular factors for correct antibody glycosylation, folding, and secretion, indicating that muscle is capable of stable expression of secreted protein therapeutics.

Functional improvement in patients suffering from DMD and other muscular dystrophies requires gene restoration at an early stage of disease. There is a need for treatments that increase muscle strength and protect against muscle injury in patients suffering from DMD.

SUMMARY OF INVENTION

The present invention is directed to gene therapy vectors, e.g. AAV, expressing the micro-dystrophin gene to skeletal muscles including diaphragm and cardiac muscle to protect muscle fibers from injury, increase muscle strength and reduce and/or prevent fibrosis The invention provides for therapies and approaches for increasing muscular force and/or increasing muscle mass using gene therapy vectors to deliver micro-dystrophin to address the gene defect observed in DMD. As shown in Example 2, treatment with micro-dystrophin gene therapy resulted in a greater muscle force in vivo. Furthermore, delivery of micro-dystrophin gene therapy intramuscularly and systemically showed delivery of dystrophin to the muscles in mice models in vivo.

In one embodiment, the invention provides for a rAAV vector comprising a muscle specific control element nucleotide sequence, and a nucleotide sequence encoding the micro-dystrophin protein. For example, the nucleotide sequence encodes a functional micro-dystrophin protein, wherein the nucleotide is, e.g., at least at least 65%, at least 70%, at least 75%, at least 80%, 81%, 82%, 83%, 84%, 85%, 86%, 87%, 88%, or 89%, more typically at least 90%, 91%, 92%, 93%, or 94% and even more typically at least 95%, 96%, 97%, 98%, 99% or 100% sequence identity to SEQ ID NO: 1, wherein the protein retains micro-dystrophin activity. The micro-dystrophin protein provides stability to the muscle membrane during muscle contraction, e.g. micro-dystrophin acts as a shock absorber during muscle contraction.

The invention also provides for rAAV vectors wherein the nucleotide sequence encodes a functional micro-dystrophin protein comprising a nucleotide sequence that hybridizes under stringent conditions to the nucleic acid sequence of SEQ ID NO: 1, or compliments thereof, and encodes a functional micro-dystrophin protein.

The term "stringent" is used to refer to conditions that are commonly understood in the art as stringent. Hybridization stringency is principally determined by temperature, ionic strength, and the concentration of denaturing agents such as formamide. Examples of stringent conditions for hybridization and washing are 0.015 M sodium chloride, 0.0015 M sodium citrate at 65-68° C. or 0.015 M sodium chloride, 0.0015M sodium citrate, and 50% formamide at 42° C. See Sambrook et al., *Molecular Cloning: A Laboratory Manual*, 2nd Ed., Cold Spring Harbor Laboratory, (Cold Spring Harbor, N.Y. 1989). More stringent conditions (such as higher temperature, lower ionic strength, higher formamide, or other denaturing agent) may also be used, however, the rate of hybridization will be affected. In instances wherein hybridization of deoxyoligonucleotides is concerned, additional exemplary stringent hybridization conditions include washing in 6×SSC 0.05% sodium pyrophosphate at 37° C. (for 14-base oligos), 48° C. (for 17-base oligos), 55° C. (for 20-base oligos), and 60° C. (for 23-base oligos).

Other agents may be included in the hybridization and washing buffers for the purpose of reducing non-specific and/or background hybridization. Examples are 0.1% bovine serum albumin, 0.1% polyvinyl-pyrrolidone, 0.1% sodium pyrophosphate, 0.1% sodium dodecylsulfate, NaDodSO4, (SDS), ficoll, Denhardt's solution, sonicated salmon sperm DNA (or other non-complementary DNA), and dextran sulfate, although other suitable agents can also be used. The concentration and types of these additives can be changed without substantially affecting the stringency of the hybridization conditions. Hybridization experiments are usually carried out at pH 6.8-7.4, however, at typical ionic strength conditions, the rate of hybridization is nearly independent of pH. See Anderson et al., *Nucleic Acid Hybridisation: A Practical Approach*, Ch. 4, IRL Press Limited (Oxford, England). Hybridization conditions can be adjusted by one skilled in the art in order to accommodate these variables and allow DNAs of different sequence relatedness to form hybrids.

The term "muscle specific control element" refers to a nucleotide sequence that regulates expression of a coding sequence that is specific for expression in muscle tissue. These control elements include enhancers and promoters. The invention provides for constructs comprising the muscle specific controls element MCKH7 promoter, the MCK promoter and the MCK enhancer.

In one aspect, the invention provides for a rAAV vector wherein the muscle specific control element is a human skeletal actin gene element, cardiac actin gene element, myocyte-specific enhancer binding factor mef, muscle creatine kinase (MCK), truncated MCK (tMCK), myosin heavy chain (MHC), hybrid α-myosin heavy chain enhancer-/MCK enhancer-promoter (MHCK7), C5-12, murine creatine kinase enhancer element, skeletal fast-twitch troponin c gene element, slow-twitch cardiac troponin c gene element, the slow-twitch troponin i gene element, hypoxia-inducible nuclear factors, steroid-inducible element or glucocorticoid response element (gre).

For examples, the muscle specific control element is the MHCK7 promoter nucleotide sequence SEQ ID NO: 2 or the muscle specific control element is MCK nucleotide sequence SEQ ID NO: 4. In addition, in any of the rAAV vectors of the invention, the muscle specific control element nucleotide sequence, e.g. MHCK7 or MCK nucleotide sequence, is operably linked to the nucleotide sequence encoding the micro-dystrophin protein. For example, the MHCK7 promoter nucleotide sequence (SEQ ID NO: 2) is operably linked to the human micro-dystrophin coding sequence (SEQ ID NO: 1) as set out in the construct provided in FIG. 1 or FIG. 10 (SEQ ID NO: 3). The MCK promoter (SEQ ID NO: 4) is operably linked to the human micro-dystrophin coding sequence (SEQ ID NO: 1) as set out in the construct provided in FIG. 7 or FIG. 11 (SEQ ID NO: 5). In another aspect, the invention provides for a rAAV vector comprising the nucleotide sequence of SEQ ID NO: 1 and SEQ ID NO: 2. The invention also provides for a rAAV vector comprising the nucleotide sequence of SEQ ID NO: 1 and SEQ ID NO: 4.

In a further aspect, the invention provides for a rAAV vector comprising the nucleotide sequence of SEQ ID NO: 3 or SEQ ID NO: 5. For example, the rAAVrh74.MHCK7.micro-dystrophin vector comprises the nucleotide sequence of SEQ ID NO: 3 and shown in FIG. 10. This rAAV vector comprises the MHCK7 promoter, a chimeric intron sequence, the coding sequence for the human micro-dystrophin gene, polyA, ampicillin resistance and the pGEX plasmid backbone with pBR322 origin or replication.

The invention provides for a recombinant AAV vector comprising the human micro-dystrophin nucleotide sequence of SEQ ID NO: 1 and the MHCK7 promoter nucleotide sequence of SEQ ID NO: 3. This rAAV vector is the AAV serotype AAVrh.74.

The invention also provides for a recombinant AAV vector comprising the pAAV.MHCK7.micro-dystrophin construct nucleotide sequence of SEQ ID NO: 3. This rAAV vector is the AAV serotype AAVrh.74.

The rAAV vectors of the invention may be any AAV serotype, such as the serotype AAVrh.74, AAV1, AAV2, AAV4, AAV5, AAV6, AAV7, AAV8, AAV9, AAV10, AAV11, AAV12 or AAV13.

The invention also provides for pharmaceutical compositions (or sometimes referred to herein as simply "compositions") comprising any of the rAAV vectors of the invention.

In another embodiment, the invention provides for methods of producing a rAAV vector particle comprising culturing a cell that has been transfected with any rAAV vector of the invention and recovering rAAV particles from the supernatant of the transfected cells. The invention also provides for viral particles comprising any of the recombinant AAV vectors of the invention.

The invention provides for methods of treating muscular dystrophy comprising administering a therapeutically effective amount of any of the recombinant AAV vectors of the invention expressing human micro-dystrophin.

The invention provides for methods of treating muscular dystrophy comprising administering a therapeutically effective amount of a recombinant AAV vector comprising the human micro-dystrophin nucleotide sequence of SEQ ID NO: 1 and the MHCK7 promoter nucleotide sequence of SEQ ID NO: 2.

The invention also provides for methods of treating muscular dystrophy comprising administering a therapeutically effective amount of a recombinant AAV vector comprising the pAAV.MHCK7.micro-dystrophin construct nucleotide sequence of SEQ ID NO: 3.

"Fibrosis" refers to the excessive or unregulated deposition of extracellular matrix (ECM) components and abnormal repair processes in tissues upon injury including skeletal muscle, cardiac muscle, liver, lung, kidney, and pancreas. The ECM components that are deposited include fibronectin and collagen, e.g. collagen 1, collagen 2 or collagen 3.

In another embodiment, the invention provides for methods of preventing or reducing fibrosis in a subject in need comprising administering a therapeutically effective amount of the any recombinant AAV vector of the invention a human micro-dystrophin protein targeted to the muscle and enhanced cardiac gene delivery and expression in the heart. For example, any of the rAAV of the invention are administered to subjects suffering from muscular dystrophy to prevent or reducing fibrosis, e.g. the rAAV of the invention expressing a human micro-dystrophin protein administered before fibrosis is observed in the subject. In addition, the rAAV of the invention expressing a human micro-dystrophin gene are administered to a subject at risk of developing fibrosis, such as those suffering or diagnosed with muscular dystrophy, e.g. DMD. The rAAV of the invention are administered to the subject suffering from muscular dystrophy in order to prevent new fibrosis in these subjects or to reduce fibrosis in these subjects.

The invention contemplates administering any of the AAV vectors of the invention before fibrosis is observed in the subject. In addition, the rAAV of the invention are administered to a subject at risk of developing fibrosis, such as those suffering or diagnosed with muscular dystrophy, e.g. DMD. The rAAV of the invention are administered to the subject suffering from muscular dystrophy who already has developed fibrosis in order to prevent new fibrosis in these subjects.

The invention also provides for methods of increasing muscular force and/or muscle mass in a subject suffering from muscular dystrophy comprising administering a therapeutically effective amount of any of the rAAV vector of the invention expressing a human micro-dystrophin gene. These methods may further comprise the step of administering a rAAV expressing micro-dystrophin.

The invention contemplates administering any of the AAV vectors of the invention to patients diagnosed with DMD before fibrosis is observed in the subject or before the muscle force has been reduced or before the muscle mass has been reduced.

The invention also contemplates administering any of the rAAV of the invention to a subject suffering from muscular dystrophy who already has developed fibrosis, in order to prevent new fibrosis in these subjects. The invention also provides for administering any of the rAAV of the invention to the patient suffering from muscular dystrophy who already has reduced muscle force or has reduced muscle mass in order to protect the muscle from further injury.

In any of the methods of the invention, the subject may be suffering from muscular dystrophy such as DMD or any other dystrophin-associated muscular dystrophy.

In another aspect, the rAAV vectors expressing the micro-dystrophin protein comprises the coding sequence of the micro-dystrophin gene operably linked to a muscle-specific control element other than MHCK7 or MCK. For example, the muscle-specific control element is human skeletal actin gene element, cardiac actin gene element, myocyte-specific enhancer binding factor MEF, tMCK (truncated MCK), myosin heavy chain (MHC), C5-12 (synthetic promoter), murine creatine kinase enhancer element, skeletal fast-twitch troponin C gene element, slow-twitch cardiac troponin C gene element, the slow-twitch troponin I gene element, hypoxia-inducible nuclear factors, steroid-inducible element or glucocorticoid response element (GRE).

In any of the methods of the invention, the rAAV vector or composition is administered by intramuscular injection or intravenous injection.

In addition, in any of the methods of the invention, the rAAV vector or composition is administered systemically. For examples, the rAAV vector or composition is parentally administration by injection, infusion or implantation.

In another embodiment, the invention provides for composition comprising any of the rAAV vectors of the invention for reducing fibrosis in a subject in need.

In addition, the invention provides for compositions comprising any of the recombinant AAV vectors of the invention for preventing fibrosis in a patient suffering from muscular dystrophy.

The invention provides for compositions comprising any of the recombinant AAV vectors of the invention for treating muscular dystrophy.

The invention provides for compositions comprising a recombinant AAV vector comprising the human micro-dystrophin nucleotide sequence of SEQ ID NO: 1 and the MHCK7 promoter sequence of SEQ ID NO: 2 for treatment of muscular dystrophy.

The invention provides for composition comprising a recombinant AAV vector comprising the pAAV.MHCK7.micro-dystrophin construct nucleotide sequence of SEQ ID NO: 3 for treatment of muscular dystrophy.

The invention also provides for compositions comprising any of the rAAV vectors of the invention for increasing muscular force and/or muscle mass in a subject suffering from muscular dystrophy. In a further embodiment, the invention provides for compositions comprising any of the rAAV vectors of the invention for treatment of muscular dystrophy.

The compositions of the invention are formulated for intramuscular injection or intravenous injection. The composition of the invention is also formulated for systemic administration, such as parentally administration by injection, infusion or implantation.

In addition, any of the compositions are formulated for administration to a subject suffering from muscular dystrophy such as DMD or any other dystrophin associated muscular dystrophy.

In a further embodiment, the invention provides for use of any of the rAAV vectors of the invention for preparation of a medicament for reducing fibrosis in a subject in need. For example, the subject is in need suffering from muscular dystrophy, such as DMD or any other dystrophin associated muscular dystrophy.

In another embodiment, the invention provides for provides for use of any of the rAAV vectors of the invention for the preparation of a medicament for preventing fibrosis in a subject suffering from muscular dystrophy.

In addition, the invention provides for use of the recombinant AAV vectors of the invention for the preparation of a medicament for the increasing muscular strength and/or muscle mass in a subject suffering from muscular dystrophy.

The invention also provides for use of the rAAV vectors of the invention for the preparation of a medicament for treatment of muscular dystrophy.

The invention provides for use of a recombinant AAV vector comprising the human micro-dystrophin nucleotide sequence of SEQ ID NO: 1 and the MHCK7 promoter nucleotide sequence of SEQ ID NO: 2 for preparation of a medicament for the treatment of muscular dystrophy.

The invention provides for use of a recombinant AAV vector comprising the pAAV.MHCK7.micro-dystrophin construct nucleotide sequence of SEQ ID NO: 3 for treatment of muscular dystrophy.

In any of the uses of the invention, the medicament is formulated for intramuscular injection or intravenous injection. In addition, in any of the uses of the invention, the medicament is formulated for systemic administration such as parental administration by injection, infusion or implantation.

Any of the medicaments may be prepared for administration to a subject suffering from muscular dystrophy such as DMD or any other dystrophin associated muscular dystrophy.

The invention also provides for combination therapy or co-therapies comprising administering a recombinant AAV vector expressing micro-dystrophin and administering a recombinant AAV vector expressing miR-29 and expression of miR-29 is controlled by a muscle-specific control element nucleotide sequence.

In one embodiment, the invention provides for methods of treating muscular dystrophy comprising administering i) a therapeutically effective amount of a recombinant AAV vector expressing micro-dystrophin and expression of micro-dystrophin is controlled by a muscle specific control element nucleotide sequence and ii) a therapeutically effective amount of a recombinant AAV vector expressing miR-29c and expression of miR-29c is controlled by a muscle-specific control element nucleotide sequence.

In another embodiment, the invention provides for methods of increasing muscular force or muscle mass in a subject suffering from muscular dystrophy comprising administering i) a therapeutically effective amount of a recombinant AAV vector expressing micro-dystrophin and expression of micro-dystrophin is controlled by a muscle specific control element nucleotide sequence and ii) a therapeutically effective amount of recombinant AAV vector expressing miR-29c and expression of miR-29c is controlled by a muscle-specific control element nucleotide sequence.

In a further embodiment, the invention provides for methods of reducing or preventing fibrosis in a subject suffering from muscular dystrophy comprising administering i) a therapeutically effective amount of a recombinant AAV vector expressing micro-dystrophin and expression of micro-dystrophin is controlled by a muscle specific control element nucleotide sequence and ii) a therapeutically effective amount of recombinant AAV vector expressing miR-29c and expression of miR-29c is controlled by a muscle-specific control element nucleotide sequence.

The invention also provides for compositions for treating muscular dystrophy comprising i) a therapeutically effective amount of a recombinant AAV vector expressing micro-dystrophin and expression of micro-dystrophin is controlled by a muscle specific control element nucleotide sequence and ii) a therapeutically effective amount of a recombinant AAV vector expressing miR-29c and expression of miR-29c is controlled by a muscle-specific control element nucleotide sequence.

In another embodiment, the invention provides for compositions for increasing muscular force or muscle mass in a subject suffering from muscular dystrophy comprising administering i) a therapeutically effective amount of a recombinant AAV vector expressing micro-dystrophin and expression of micro-dystrophin is controlled by a muscle specific control element nucleotide sequence and ii) a therapeutically effective amount of recombinant AAV vector expressing miR-29c and expression of miR-29c is controlled by a muscle-specific control element nucleotide sequence.

In a further embodiment, the invention provides for compositions for reducing or preventing fibrosis in a subject suffering from muscular dystrophy comprising administering i) a therapeutically effective amount of i) a recombinant AAV vector expressing micro-dystrophin and expression of micro-dystrophin is controlled by a muscle specific control element nucleotide sequence and ii) a therapeutically effective amount of recombinant AAV vector expressing miR-29c and expression of miR-29c is controlled by a muscle-specific control element nucleotide sequence.

The invention also provides for use of i) a therapeutically effective amount of a recombinant AAV vector expressing micro-dystrophin wherein the expression of micro-dystrophin is controlled by a muscle specific control element nucleotide sequence and ii) a therapeutically effective amount of recombinant AAV vector expressing miR-29c wherein the expression of miR-29c is controlled by a muscle-specific control element nucleotide sequence for preparation of a medicament for the treatment of muscular dystrophy.

In another embodiment, the invention provides for use of i) a therapeutically effective amount of a recombinant AAV vector expressing micro-dystrophin wherein the expression of micro-dystrophin is controlled by a muscle specific control element nucleotide sequence and ii) a therapeutically effective amount of a recombinant AAV vector expressing miR-29c wherein the expression of miR-29c is controlled by a muscle-specific control element nucleotide sequence for the preparation of a medicament for increasing muscular force or muscle mass in a subject suffering from muscular dystrophy.

In a further embodiment, the invention provides for use of i) a therapeutically effective amount of a recombinant AAV vector expressing micro-dystrophin wherein the expression of micro-dystrophin is controlled by a muscle specific control element nucleotide sequence and ii) a therapeutically effective amount of a recombinant AAV vector expressing miR-29c wherein the expression of miR-29c is controlled by a muscle-specific control element nucleotide sequence for the preparation of a medicament for reducing or preventing fibrosis in a subject suffering from muscular dystrophy.

In any of the combination or co-therapy methods, compositions or uses of the invention, the muscular dystrophy is Duchenne muscular dystrophy.

In any of the combination or co-therapy methods, compositions or uses of the invention, the nucleotide sequence encoding the micro-dystrophin protein comprises a) a nucleotide sequence that is at least 85% identical to the nucleotide sequence SEQ ID NO: 1 and encodes a functional micro-dystrophin protein, or b) the nucleotide sequences of SEQ ID NO: 1.

In addition, in any of the combination or co-therapy methods, compositions or uses of the invention, the recombinant AAV vector expressing miR-29c comprises: a) the nucleotide sequences of SEQ ID NO: 8 and SEQ ID NO: 9, b) the nucleotide sequence of SEQ ID NO: 7, or c) the nucleotide sequence of SEQ ID NO: 6.

In any of the combination or co-therapy methods, compositions or uses of the invention, at least one of the muscle specific control element is human skeletal actin gene element, cardiac actin gene element, myocyte-specific enhancer binding factor mef, muscle creatine kinase (MCK), truncated MCK (tMCK), myosin heavy chain (MHC), hybrid α-myosin heavy chain enhancer-/MCK enhancer-promoter (MHCK7), C5-12, murine creatine kinase enhancer element, skeletal fast-twitch troponin c gene element, slow-twitch cardiac troponin c gene element, the slow-twitch troponin i gene element, hypoxia-inducible nuclear factors, steroid-inducible element or glucocorticoid response element (gre). For example, the muscle specific control element controlling expression of micro-dystrophin comprises SEQ ID NO: 2 (MHCK7) and/or the muscle specific control element controlling expression of miR-29c comprises SEQ ID NO: 10 (CMV).

In exemplary combination or co-therapy methods, compositions or uses, the AAV vector expressing micro-dystrophin comprises i) the nucleotide sequences of SEQ ID NO: 1 (micro-dys) and ii) the nucleotide sequence of SEQ ID NO: 2 (MHCK7) or the AAV vector expressing micro-dystrophin comprises the nucleotide sequence of SEQ ID NO: 3.

In exemplary combination or co-therapy methods, compositions or uses, the AAV vector expressing miR-29c comprises i) the nucleotide sequence of SEQ ID NO: 8 or SEQ ID NO: 9 and ii) the nucleotide sequence of SEQ ID NO: 10 (CMV) or the AAV vector expressing miR-29c comprises the nucleotide sequence of SEQ ID NO: 6.

In another exemplary combination or co-therapy methods, compositions or uses, the AAV vector expressing micro-dystrophin comprises i) the nucleotide sequences of SEQ ID NO: 1 (micro-dys) and ii) the nucleotide sequence of SEQ 2 (MHCK7), and wherein the AAV vector expressing miR-29c comprises i) the nucleotide sequence of SEQ ID NO: 8 or SEQ ID NO: 9 and ii) the nucleotide sequence of SEQ ID NO: 10 (CMV).

In further combination or co-therapy methods, compositions or uses, the AAV vector expressing micro-dystrophin comprises the nucleotide sequence of SEQ ID NO: 3 and the AAV vector expressing miR-29c comprises the nucleotide sequence of SEQ ID NO: 6.

In any of the combination or co-therapy methods, compositions or uses of the invention, at least one of the recombinant AAV vectors is the serotype AAVrh.74, AAV1, AAV2, AAV4, AAV5, AAV6, AAV7, AAV8, AAV9, AAV10, AAV11, AAV12 or AAV13.

In any of the combination or co-therapy methods, compositions or uses of the invention, least one of the recombinant AAV vectors, the composition or the medicament is administered by intramuscular injection or intravenous injection.

In any of the combination or co-therapy methods, compositions or uses of the invention, at least one of the recombinant AAV vectors or the composition or the medicament is administered systemically.

In any of the combination or co-therapy methods, compositions or uses of the invention, at least one of the recombinant AAV vectors, compositions or medicaments is parenterally administered by injection, infusion or implantation.

BRIEF DESCRIPTION OF DRAWING

FIGS. 3A-3C provide skeletal muscle force measurements and quantification of micro-dystrophin expression following intramuscular injection of AAVrh74.MHCK7 construct. (A) The tibialis anterior muscle of mdx mice was injected with $1\times10^{11}$ vg (n=5) with AAVrh74.MHCK7 construct. Six weeks later the tibialis anterior muscles were harvested and subjected to in vivo force measurements. The dosed cohort had significantly greater force production than untreated mdx controls.

(FIG. 6C) shows the total number of fibers is unchanged with treatment. The amount of creatine kinase is provided in (D) showing improvement at high dose. Independent t-tests were used to locate differences (p<0.05); Data are reported as means±SEM.

FIG. 10 provides the nucleic acid sequence (SEQ ID NO: 3 rAAVrh74.MHCK7. micro-dystrophin).

FIG. 11 provide the nucleic acid sequence (SEQ ID NO: 5) rAAVrh74.MCK.micro-dystrophin.

FIG. 12 provide a schematic of rAAV vector scAAVrh.74.CMV.miR29c and the nucleotide sequence of the miR-29c in a natural miR-30 backbone and the nucleotide sequence of the predicted hairpin structure.

FIGS. 13A-13C demonstrate that early combination therapy restores force and protects against contraction-induced damage. Measurement of absolute (A) and normalized specific force (B) following tetanic contraction demonstrated increased force with combination therapy compared to untreated mdx/utrn$^{+/-}$ muscle and micro-dystrophin therapy alone (*p<0.05). One-way ANOVA (C) Muscles were then assessed for loss of force following repetitive eccentric contractions. Mice co-treated with miR-29c/micro-dystrophin and micro-dystrophin alone showed a protection from loss of force compared with untreated mdx/utrn$^{+/-}$ muscles (red). Two-way ANOVA. (p<0.01, **P<0.0001). All data represent mean±SEM (D) Sirius Red stain Representative images demonstrating muscle fibers (green) and collagen content (red).

DETAILED DESCRIPTION

Figure 1:
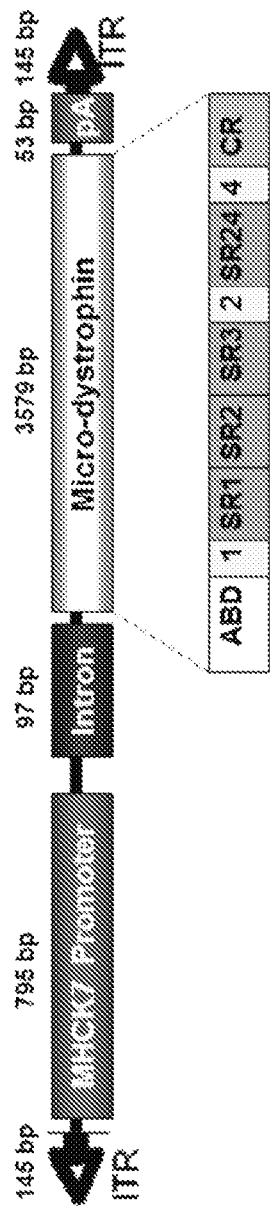
FIG. 1 illustrates the pAAV.MHCK7.micro-dystrophin construct. In this construct, the cDNA expression cassette is flanked by AAV2 inverted terminal repeat sequences (ITR). The construct is characterized by an in-frame rod deletion (R4-R23), while hinges 1, 2 and 4 ($H_1$, $H_2$ and $H_3$) and the cysteine rich domain remain producing a 138 kDa protein. The expression of the micro-dystrophin protein (3579 bp) is guided by a MHCK7 promoter (795 bp). The intron and 5' UTR are derived from plasmid pCMVβ (Clontech). The micro-dystrophin cassette had a consensus Kozak immediately in front of the ATG start and a small 53 bp synthetic polyA signal for mRNA termination. The human micro-dystrophin cassette contained the (R4-R23/Δ71-78) domains as previously described by Harper et al. (*Nature Medicine* 8, 253-261 (2002)).

The present invention provides for gene therapy vectors, e.g. rAAV vectors, overexpressing human micro-dystrophin and methods of reducing and preventing fibrosis in muscular dystrophy patients. The present invention also provides for co-therapy (combination) gene therapy methods which comprise administering a gene therapy vector expressing miR-29 in combination with a gene therapy vector expressing micro-dystrophin that is deleted in DMD patients.

Muscle biopsies taken at the earliest age of diagnosis of DMD reveal prominent connective tissue proliferation. Muscle fibrosis is deleterious in multiple ways. It reduces normal transit of endomysial nutrients through connective tissue barriers, reduces the blood flow and deprives muscle of vascular-derived nutritional constituents, and functionally contributes to early loss of ambulation through limb contractures. Over time, treatment challenges multiply as a result of marked fibrosis in muscle. This can be observed in muscle biopsies comparing connective tissue proliferation at successive time points. The process continues to exacerbate leading to loss of ambulation and accelerating out of control, especially in wheelchair-dependent patients.

Without early treatment a parallel approach to reduce fibrosis it is unlikely that the benefits of exon skipping, stop-codon read-through, or gene replacement therapies can ever be fully achieved. Even small molecules or protein replacement strategies are likely to fail without an approach to reduce muscle fibrosis. Previous work in aged mdx mice with existing fibrosis treated with AAV.micro-dystrophin demonstrated that we could not achieve full functional restoration (Liu, M., et al., Mol Ther 11, 245-256 (2005)). It is also known that progression of DMD cardiomyopathy is accompanied by scarring and fibrosis in the ventricular wall. Micro-RNA delivery is particularly innovative because of lack of immune barriers and relative ease of delivery. Micro-RNAs are small (~200 bp) and can therefore be packaged in AAV along with a therapeutic cassette to correct or bypass the genetic defect.

As used herein, the term "AAV" is a standard abbreviation for adeno-associated virus. Adeno-associated virus is a single-stranded DNA parvovirus that grows only in cells in which certain functions are provided by a co-infecting helper virus. There are currently thirteen serotypes of AAV that have been characterized. General information and reviews of AAV can be found in, for example, Carter, 1989, Handbook of Parvoviruses, Vol. 1, pp. 169-228, and Berns, 1990, Virology, pp. 1743-1764, Raven Press, (New York). However, it is fully expected that these same principles will be applicable to additional AAV serotypes since it is well known that the various serotypes are quite closely related, both structurally and functionally, even at the genetic level. (See, for example, Blacklowe, 1988, pp. 165-174 of Parvoviruses and Human Disease, J. R. Pattison, ed.; and Rose, Comprehensive Virology 3:1-61 (1974)). For example, all AAV serotypes apparently exhibit very similar replication properties mediated by homologous rep genes; and all bear three related capsid proteins such as those expressed in AAV2. The degree of relatedness is further suggested by heteroduplex analysis which reveals extensive cross-hybridization between serotypes along the length of the genome; and the presence of analogous self-annealing segments at the termini that correspond to "inverted terminal repeat sequences" (ITRs). The similar infectivity patterns also suggest that the replication functions in each serotype are under similar regulatory control.

An "AAV vector" as used herein refers to a vector comprising one or more polynucleotides of interest (or transgenes) that are flanked by AAV terminal repeat sequences (ITRs). Such AAV vectors can be replicated and packaged into infectious viral particles when present in a host cell that has been transfected with a vector encoding and expressing rep and cap gene products.

An "AAV virion" or "AAV viral particle" or "AAV vector particle" refers to a viral particle composed of at least one AAV capsid protein and an encapsidated polynucleotide AAV vector. If the particle comprises a heterologous polynucleotide (i.e. a polynucleotide other than a wild-type AAV genome such as a transgene to be delivered to a mammalian cell), it is typically referred to as an "AAV vector particle" or simply an "AAV vector". Thus, production of AAV vector particle necessarily includes production of AAV vector, as such a vector is contained within an AAV vector particle.
AAV Recombinant AAV genomes of the invention comprise nucleic acid molecule of the invention and one or more AAV ITRs flanking a nucleic acid molecule. AAV DNA in the rAAV genomes may be from any AAV serotype for which a recombinant virus can be derived including, but not limited to, AAV serotypes AAVrh.74, AAV-1, AAV-2, AAV-3, AAV-4, AAV-5, AAV-6, AAV-7, AAV-8, AAV-9, AAV-10, AAV-11, AAV-12 and AAV-13. Production of pseudotyped rAAV is disclosed in, for example, WO 01/83692. Other types of rAAV variants, for example rAAV with capsid mutations, are also contemplated. See, for example, Marsic et al., *Molecular Therapy*, 22(11): 1900-1909 (2014). As noted in the Background section above, the nucleotide sequences of the genomes of various AAV serotypes are known in the art. To promote skeletal muscle specific expression, AAV1, AAV6, AAV8 or AAVrh.74 may be used.

DNA plasmids of the invention comprise rAAV genomes of the invention. The DNA plasmids are transferred to cells permissible for infection with a helper virus of AAV (e.g., adenovirus, E1-deleted adenovirus or herpesvirus) for assembly of the rAAV genome into infectious viral particles. Techniques to produce rAAV particles, in which an AAV genome to be packaged, rep and cap genes, and helper virus functions are provided to a cell, are standard in the art. Production of rAAV requires that the following components are present within a single cell (denoted herein as a packaging cell): a rAAV genome, AAV rep and cap genes separate from (i.e., not in) the rAAV genome, and helper virus functions. The AAV rep and cap genes may be from any AAV serotype for which recombinant virus can be derived and may be from a different AAV serotype than the rAAV genome ITRs, including, but not limited to, AAV serotypes AAV-1, AAV-2, AAV-3, AAV-4, AAV-5, AAV-6, AAV-7, AAVrh.74, AAV-8, AAV-9, AAV-10, AAV-11, AAV-12 and AAV-13. Production of pseudotyped rAAV is disclosed in, for example, WO 01/83692 which is incorporated by reference herein in its entirety.

A method of generating a packaging cell is to create a cell line that stably expresses all the necessary components for AAV particle production. For example, a plasmid (or multiple plasmids) comprising a rAAV genome lacking AAV rep and cap genes, AAV rep and cap genes separate from the rAAV genome, and a selectable marker, such as a neomycin resistance gene, are integrated into the genome of a cell. AAV genomes have been introduced into bacterial plasmids by procedures such as GC tailing (Samulski et al., 1982, *Proc. Natl. Acad. S6. USA*, 79:2077-2081), addition of synthetic linkers containing restriction endonuclease cleavage sites (Laughlin et al., 1983, Gene, 23:65-73) or by direct, blunt-end ligation (Senapathy & Carter, 1984, J. Biol. Chem., 259:4661-4666). The packaging cell line is then infected with a helper virus such as adenovirus. The advantages of this method are that the cells are selectable and are suitable for large-scale production of rAAV. Other examples of suitable methods employ adenovirus or baculovirus rather than plasmids to introduce rAAV genomes and/or rep and cap genes into packaging cells.

General principles of rAAV production are reviewed in, for example, Carter, 1992, Current Opinions in Biotechnology, 1533-539; and Muzyczka, 1992, Curr. Topics in Microbial. and Immunol., 158:97-129). Various approaches are described in Ratschin et al., *Mol. Cell. Biol.* 4:2072 (1984); Hermonat et al., *Proc. Natl. Acad. Sci. USA*, 81:6466 (1984); Tratschin et al., *Mol. Cell. Biol.* 5:3251 (1985); McLaughlin et al., *J. Virol.*, 62:1963 (1988); and Lebkowski et al., *Mol. Cell. Biol.*, 7:349 (1988). Samulski et al., J. Virol., 63:3822-3828 (1989); U.S. Pat. No. 5,173,414; WO 95/13365 and corresponding U.S. Pat. No. 5,658,776; WO 95/13392; WO 96/17947; PCT/US98/18600; WO 97/09441 (PCT/US96/14423); WO 97/08298 (PCT/US96/13872); WO 97/21825 (PCT/US96/20777); WO 97/06243 (PCT/FR96/01064); WO 99/11764; Perrin et al. *Vaccine* 13:1244-1250 (1995); Paul et al. *Human Gene Therapy* 4:609-615 (1993); Clark et al. *Gene Therapy* 3:1124-1132 (1996); U.S. Pat. Nos. 5,786,211; 5,871,982; and U.S. Pat. No. 6,258,595. The foregoing documents are hereby incorporated by reference in their entirety herein, with particular emphasis on those sections of the documents relating to rAAV production.

The invention thus provides packaging cells that produce infectious rAAV. In one embodiment packaging cells may be stably transformed cancer cells such as HeLa cells, 293 cells and PerC.6 cells (a cognate 293 line). In another embodiment, packaging cells are cells that are not transformed cancer cells, such as low passage 293 cells (human fetal kidney cells transformed with E1 of adenovirus), MRC-5 cells (human fetal fibroblasts), WI-38 cells (human fetal fibroblasts), Vero cells (monkey kidney cells) and FRhL-2 cells (rhesus fetal lung cells).

Recombinant AAV (i.e., infectious encapsidated rAAV particles) of the invention comprises a rAAV genome. In exemplary embodiments, the genomes of both rAAV lack AAV rep and cap DNA, that is, there is no AAV rep or cap DNA between the ITRs of the genomes. Examples of rAAV that may be constructed to comprise the nucleic acid molecules of the invention are set out in International Patent Application No. PCT/US2012/047999 (WO 2013/016352) incorporated by reference herein in its entirety.

The rAAV may be purified by methods standard in the art such as by column chromatography or cesium chloride gradients. Methods for purifying rAAV vectors from helper virus are known in the art and include methods disclosed in, for example, Clark et al., *Hum. Gene Ther.*, 10(6): 1031-1039 (1999); Schenpp and Clark, *Methods Mol. Med.*, 69 427-443 (2002); U.S. Pat. No. 6,566,118 and WO 98/09657.

In another embodiment, the invention contemplates compositions comprising rAAV of the present invention. Compositions of the invention comprise rAAV and a pharmaceutically acceptable carrier. The compositions may also comprise other ingredients such as diluents and adjuvants. Acceptable carriers, diluents and adjuvants are nontoxic to recipients and are preferably inert at the dosages and concentrations employed and include buffers and surfactants such as pluronics.

Titers of rAAV to be administered in methods of the invention will vary depending, for example, on the particular rAAV, the mode of administration, the treatment goal, the individual, and the cell type(s) being targeted, and may be determined by methods standard in the art. Titers of rAAV may range from about $1 \times 10^6$, about $1 \times 10^7$, about $1 \times 10^8$, about $1 \times 10^9$, about $1 \times 10^{10}$, about $1 \times 10^{11}$, about $1 \times 10^{12}$, about $1 \times 10^{13}$ to about $1 \times 10^{14}$ or more DNase resistant particles (DRP) per ml. Dosages may also be expressed in units of viral genomes (vg).

Methods of transducing a target cell with rAAV, in vivo or in vitro, are contemplated by the invention. The in vivo methods comprise the step of administering an effective dose, or effective multiple doses, of a composition comprising a rAAV of the invention to an animal (including a human being) in need thereof. If the dose is administered prior to development of a disorder/disease, the administration is prophylactic. If the dose is administered after the development of a disorder/disease, the administration is therapeutic. In embodiments of the invention, an effective dose is a dose that alleviates (eliminates or reduces) at least one symptom associated with the disorder/disease state being treated, that slows or prevents progression to a disorder/disease state, that slows or prevents progression of a disorder/disease state, that diminishes the extent of disease, that results in remission (partial or total) of disease, and/or that prolongs survival. An example of a disease contemplated for prevention or treatment with methods of the invention is FSHD.

Combination therapies or co-therapies are also contemplated by the invention. Combination as used herein includes both simultaneous treatment and sequential treatments. Combinations of methods of the invention with standard medical treatments (e.g., corticosteroids) are specifically contemplated, as are combinations with novel therapies.

Administration of an effective dose of the compositions may be by routes standard in the art including, but not limited to, intramuscular, parenteral, intravenous, oral, buccal, nasal, pulmonary, intracranial, intraosseous, intraocular, rectal, or vaginal. Route(s) of administration and serotype(s) of AAV components of the rAAV (in particular, the AAV ITRs and capsid protein) of the invention may be chosen and/or matched by those skilled in the art taking into account the infection and/or disease state being treated and the target cells/tissue(s) that are to express the micro-dystrophin protein.

The invention provides for local administration and systemic administration of an effective dose of rAAV and compositions of the invention. For example, systemic administration is administration into the circulatory system so that the entire body is affected. Systemic administration includes enteral administration such as absorption through the gastrointestinal tract and parental administration through injection, infusion or implantation.

In particular, actual administration of rAAV of the present invention may be accomplished by using any physical method that will transport the rAAV recombinant vector into the target tissue of an animal. Administration according to the invention includes, but is not limited to, injection into muscle, the bloodstream and/or directly into the liver. Simply resuspending a rAAV in phosphate buffered saline has been demonstrated to be sufficient to provide a vehicle useful for muscle tissue expression, and there are no known restrictions on the carriers or other components that can be co-administered with the rAAV (although compositions that degrade DNA should be avoided in the normal manner with rAAV). Capsid proteins of a rAAV may be modified so that the rAAV is targeted to a particular target tissue of interest such as muscle. See, for example, WO 02/053703, the disclosure of which is incorporated by reference herein. Pharmaceutical compositions can be prepared as injectable formulations or as topical formulations to be delivered to the muscles by transdermal transport. Numerous formulations for both intramuscular injection and transdermal transport have been previously developed and can be used in the practice of the invention. The rAAV can be used with any pharmaceutically acceptable carrier for ease of administration and handling.

The dose of rAAV to be administered in methods disclosed herein will vary depending, for example, on the particular rAAV, the mode of administration, the treatment goal, the individual, and the cell type(s) being targeted, and may be determined by methods standard in the art. Titers of each rAAV administered may range from about $1 \times 10^6$, about $1 \times 10^7$, about $1 \times 10^8$, about $1 \times 10^9$, about $1 \times 10^{10}$, about $1 \times 10^{11}$, about $1 \times 10^{12}$, about $1 \times 10^{13}$, about $1 \times 10^{14}$, or to about $1 \times 10^{15}$ or more DNase resistant particles (DRP) per ml. Dosages may also be expressed in units of viral genomes (vg) (i.e., $1 \times 10^7$ vg, $1 \times 10^8$ vg, $1 \times 10^9$ vg, $1 \times 10^{10}$ vg, $1 \times 10^{11}$ vg, $1 \times 10^{12}$ vg, $1 \times 10^{13}$ vg, $1 \times 10^{14}$ vg, $1 \times 10^{15}$ respectively). Dosages may also be expressed in units of viral genomes (vg) per kilogram (kg) of bodyweight (i.e., $1 \times 10^{10}$ vg/kg, $1 \times 10^{11}$ vg/kg, $1 \times 10^{12}$ vg/kg, $1 \times 10^{13}$ vg/kg, $1 \times 10^{14}$ vg/kg, $1 \times 10^{15}$ vg/kg respectively). Methods for titering AAV are described in Clark et al., *Hum. Gene Ther.*, 10: 1031-1039 (1999).

In particular, actual administration of rAAV of the present invention may be accomplished by using any physical method that will transport the rAAV recombinant vector into the target tissue of an animal. Administration according to the invention includes, but is not limited to, injection into muscle, the bloodstream and/or directly into the liver. Simply resuspending a rAAV in phosphate buffered saline has been demonstrated to be sufficient to provide a vehicle useful for muscle tissue expression, and there are no known restrictions on the carriers or other components that can be co-administered with the rAAV (although compositions that degrade DNA should be avoided in the normal manner with rAAV). Capsid proteins of a rAAV may be modified so that the rAAV is targeted to a particular target tissue of interest such as muscle. See, for example, WO 02/053703, the disclosure of which is incorporated by reference herein. Pharmaceutical compositions can be prepared as injectable formulations or as topical formulations to be delivered to the muscles by transdermal transport. Numerous formulations for both intramuscular injection and transdermal transport have been previously developed and can be used in the practice of the invention. The rAAV can be used with any pharmaceutically acceptable carrier for ease of administration and handling.

For purposes of intramuscular injection, solutions in an adjuvant such as sesame or peanut oil or in aqueous propylene glycol can be employed, as well as sterile aqueous solutions. Such aqueous solutions can be buffered, if desired, and the liquid diluent first rendered isotonic with saline or glucose. Solutions of rAAV as a free acid (DNA contains acidic phosphate groups) or a pharmacologically acceptable salt can be prepared in water suitably mixed with a surfactant such as hydroxpropylcellulose. A dispersion of rAAV can also be prepared in glycerol, liquid polyethylene glycols and mixtures thereof and in oils. Under ordinary conditions of storage and use, these preparations contain a preservative to prevent the growth of microorganisms. In this connection, the sterile aqueous media employed are all readily obtainable by standard techniques well-known to those skilled in the art.

The pharmaceutical carriers, diluents or excipients suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating actions of microorganisms such as bacteria and fungi. The carrier can be a solvent or dispersion medium containing, for example, water, ethanol, polyol (for example, glycerol, propylene glycol, liquid polyethylene glycol and the like), suitable mixtures thereof, and vegetable oils. The proper fluidity can be maintained, for example, by the use of a coating such as lecithin, by the maintenance of the required particle size in the case of a dispersion and by the use of surfactants. The prevention of the action of microorganisms can be brought about by various antibacterial and antifungal agents, for example, parabens, chlorobutanol, phenol, sorbic acid, thimerosal and the like. In many cases it will be preferable to include isotonic agents, for example, sugars or sodium chloride. Prolonged absorption of the injectable compositions can be brought about by use of agents delaying absorption, for example, aluminum monostearate and gelatin.

Sterile injectable solutions are prepared by incorporating rAAV in the required amount in the appropriate solvent with various other ingredients enumerated above, as required, followed by filter sterilization. Generally, dispersions are prepared by incorporating the sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze drying technique that yield a powder of the active ingredient plus any additional desired ingredient from the previously sterile-filtered solution thereof.

Transduction with rAAV may also be carried out in vitro. In one embodiment, desired target muscle cells are removed from the subject, transduced with rAAV and reintroduced into the subject. Alternatively, syngeneic or xenogeneic muscle cells can be used where those cells will not generate an inappropriate immune response in the subject.

Suitable methods for the transduction and reintroduction of transduced cells into a subject are known in the art. In one embodiment, cells can be transduced in vitro by combining rAAV with muscle cells, e.g., in appropriate media, and screening for those cells harboring the DNA of interest using conventional techniques such as Southern blots and/or PCR, or by using selectable markers. Transduced cells can then be formulated into pharmaceutical compositions, and the composition introduced into the subject by various techniques, such as by intramuscular, intravenous, subcutaneous and intraperitoneal injection, or by injection into smooth and cardiac muscle, using e.g., a catheter.

Transduction of cells with rAAV of the invention results in sustained expression of the micro-dystrophin protein. The present invention thus provides methods of administering/delivering rAAV which express of micro-dystrophin protein to an animal, preferably a human being. These methods include transducing tissues (including, but not limited to, tissues such as muscle, organs such as liver and brain, and glands such as salivary glands) with one or more rAAV of the present invention. Transduction may be carried out with gene cassettes comprising tissue specific control elements. For example, one embodiment of the invention provides methods of transducing muscle cells and muscle tissues directed by muscle specific control elements, including, but not limited to, those derived from the actin and myosin gene families, such as from the myoD gene family (See Weintraub et al., *Science*, 251: 761-766 (1991)), the myocyte-specific enhancer binding factor MEF-2 (Cserjesi and Olson, *Mol Cell Biol* 11: 4854-4862 (1991)), control elements derived from the human skeletal actin gene (Muscat et al., *Mol Cell Biol*, 7: 4089-4099 (1987)), the cardiac actin gene, muscle creatine kinase sequence elements (See Johnson et al., *Mol Cell Biol*, 9:3393-3399 (1989)) and the murine creatine kinase enhancer (mCK) element, control elements derived from the skeletal fast-twitch troponin C gene, the slow-twitch cardiac troponin C gene and the slow-twitch troponin I gene: hypoxia-inducible nuclear factors (Semenza et al., *Proc Natl Acad Sci USA*, 88: 5680-5684 (1991)), steroid-inducible elements and promoters including the glucocorticoid response element (GRE) (See Mader and White, *Proc. Natl. Acad. Sci. USA* 90: 5603-5607 (1993)), and other control elements.

Muscle tissue is an attractive target for in vivo DNA delivery, because it is not a vital organ and is easy to access. The invention contemplates sustained expression of micro-dystrophin from transduced myofibers.

By "muscle cell" or "muscle tissue" is meant a cell or group of cells derived from muscle of any kind (for example, skeletal muscle and smooth muscle, e.g. from the digestive tract, urinary bladder, blood vessels or cardiac tissue). Such muscle cells may be differentiated or undifferentiated, such as myoblasts, myocytes, myotubes, cardiomyocytes and cardiomyoblasts.

The term "transduction" is used to refer to the administration/delivery of the coding region of the micro-dystrophin to a recipient cell either in vivo or in vitro, via a replication-deficient rAAV of the invention resulting in expression of micro-dystrophin by the recipient cell.

Thus, the invention provides methods of administering an effective dose (or doses, administered essentially simultaneously or doses given at intervals) of rAAV that encode micro-dystrophin to a patient in need thereof.

EXAMPLES

Example 1

Generation of the pAAV.MHCK7.Micro-Dystrophin Construct

The pAAV.MHCK7.micro-dystrophin plasmid contains a human micro-dystrophin cDNA expression cassette flanked by AAV2 inverted terminal repeat sequences (ITR) (see FIG. 1). The micro-dys construct was characterized by an in-frame rod deletion (R4-R23), while hinges 1, 2 and 4 and cysteine rich domain remain producing a 138 kDa protein. The expression of the micro-dystrophin protein (3579 bp) was guided by a MHCK7 promoter (795 bp). The intron and 5' UTR are derived from plasmid pCMVß (Clontech). The micro-dystrophin cassette had a consensus Kozak immediately in front of the ATG start and a small 53 bp synthetic polyA signal for mRNA termination. The human micro-dystrophin cassette contained the (R4-R23/Δ71-78) domains as previously described by Harper et al. (*Nature Medicine* 8, 253-261 (2002)). The complementary DNA was codon optimized for human usage and synthesized by GenScript (Piscataway, N.J.) (*Mol Ther* 18, 109-117 (2010)). The only viral sequences included in this vector were the inverted terminal repeats of AAV2, which are required for both viral DNA replication and packaging. The micro-dystrophin cassette has a small 53 bp synthetic polyA signal for mRNA termination.

Previously studies have validated cardiac expression using MHCK7 promoter (Salva et al. *Mol Ther* 15, 320-329 (2007) and AAVrh74 achieving skeletal, diaphragm, and cardiac muscle expression (Sondergaard et al. *Annals of clinical and Transl Neurology* 2, 256-270 (2015)), the sequence of construct of FIG. 1 was encapsidated into AAVrh.74 virions. The molecular clone of the AAVrh.74 serotype was cloned from a rhesus macaque lymph node and is described in in Rodino-Klapac et al. *Journal of Translational medicine* 5, 45 (2007).

Example 2

Intramuscular Expression Studies Using rAAV.MHCK7.Micro-Dystrophin

Figure 2:
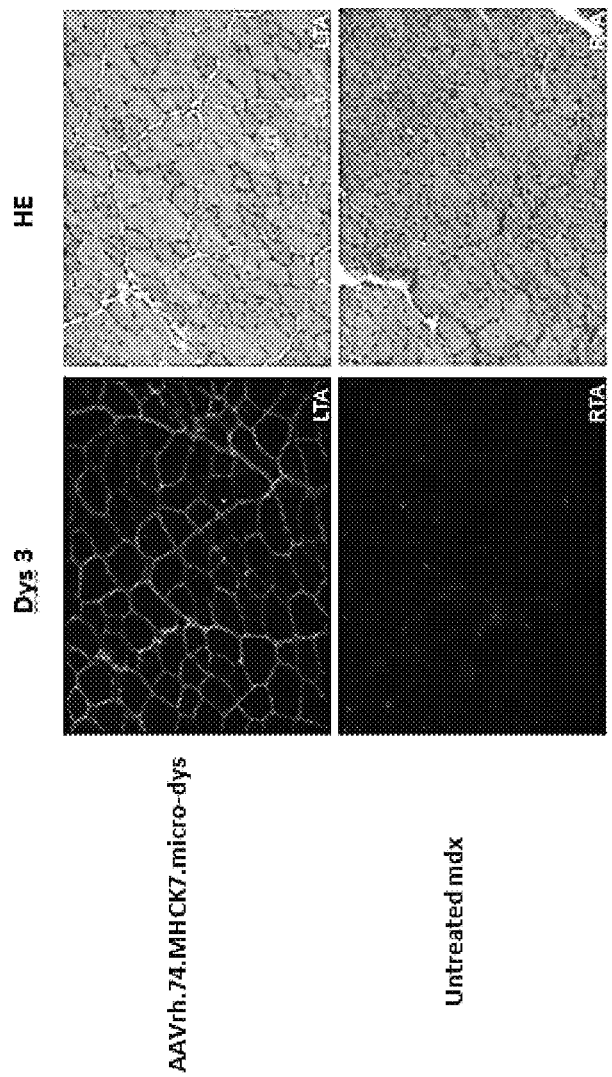
FIG. 2 demonstrates dystrophin protein expression following intramuscular delivery of AAVrh.74.MHCK7 construct. The tibialis anterior muscle of mdx mice was injected with $1\times10^{11}$ vg (n=5 per group). Six weeks later the muscles were harvested and stained for dystrophin expression with an N-terminal antibody for dystrophin and hematoxylin and eosin staining.

Expression studies were conducted with the human micro-dystrophin construct (rAAVrh74.MHCK7. micro-dystrophin; described in Example 1) by intramuscular injection. The tibialis anterior muscle of mdx mice (spontaneous $Dmd^{mdx}$ mutant mice that do not express dystrophin) were injected with $1\times10^{11}$ vg of the cassette (n=5 per group). Six weeks later the muscles were harvested and stained for dystrophin (Dys3) expression with an N-terminal antibody for dystrophin and hematoxylin and eosin (HE) staining. FIG. 2 shows diffuse gene expression and reduction in centrally located nuclei with $1\times10^{11}$ vg dose compared to the untreated muscle. Furthermore, a decrease in central nucleation with an increase in average fibers/frame was observed following treatment with micro-dystrophin construct. Expression levels of the rAAVrh74.MHCK7. micro-dystrophin construct were quantified at about 73%.

In addition to measuring micro-dystrophin localization and expression levels, skeletal muscle force was measured measurements and quantification of n following intramuscular injection of the cassette. Intramuscular expression of pAAV.MHCK7.micro-dystrophin construct resulted in significantly greater absolute and specific force production compared with untreated controls (FIGS. 3A and 3B, respectfully).

Example 3

Systemic Delivery of rAAVrh.74.MHCK7.Micro-Dys to Mdx Mice

Figure 4A:
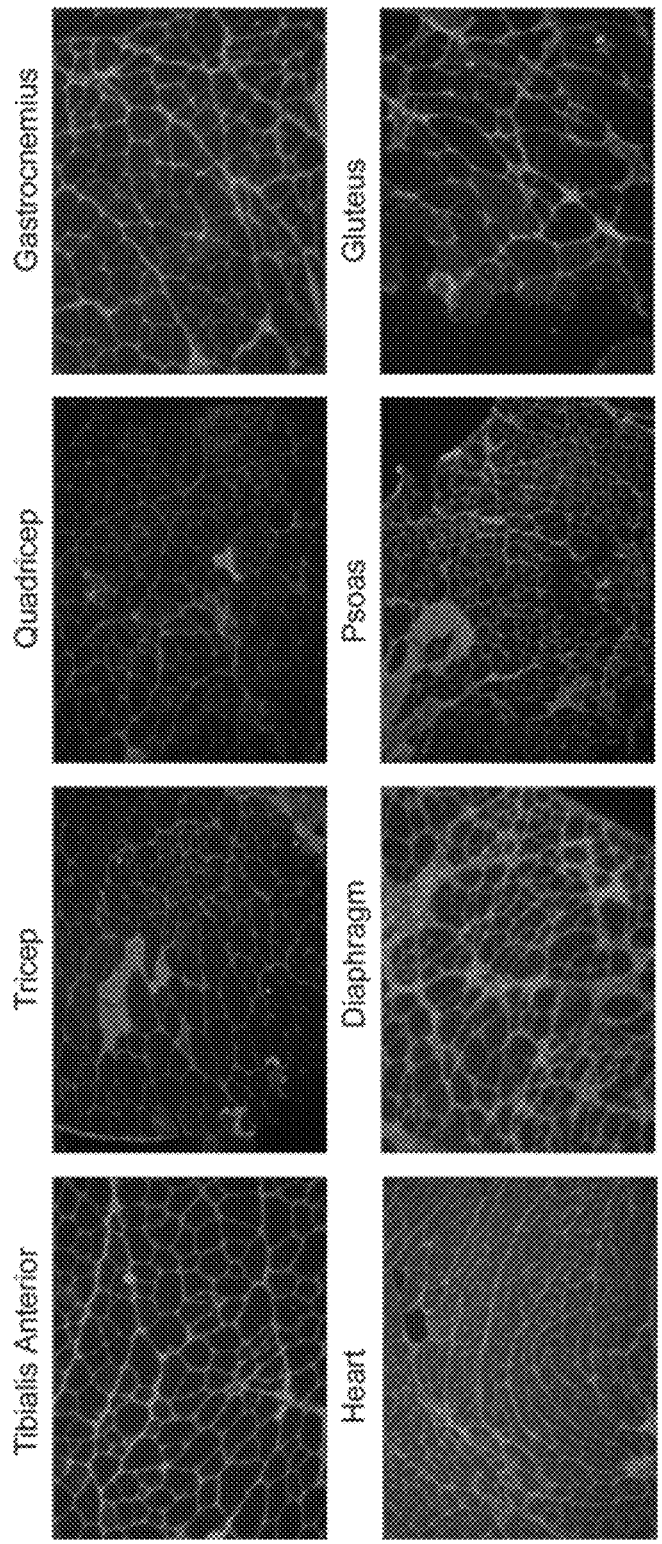
FIGS. 4A-4C demonstrates widespread transduction of skeletal diaphragm and cardiac muscle fibers after systemic administration. (A) Mdx mice were treated systemically at 6 weeks of age via the tail vein with $6\times10^{12}$ vg ($2\times10^{14}$ vg/kg) of AAVrh.74.MHCK7.micro-dys following 12 weeks of treatment. (B) Staining for micro-dystrophin demonstrates the shows quantification of the percentage of muscle fibers expressing micro-dystrophin in each tissue. (C) shows the specific force measured in the diaphragm at the low and high (planned clinical) dose. No significant difference was seen at low dose; however there was significant improvement at the high dose.
Figure 4C:
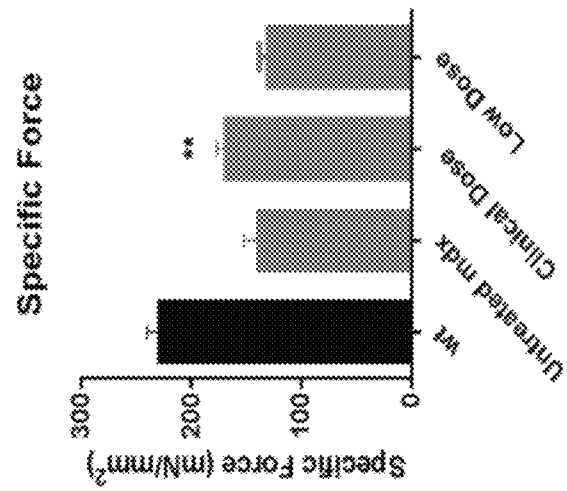
Figure 4B:
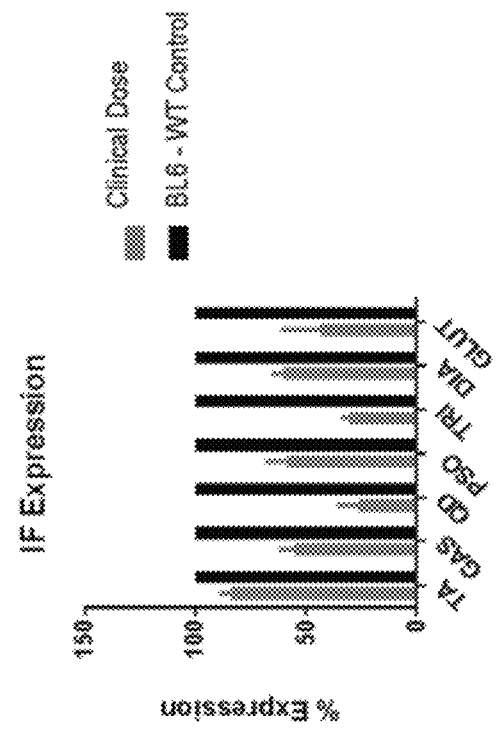
Figure 5:
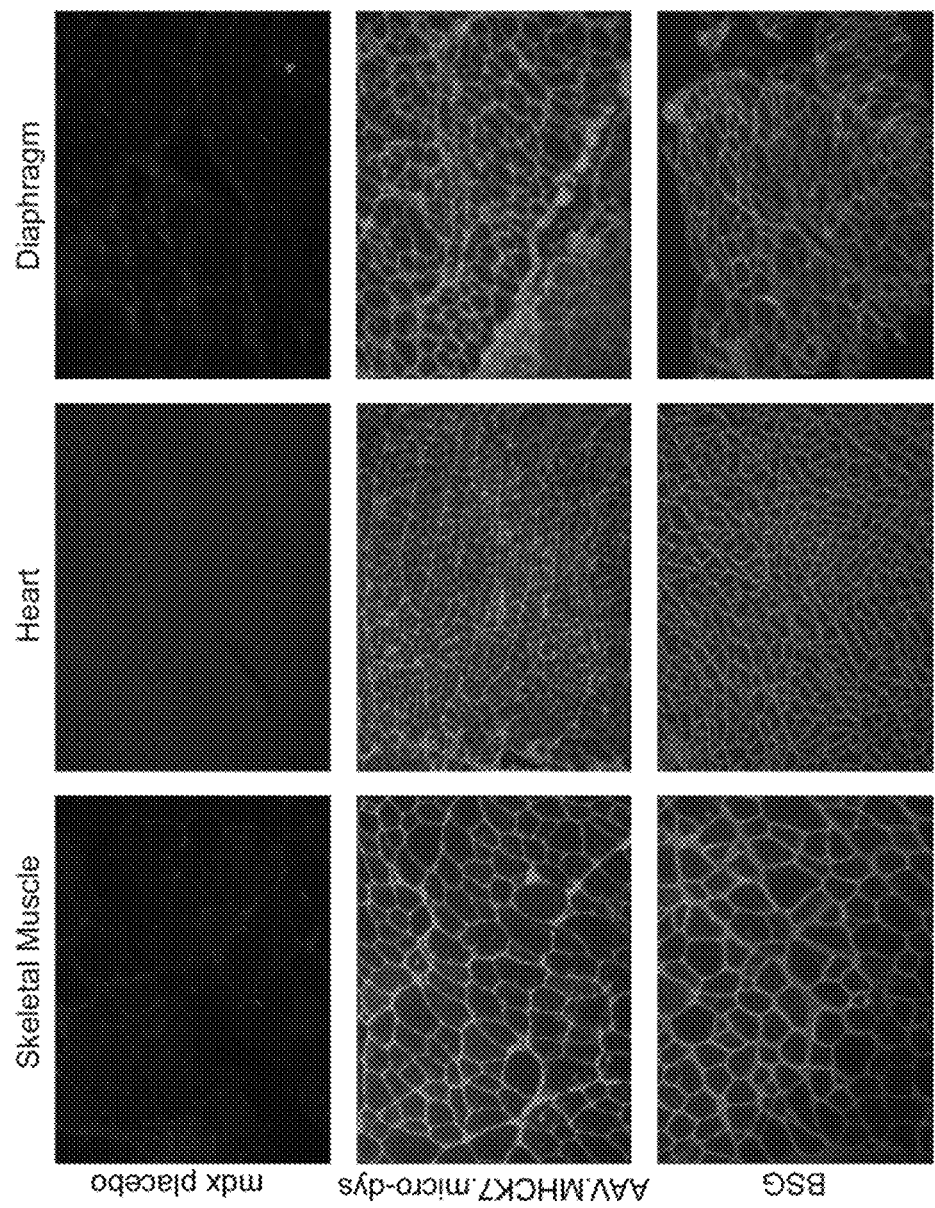
FIG. 5 demonstrates dystrophin protein expression following systemic delivery of AAVrh.74.MHCK7.micro-dys construct. Mdx mice (n=5) were treated systemically at 6 weeks of age via the tail vein with $6\times10^{12}$ vg of AAVrh.74.MHCK7.micro-dys following 12 weeks of treatment, all muscles were harvested and stained for dystrophin and restoration of DAPC components (beta-sarcoglycan shown).

Cohorts of mdx mice were injected via tail vein with either $2\times10^{12}$ vg ($8\times10^{13}$ vg/kg) or high dose (planned clinical dose) $6\times10^{12}$ vg ($2\times10^{14}$ vg/kg) of rAAVrh.74.MHCK7.micro-dys at 6 weeks of age. Following 12 weeks of treatment, all muscles were harvested and stained for dystrophin and restoration of DAPC components. Systemically injected (tail vein) mice showed high levels of staining of dystrophin throughout all muscles. FIG. 4A represents the widespread transduction of skeletal, diaphragm and cardiac muscle fibers after a $6\times10^{12}$ vg ($2\times10^{14}$ vg/kg) systemic dose. FIG. 4B shows quantification of the percentage of muscle fibers expressing micro-dystrophin in each tissue. Finally the diaphragm was tested for functional improvement (FIG. 4C). No significant difference was seen at low dose; however there was significant improvement at the high dose. Importantly, FIG. 5 demonstrates other components of the DAPC were completely restored following micro-dystrophin delivery. Shown is Beta-sarcoglycan (B-SG).

Figure 6:
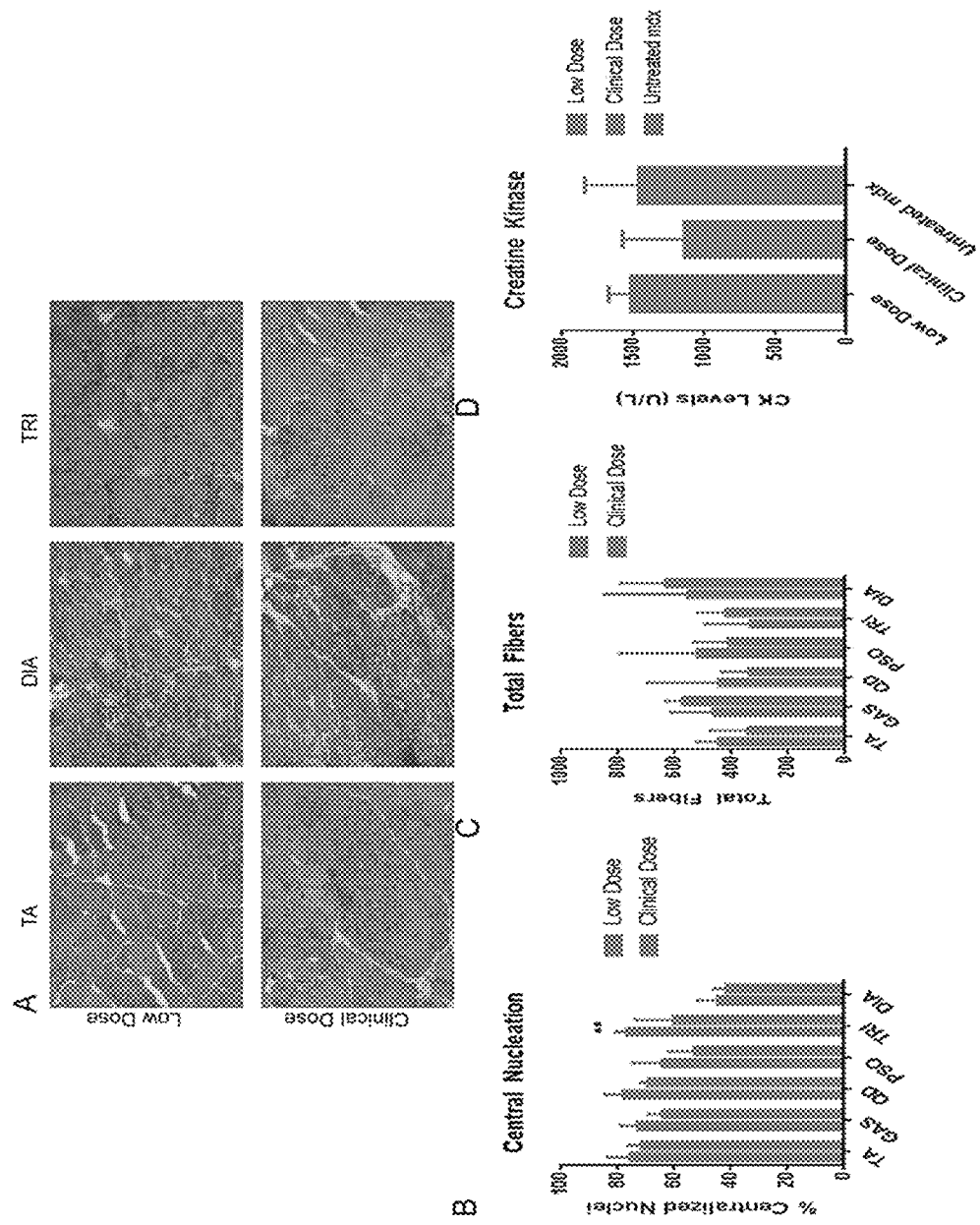
FIG. 6A-6D demonstrates the toxicology/safety of AAVrh.74.MHCK7. Hematoxylin and eosin (H&E) staining was performed on the following muscle tissues to analyze toxicity: Tibialis anterior (TA), Gastrocnemius (GAS), Quadriceps (QD), Psoas (PSO), Triceps (TRI), and Diaphragm (DIA) (FIG. 6A). No toxicity was noted. As an indicator of efficacy, the number of muscle fibers with centrally placed nuclei (CN) was quantified (FIG. 6B). CN are indicative of cycles of muscle degeneration and regeneration and thus reduction in CN demonstrates treatment effect.

The toxicology/safety of AAVrh.74.MHCK7.Micro-dys are evaluating by administering the vector via intravenous (i.v.) injection to the tail vein of mdx mice per Table 1. There was no evidence of toxicity in any of the muscle tissues analyzed including: Tibialis anterior (TA), Gastrocnemius (GAS), Quadriceps (QD), Psoas (PSO), Triceps (TRI), and Diaphragm (DIA) (FIGS. 6A and, B). The number of centrally placed nuclei was decreased with the high dose $6\times10^{12}$ vg ($2\times10^{14}$ vg/kg). Historically, central nucleation of skeletal muscles in untreated age matched mdx mice are on average ~80%. Finally, the preliminary data from a small sample size (n=3) demonstrates a decrease level of CK release (U/L) in serum of high dose treated mice (D). Independent t-tests were used to locate differences (p<0.05); Data are reported as means±SEM.

TABLE 1

| Outline of toxicology/safety study of rAAVrh.74.MHCK7.Micro-dys in mice. | | | | | | |
|---|---|---|---|---|---|---|
| Cohort Number | Study Agent | Dose (vg/kg) | Treatment Day 0 | Follow-up Day 1 | Sacrificial End-Point Week 6 | Extra |
| (1) Low Dose | AAVrh.74.MHCK7.Micro-dys | $8.0\times10^{13}$ | Single i.v. injection to the tail vein of mdx mice | 24 h Weight, Clinical Observations | 5 M | +2 |
| (2) High Dose | AAVrh.74.MHCK7.Micro-dys | $2.0\times10^{14}$ | | | 5 M | +2 |
| (3) Control | Vehicle (LRS) | 0 | | | 5 M | +2 |
| TOTAL MICE | | | | | N = 21 | |

Example 4

Generation of the pAAV.MCK.Micro-Dystrophin Construct

The pAAV.MCK.micro-dystrophin plasmid was constructed by inserting the MCK expression cassette driving a codon optimized human micro-dystrophin cDNA sequence into the AAV cloning vector psub201 (Samulski et al., *J. Virol.* 61(10):3096-3101). A muscle-specific regulatory element was included in the construct to drive muscle-specific gene expression. This regulatory element comprised the mouse MCK core enhancer (206 bp) fused to the 351 bp MCK core promoter (proximal). After the core promoter, the construct comprises the 53 bp endogenous mouse MCK Exon1 (untranslated) for efficient transcription initiation, followed by the SV40 late 16S/19S splice signals (97 bp) and a small 5'UTR (61 bp). The intron and 5' UTR was derived from plasmid pCMVβ (Clontech). The micro-dystrophin cassette has a consensus Kozak immediately in front of the ATG start and a small 53 bp synthetic polyA signal for mRNA termination. The human micro-dystrophin cassette contains the (R4-R23/Δ71-78) domains as previously described by Harper et al. *Nat. Med.* 8(3):253-61, 2002

Figure 7:
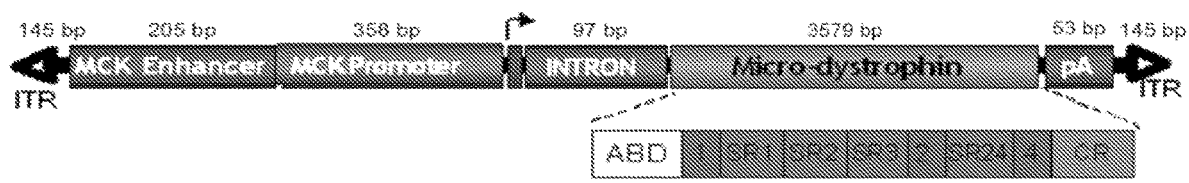
FIG. 7 illustrates the pAAV.MCK.micro-dystrophin plasmid construct.

The pAAV.MCK.micro-dystrophin plasmid contained the human micro-dystrophin cDNA expression cassette flanked by AAV2 inverted terminal repeat sequences (ITR) (see FIG. 7). This sequence was encapsidated into AAVrh.74 virions. The molecular clone of the AAVrh.74 serotype was cloned from a rhesus macaque lymph node and is described in Rodino-Klapac et al. *Journal of Tran. Med.* 45 (2007).

Example 5

Potency and Dose Analysis Using rAAV.MCK.Micro-Dystrophin

Figure 8:
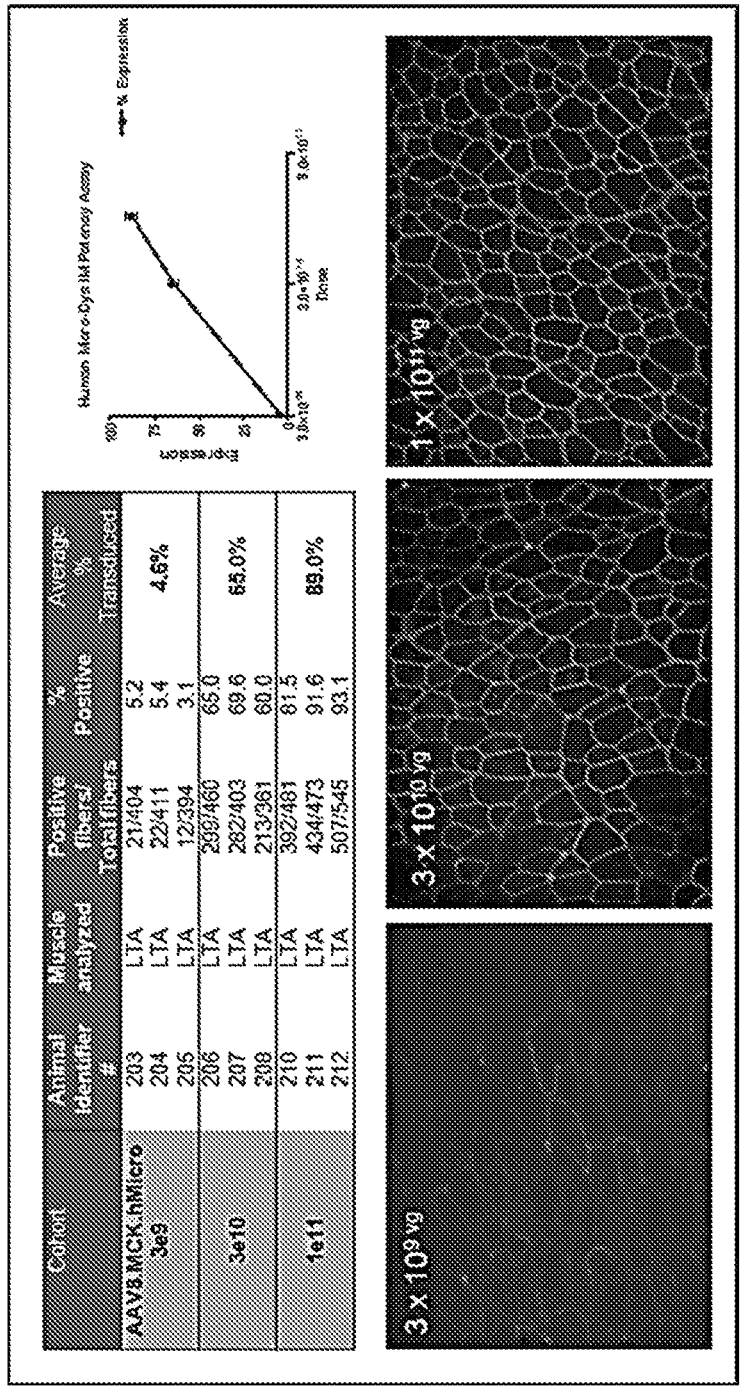
FIG. 8 provides the results of a rAAVrh74.MCK. micro-dystrophin (human) potency assay. The tibialis anterior muscle of mdx mice was injected with $3\times10^9$, $3\times10^{10}$, or $1\times10^{11}$ vg (n=3 per group). Four weeks later the muscles were harvested and stained for dystrophin expression with the N-terminal Dys3 antibody. There was a linear correlation between expression and dose where very little expression (no effect level) at $3\times10^9$ vg and 89% expression at $1\times10^{11}$ vg.

Expression studies were conducted with the human micro-dystrophin construct (rAAV.MCK.micro-dystrophin; described in Example 1) by intramuscular injection. The tibialis anterior (TA) muscle of mdx mice (spontaneous $Dmd^{mdx}$ mutant mice that do not express dystrophin) were injected with $3\times10^9$, $3\times10^{10}$, or $1\times10^{11}$ vg (n=3 per group). Four weeks later the muscles were harvested and stained for dystrophin expression using an antibody specific for the N-terminal Dys3 and hematoxylin and eosin (HE) staining. FIG. 8 show a linear correlation between expression and dose where very little expression (no effect level) at $3\times10^9$ vg and 89% expression at $1\times10^{11}$ vg.

Example 6

Vascular Delivery of rAAV.MCK.Micro-Dystrophin to Mdx Mice

Using a model of isolated limb perfusion model (Rodino-Klapac et al., *J. Trans. Med.* 5(45): 1-11, 2007), mdx mice (n=10) were injected with $1\times10^{11}$ vg of rAAVrh.74.MCK.micro-dystrophin via the femoral artery and performed outcomes analysis was carried out. Three months post gene transfer, lower limb muscles were harvested and efficacy studies demonstrated significant improvement in both force and resistance to eccentric contraction induced injury (FIG. 9).

Figure 9A:
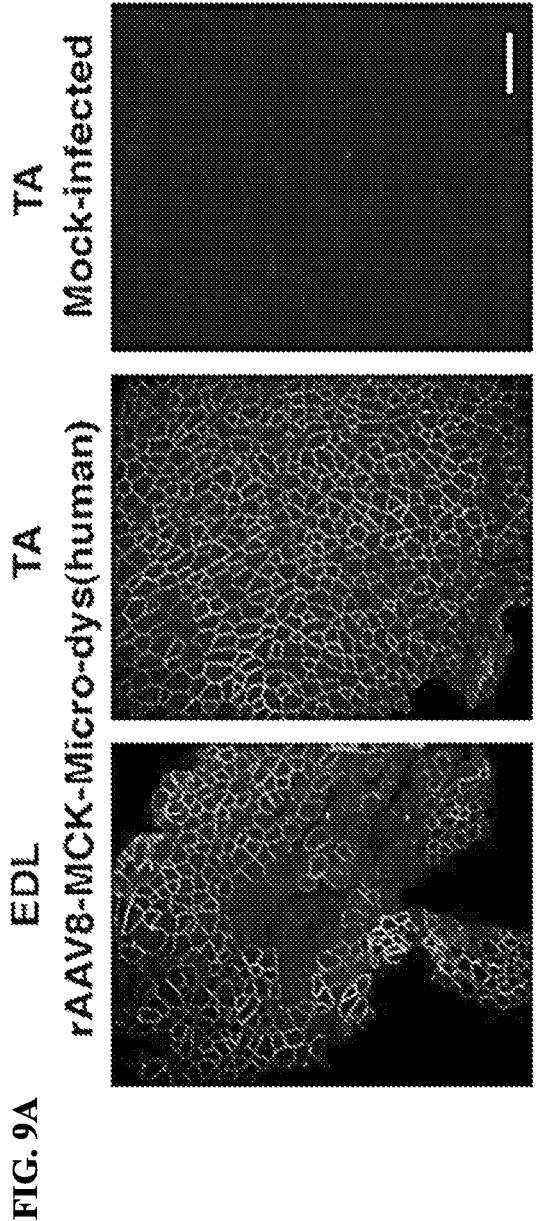
FIGS. 9A-9C demonstrate that Human micro-dystrophin improves force generation and protection from eccentric contraction induced injury. (A) Dystrophin protein immunostaining in the extensor digitorum longus (EDL) and TA shows expression in mdx myofibers following rAAVrh.74-MCK-Micro-dys (human) injection via the femoral artery. Mock-infected muscle was stained in an identical manner and exposures are time matched. (B) rAAVrh.74-MCK-Micro-dys significantly increased normalized specific force relative to mock-treated mdx muscles (P<0.05 vs. mdx). (C) mdx muscles infected with rAAVrh.74-MCK-Micro-dys(human) were compared with mock-infected contralateral mdx EDL muscles and WT (WT C57Bl/10) EDL muscles for force drop during repetitive eccentric contractions at 12 wks post gene transfer. rAAVrh.74-MCK-micro-dystrophin (Micro-dys) treatment significantly protected against loss of force compared with mock-treated mdx muscles (P<0.001 vs. mdx). Errors are SEMs.
Figure 9C:
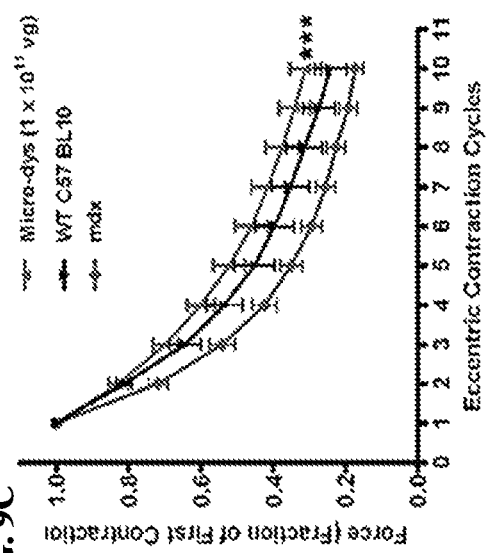
Figure 9B:
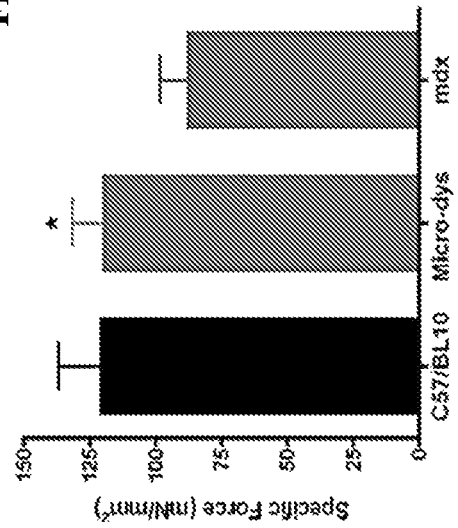

Dystrophin protein immunostaining in the extensor digitorum longus (EDL) muscle and TA muscle shows expression in a mdx myofibers following rAAVrh.74-MCK-Micro-dys treatment (FIG. 9A). Mock-infected muscle was stained in an identical manner and exposures are time matched. FIG. 9B demonstrates that rAAVrh.74-MCK-Micro-dys significantly increased normalized specific force relative to mock-treated mdx muscles (P<0.05 vs. mdx). In addition, the mdx muscles infected with rAAVrh.74-MCK-Micro-dys(human) were compared with mock-infected contralateral mdx EDL muscles (blue) and Wild Type (WT C57B1/10) EDL muscles for force drop during repetitive eccentric contractions at 12 weeks post gene transfer (FIG. 9C). rAAVrh.74-MCK-micro-dystrophin (Micro-dys) treatment significantly protected against loss of force compared with mock-treated mdx muscles (P<0.001 vs. mdx).

Example 7

Co-Delivery AAVrh74.MHCK7.Micro-Dystrophin+ AAVrh74.CMV.miR29C

To determine whether miR-29c/micro-dystrophin combined gene therapy approach would be more beneficial at reducing fibrosis, 4-week-old mdx/utrn$^{+/-}$ mice received an intramuscular injection of AAVrh74.MHCK7.micro-dystrophin and rAAVrh74.CMV.miR-29c at $5\times10^{11}$ vgs each to the left gastrocnemius muscle. rAAVrh.74. MHCK7.micro-dystrophin, and rAAVrh.74. MHCK7.micro-dystrophin alone. The mice were analyzed at 12 weeks post injection which is considered early therapy.

The pAAVrh74.MHCK7.micro-dystrophin plasmid contains the human micro-dystrophin cDNA expression cassette flanked by AAV2 inverted terminal repeat sequences (ITR) as shown in FIG. 10 and is described in detail in Example 1. It is this sequence that was encapsidated into AAV rh.74 virions.

The pAAV.CMV.miR29C plasmid contains the mir29c cDNA in a miR-30 stem loop backbone flanked by AAV2 inverted terminal repeat sequences (ITR). It is this sequence that was encapsidated into AAVrh.74 virions. In addition, a few nucleotides with in the miR-29c target sequence were changed to mimic Watson-crick pairing at this site as in shRNA-miR(luc). According to ShRNA-luc design, the hairpin should be perfectly complementary throughout its length. Plus, the more changes to the passenger strand, the more likely the elimination of any endogenous mechanism that regulates miR-29 processing that could recognize the miRNA via the stem. The 19$^{th}$ base of the guide strand was modified to a cytosine to mimic the nucleotide that precedes the cleavage site in natural mi-29c sequence and the corresponding base on the other strand was changed to preserve pairing. as shown in FIG. 12.

Measurement of absolute (FIG. 13A) and normalized specific (FIG. 13B) following tetanic contraction demonstrated increased force with combination therapy compared to untreated mdx/utrn$^{+/-}$ muscle and micro-dystrophin therapy alone (*p<0.05). Muscles were then assessed for loss of force following repetitive eccentric contractions. Mice co-treated with miR-29c/micro-dystrophin and micro-dystrophin alone showed a protection from loss of force compared with untreated mdx/utrn$^{+/-}$ muscles (FIG. 13C). Sirius Red stain representative images demonstrating muscle fibers (green) and collagen content (red) are shown in FIG. 13D.

Figure 14A:
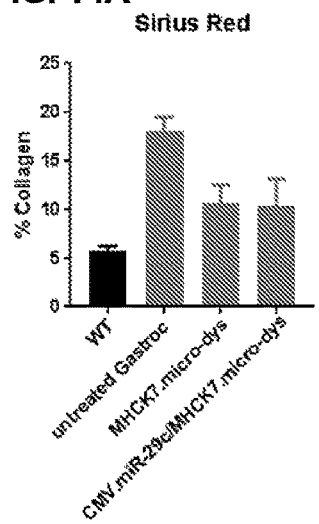
FIGS. 14A-14F demonstrate that treatment of AAV.CMV.miR-29c/MHCK7.micro-dystrophin combination therapy is effective at reducing fibrosis and ECM expression. (A) Sirius Red staining shows a reduction in collagen staining in both treated cohorts. (B) qRT-PCR confirms an increase in miR-29c transcript levels in the treated cohorts (n=2-3 for all groups) One-way ANOVA. Semi-quantitative qRT-PCR shows a reduction in Col1A1 and Col3A1 (C, D), Fbn (E) and Tgfβ1 (F) levels in the AAV.CMV.miR-29c/AAV.MHCK7.micro-dystrophin treated muscle compared to the contralateral limb and the single therapy of MHCK7.micro-dystrophin, with Col1A1 and Col3A1 being significant. C-F (n=2-3 per group) One-way ANOVA. All data represent mean±SEM. (*p<0.05, p<0.01, *p<0.001).
Figure 14B:
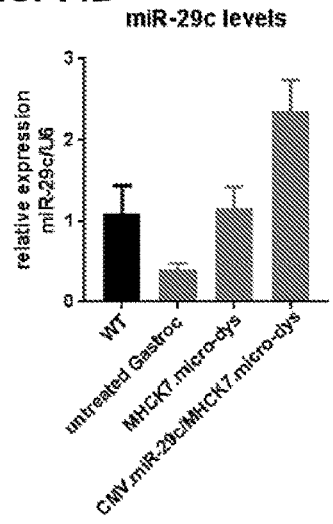

GAS muscle was analyzed 12 months post-injection to assess collagen accumulation by Sirius Red staining and subsequent quantification with ImageJ. Sirius Red staining shows a reduction in collagen staining in both treated cohorts. (FIG. 14A). Additional outcomes included miR-29c and collagen transcript levels. qRT-PCR confirms an increase in miR-29c transcript levels in the treated cohorts (n=2-3 for all groups) One-way ANOVA (FIG. 14B).

Figure 14C:
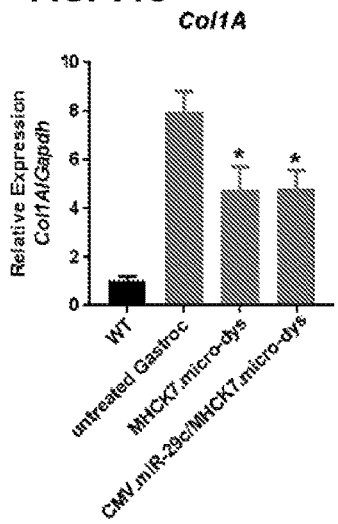
Figure 14D:
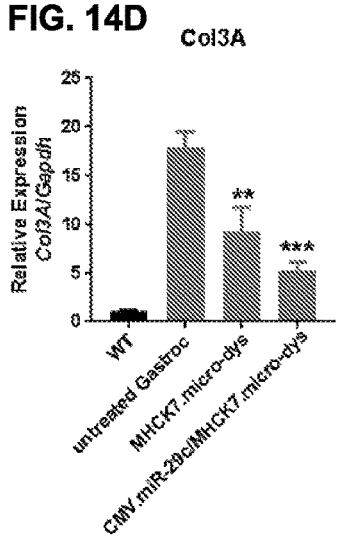
Figure 14E:
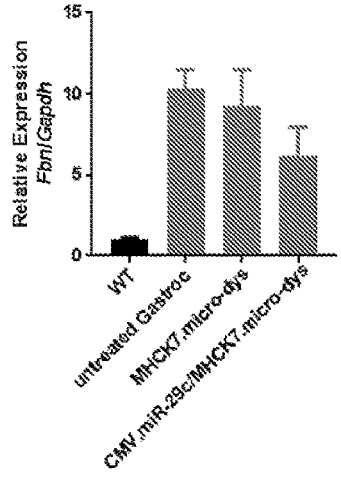

To further validate reduction of collagen observed by picrosirius red staining, semi-quantitative qRT-PCR was performed on the muscle to quantify transcript levels of Col1A, Col3A and also another ECM component, fibronectin (Fbn). qRT-PCR analysis detected a decrease in Col1A and Col3A following co-treatment (FIGS. 14C and 14D). The analysis revealed that Fbn was significantly reduced only in the co-treated cohort (FIG. 14E).

Figure 14F:
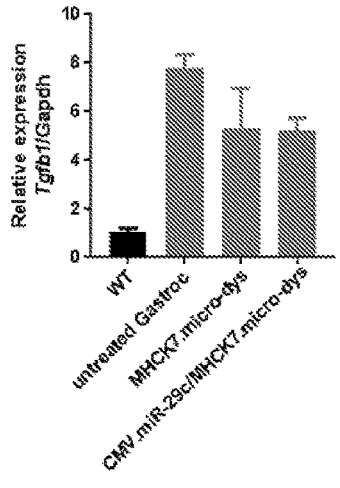

TGF-β1 has been previously shown to be up regulated in dystrophic muscle, likely playing a role in the initiation of the fibrotic cascade. TGF-β1 is a known pro-fibrotic cytokine that down regulates miR-29c and is responsible for conversion of myoblasts to myofibroblasts with an increase in collagen and muscle fibrogenesis. qRT-PCR analysis shows that co-treated muscle had lower levels of TGF-β1 compared to uninjected muscle and either treatment alone (FIG. 14F).

Figure 15A:
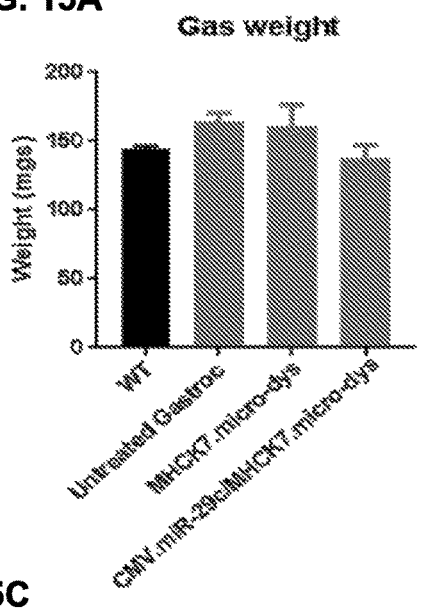
FIGS. 15A-15D demonstrate that treatment of AAV.CMV.miR-29c/MHCK7.micro-dystrophin combination therapy increased fiber diameter. (A) Treated gas weights showed no significant difference compared WT or untreated muscle. (B) miR-29c/micro-dystrophin combination treatment demonstrated an increase in average fiber size. Comparing mdx/utrn$^{+/-}$ controls with miR-29c/micro-dystrophin treated mdx/utrn$^{+/-}$, the average diameter increased from 29.02 to 33.61 μm (n=5-6 per group), One-way ANOVA. (C) The co-delivery produced a shift towards wild-type fiber size distribution. (D) The number of muscle fibers per mm$^2$ in the miR-29c/micro-dystrophin combination treatment was no different from untreated mice or WT mice. C-F (n=5-5 per group), One-way ANOVA. All data represent mean±SEM. (*p<0.001, **p<0.0001)
Figure 15B:
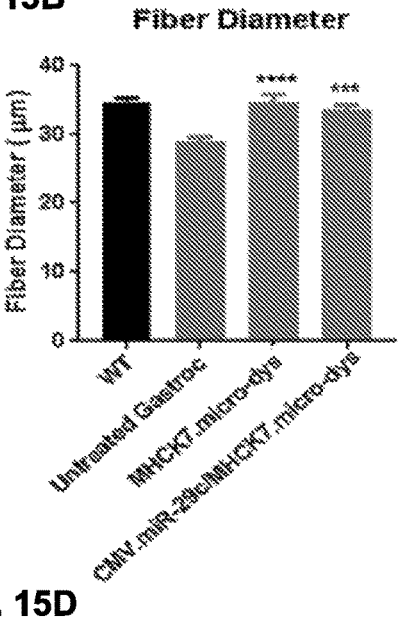
Figure 15C:
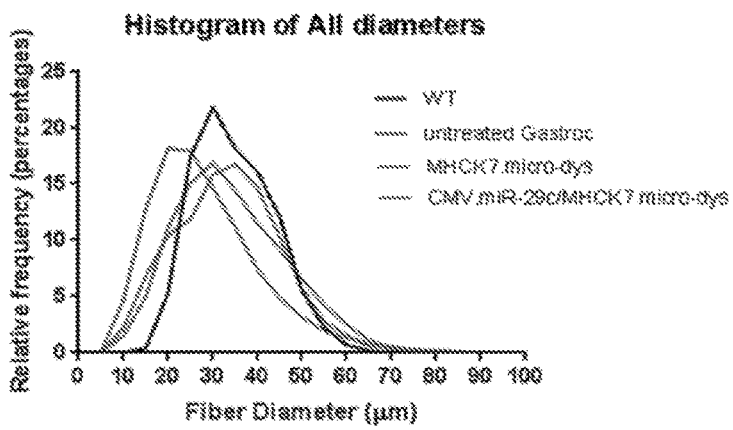
Figure 15D:
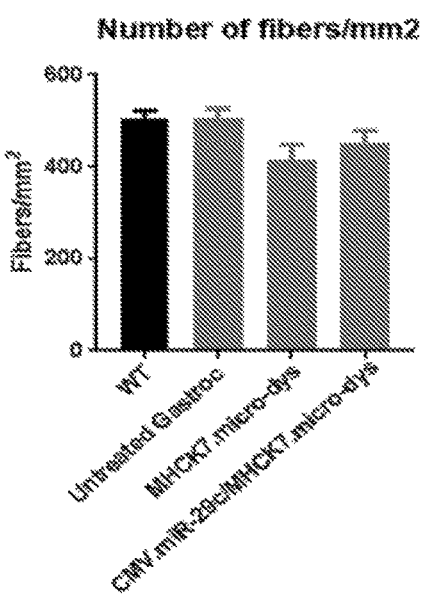

The effect of AAV.CMV.miR-29c/MHCK7.micro-dystrophin combination therapy on muscle fiber diameter was also investigated. As shown in FIG. 15, the combination therapy increased fiber diameter. FIGS. 15A and 15B demonstrate that MHCK7.micro-dystrophin treated muscle gas weights show no significant difference compared WT or untreated muscle, while miR-29c/micro-dystrophin combination treatment demonstrated an increase in average fiber size. Comparing mdx/utrn$^{+/-}$ controls with miR-29c/micro-dystrophin treated mdx/utrn$^{+/-}$, the average diameter increased from 29.02 to 33.6 µm (n=5-6 per group). FIG. 15C demonstrates that the combination therapy produced a shift towards wild-type fiber size distribution in the mdx/utrn$^{+/-}$ mice. FIG. 15D indicates that the number of muscle fibers per mm$^2$ in the miR-29c/micro-dystrophin combination treatment was no different from untreated mice or WT mice.

Initial results using rAAV.miR-29c as an anti-fibrotic therapy suggest that there is beneficial effect with reduction in collagen levels, a key contributor in fibrosis. Moreover, when combined with micro-dystrophin to improve membrane stability, miR29 up regulation normalized muscle force.

REFERENCES

1. Hoffman, E. P., Brown, R. H., Jr. & Kunkel, L. M. Dystrophin: the protein product of the Duchenne muscular dystrophy locus. *Cell* 51, 919-928 (1987).
2. Straub, V. & Campbell, K. P. Muscular dystrophies and the dystrophin-glycoprotein complex. *Curr Opin Neurol* 10, 168-175 (1997).
3. Sacco, A., et al. Short telomeres and stem cell exhaustion model Duchenne muscular dystrophy in mdx/mTR mice. *Cell* 143, 1059-1071 (2010).
4. Wallace, G. Q. & McNally, E. M. Mechanisms of muscle degeneration, regeneration, and repair in the muscular dystrophies. *Annu Rev Physiol* 71, 37-57 (2009).
5. Zhou, L. & Lu, H. Targeting fibrosis in Duchenne muscular dystrophy. *J Neuropathol Exp Neurol* 69, 771-776 (2010).
6. Desguerre, I., et al. Endomysial fibrosis in Duchenne muscular dystrophy: a marker of poor outcome associated with macrophage alternative activation. *J Neuropathol Exp Neurol* 68, 762-773 (2009).
7. DiPrimio, N., McPhee, S. W. & Samulski, R. J. Adeno-associated virus for the treatment of muscle diseases: toward clinical trials. *Curr Opin Mol Ther* 12, 553-560 (2010).
8. Mendell, J. R., et al. Sustained alpha-sarcoglycan gene expression after gene transfer in limb-girdle muscular dystrophy, type 2D. *Ann Neurol* 68, 629-638 (2010).
9. Mendell, J. R., et al. Limb-girdle muscular dystrophy type 2D gene therapy restores alpha-sarcoglycan and associated proteins. *Ann Neurol* 66, 290-297 (2009).
10. Mendell, J. R., et al. A phase 1/2a follistatin gene therapy trial for becker muscular dystrophy. *Molecular therapy: the journal of the American Society of Gene Therapy* 23, 192-201 (2015).
11. Carnwath, J. W. & Shotton, D. M. Muscular dystrophy in the mdx mouse: histopathology of the soleus and extensor digitorum longus muscles. *J Neurol Sci* 80, 39-54 (1987).
12. Coulton, G. R., Morgan, J. E., Partridge, T. A. & Sloper, J. C. The mdx mouse skeletal muscle myopathy: I. A histological, morphometric and biochemical investigation. *Neuropathol Appl Neurobiol* 14, 53-70 (1988).
13. Cullen, M. J. & Jaros, E. Ultrastructure of the skeletal muscle in the X chromosome-linked dystrophic (mdx) mouse. Comparison with Duchenne muscular dystrophy. *Acta Neuropathol* 77, 69-81 (1988).
14. Dupont-Versteegden, E. E. & McCarter, R. J. Differential expression of muscular dystrophy in diaphragm versus hindlimb muscles of mdx mice. *Muscle Nerve* 15, 1105-1110 (1992).
15. Stedman, H. H., et al. The mdx mouse diaphragm reproduces the degenerative changes of Duchenne muscular dystrophy. *Nature* 352, 536-539 (1991).
16. Deconinck, A. E., et al. Utrophin-dystrophin-deficient mice as a model for Duchenne muscular dystrophy. *Cell* 90, 717-727 (1997).
17. Grady, R. M., et al. Skeletal and cardiac myopathies in mice lacking utrophin and dystrophin: a model for Duchenne muscular dystrophy. *Cell* 90, 729-738 (1997).
18. Love, D. R., et al. An autosomal transcript in skeletal muscle with homology to dystrophin. *Nature* 339, 55-58 (1989).
19. Tinsley, J. M., et al. Primary structure of dystrophin-related protein. *Nature* 360, 591-593 (1992).
20. Tinsley, J., et al. Expression of full-length utrophin prevents muscular dystrophy in mdx mice. *Nat Med* 4, 1441-1444 (1998).
21. Squire, S., et al. Prevention of pathology in mdx mice by expression of utrophin: analysis using an inducible transgenic expression system. *Hum Mol Genet* 11, 3333-3344 (2002).
22. Rafael, J. A., Tinsley, J. M., Potter, A. C., Deconinck, A. E. & Davies, K. E. Skeletal muscle-specific expression of a utrophin transgene rescues utrophin-dystrophin deficient mice. *Nat Genet* 19, 79-82 (1998).
23. Zhou, L., et al. Haploinsufficiency of utrophin gene worsens skeletal muscle inflammation and fibrosis in mdx mice. *J Neurol Sci* 264, 106-111 (2008).
24. Gutpell, K. M., Hrinivich, W. T. & Hoffman, L. M. Skeletal Muscle Fibrosis in the mdx/utrn+/− Mouse Validates Its Suitability as a Murine Model of Duchenne Muscular Dystrophy. *PloS one* 10, e0117306 (2015).
25. Rodino-Klapac, L. R., et al. Micro-dystrophin and follistatin co-delivery restores muscle function in aged DMD model. *Human molecular genetics* 22, 4929-4937 (2013).
26. Nevo, Y., et al. The Ras antagonist, farnesylthiosalicylic acid (FTS), decreases fibrosis and improves muscle strength in dy/dy mouse model of muscular dystrophy. *PloS one* 6, e18049 (2011).
27. Rodino-Klapac, L. R., et al. A translational approach for limb vascular delivery of the micro-dystrophin gene without high volume or high pressure for treatment of Duchenne muscular dystrophy. *J Transl Med* 5, 45 (2007).
28. Mulieri, L. A., Hasenfuss, G., Ittleman, F., Blanchard, E. M. & Alpert, N. R. Protection of human left ventricular myocardium from cutting injury with 2,3-butanedione monoxime. *Circ Res* 65, 1441-1449 (1989).
29. Rodino-Klapac, L. R., et al. Persistent expression of FLAG-tagged micro dystrophin in nonhuman primates following intramuscular and vascular delivery. *Molecular therapy: the journal of the American Society of Gene Therapy* 18, 109-117 (2010).
30. Grose, W. E., et al. Homologous recombination mediates functional recovery of dysferlin deficiency following AAV5 gene transfer. *PloS one* 7, e39233 (2012).
31. Liu, M., et al. Adeno-associated virus-mediated micro-dystrophin expression protects young mdx muscle from contraction-induced injury. *Mol Ther* 11, 245-256 (2005).
32. Harper, S. Q., et al. Modular flexibility of dystrophin: implications for gene therapy of Duchenne muscular dystrophy. *Nature medicine* 8, 253-261 (2002).
33. Rodino-Klapac, L. R., et al. Persistent expression of FLAG-tagged micro dystrophin in nonhuman primates following intramuscular and vascular delivery. *Mol Ther* 18, 109-117 (2010).
34. Salva, M. Z., et al. Design of tissue-specific regulatory cassettes for high-level rAAV-mediated expression in skeletal and cardiac muscle. *Mol Ther* 15, 320-329 (2007).

35. Sondergaard, P. C., et al. AAV.Dysferlin Overlap Vectors Restore Function in Dysferlinopathy Animal Models. *Annals of clinical and translational neurology* 2, 256-270 (2015).
36. De, B. P., et al. High levels of persistent expression of alpha1-antitrypsin mediated by the nonhuman primate serotype rh.10 adeno-associated virus despite preexisting immunity to common human adeno-associated viruses. *Mol Ther* 13, 67-76 (2006).
37. Rodino-Klapac, L. R., et al. A translational approach for limb vascular delivery of the micro-dystrophin gene without high volume or high pressure for treatment of Duchenne muscular dystrophy. *Journal of translational medicine* 5, 45 (2007).
38. Bulfield et al., X chromosome-linked muscular dystrophy (mdx) in the mouse. *Proc Natl Acad Sci USA*. 1984; 81(4): 1189-1192.
39. Sicinski et al., The molecular basis of muscular dystrophy in the mdx mouse: a point mutation. *Science*. 1989 30; 244(4912):1578-80

What is claimed:

1. A method of treating muscular dystrophy comprising administering i) a therapeutically effective amount of a recombinant AAV vector comprising nucleotide 236 to nucleotide 4842 of SEQ ID NO: 3 and ii) a therapeutically effective amount of a recombinant AAV vector comprising nucleotides 120 to 2091 of SEQ ID NO: 6.

2. A method of increasing muscular force or muscle mass in a subject suffering from muscular dystrophy comprising administering i) a therapeutically effective amount of a recombinant AAV comprising nucleotide 236 to nucleotide 4842 of SEQ ID NO: 3 and ii) a therapeutically effective amount of a recombinant AAV vector comprising nucleotides 120 to 2091 of SEQ ID NO: 6.

3. A method of reducing or preventing fibrosis in a subject suffering from muscular dystrophy comprising administering i) a therapeutically effective amount of i) a recombinant AAV vector expressing comprising nucleotide 236 to nucleotide 4842 of SEQ ID NO: 3 and ii) a therapeutically effective amount of a recombinant AAV vector comprising nucleotides 120 to 2091 of SEQ ID NO: 6.

4. The method of claim 1 wherein the muscular dystrophy is Duchenne muscular dystrophy.

5. The method of claim 1 wherein at least one of the recombinant AAV vectors is the serotype AAVrh.74, AAV1, AAV2, AAV4, AAV5, AAV6, AAV7, AAV8, AAV9, AAV10, AAV11, AAV12 or AAV13.

6. The method of claim 1 wherein at least one of the recombinant AAV vectors is administered by intramuscular injection or intravenous injection.

7. The method of claim 1 wherein at least one of the recombinant AAV vectors is administered systemically.

8. The method of claim 7, wherein at least one of the recombinant AAV vectors is parenterally administered by injection, infusion or implantation.

9. The method of claim 2 wherein at least one of the recombinant AAV vectors is the serotype AAVrh.74, AAV1, AAV2, AAV4, AAV5, AAV6, AAV7, AAV8, AAV9, AAV10, AAV11, AAV12 or AAV13.

10. The method of claim 2 wherein at least one of the recombinant AAV vectors is administered by intramuscular injection or intravenous injection.

11. The method of claim 2 wherein at least one of the recombinant AAV vectors is administered systemically.

12. The method of claim 11, wherein at least one of the recombinant AAV vectors is parenterally administered by injection, infusion or implantation.

13. The method of claim 3 wherein at least one of the recombinant AAV vectors is the serotype AAVrh.74, AAV1, AAV2, AAV4, AAV5, AAV6, AAV7, AAV8, AAV9, AAV10, AAV11, AAV12 or AAV13.

14. The method of claim 3 wherein at least one of the recombinant AAV vectors is administered by intramuscular injection or intravenous injection.

15. The method of claim 3 wherein at least one of the recombinant AAV vectors is administered systemically.

16. The method of claim 15, wherein at least one of the recombinant AAV vectors is parenterally administered by injection, infusion or implantation.

\* \* \* \* \*

SEQUENCE LISTING

```
<160> NUMBER OF SEQ ID NOS: 10

<210> SEQ ID NO 1
<211> LENGTH: 3579
<212> TYPE: DNA
<213> ORGANISM: Homo sapiens

<400> SEQUENCE: 1
atgctgtggt gggaggaggt ggaggattgt tatgaaaggg aggacgtgca gaagaagact      60
tttaccaagt gggtgaacgc tcagttcagc aaatttggga agcagcacat cgagaatctg     120
ttttccgacc tgcaggatgg gagacggctg ctggatctgc tggaaggact gactggccag     180
aagctgccca agagaaggg gagcactagg gtgcacgccc tgaacaacgt gaacaaagct      240
ctgagagtgc tgcagaacaa caacgtggat ctggtgaata ttggcagtac tgatatcgtg     300
gacgggaacc acaaactgac actgggcctg atctggaaca ttattctgca ctggcaggtg     360
aaaaatgtga tgaagaacat catggccggg ctgcagcaga ccaattccga gaagatcctg     420
ctgtcttggg tgcggcagag cacccgcaac tatccccagg tgaacgtgat taacttcact     480
acatcctgga gcgacgggct ggccctgaat gctctgattc acagccacag gcctgatctg     540
ttcgactgga atagcgtggt gtgccagcag tctgccacac agcgcctgga acatgccttc     600
aatatcgctc ggtaccagct ggggatcgaa aaactgctgg acccagagga tgtggacact     660
acatacccag ataaaaagtc tattctgatg tacattacta gcctgttcca ggtgctgcca     720
cagcaggtgt ctattgaagc cattcaggag gtggaaatgc tgccccgccc ccccaaagtg     780
actaaagagg agcattttca gctgcatcat cagatgcatt acagccagca gattaccgtg     840
agcctggctc agggatatga gcgcaccagt agtccaaaac cacggttcaa gtcctacgct     900
tatacccagg ctgcctacgt gacaactagc gaccctacta gatccccctt tccatcccag     960
cacctggagg ccccagagga caagagcttt gggtccagcc tgatggaaag cgaggtgaat    1020
ctggatcggt accagacagc cctggaggag gtgctgagct ggctgctgag tgctgaagac    1080
acactgcagg cccagggcga aatttccaat gacgtggaag tggtgaagga tcagttccac    1140
acacacgagg gctatatgat ggacctgaca gctcaccagg ggcgcgtggg caatatcctg    1200
cagctgggct ctaaactgat cggcaccggg aaactgagtg aggacgagga aacagaagtg    1260
caggagcaga tgaacctgct gaacagccgc tgggagtgtc tgagagtggc tagtatggag    1320
aagcagtcca acctgcaccg ggtgctgatg gacctgcaga accagaaact gaaagagctg    1380
aacgactggc tgacaaagac tgaggaacgc acaaggaaga tggaggagga gccactggga    1440
cccgacctgg aggatctgaa gagacaggtg cagcagcata aggtgctgca ggaggatctg    1500
gaacaggagc aggtgcgggt gaactccctg acacatatgg tggtggtggt ggacgaatct    1560
agtggagatc acgccaccgc cgcccggag gaacagctga aggtgctggg ggaccggtgg    1620
gccaacattt gccggtggac cgaggacagg tgggtgctgc tgcaggacat cctgctgaaa    1680
```

| | | | | |
|---|---|---|---|---|
| tggcagaggc | tgaccgagga | gcagtgtctg | tttagtgctt | ggctgagcga gaaagaggac | 1740 |
| gccgtgaaca | agatccacac | aaccggcttt | aaggatcaga | acgaaatgct gtctagcctg | 1800 |
| cagaaactgg | ctgtgctgaa | ggccgatctg | agaaaaaga | agcagagcat gggcaaactg | 1860 |
| tatagcctga | aacaggacct | gctgagcacc | ctgaagaaca | agagcgtgac ccagaagaca | 1920 |
| gaagcctggc | tggataactt | tgcccgctgc | tgggacaacc | tggtgcagaa actggagaaa | 1980 |
| agtacagctc | agatctctca | ggctgtgacc | acaacccagc | ctagcctgac ccagacaacc | 2040 |
| gtgatggaaa | ccgtgaccac | cgtgacaacc | cgcgaacaga | tcctggtgaa acatgcccag | 2100 |
| gaaagagctgc | cacctccacc | tccccagaag | aagagaaccc | tggagcggct gcaggagctg | 2160 |
| caggaagcca | ctgacgaact | ggacctgaag | ctgaggcagg | ccgaagtgat taagggtct | 2220 |
| tggcagcctg | tgggcgatct | gctgattgat | tccctgcagg | accacctgga aaaggtgaag | 2280 |
| gctctgagag | gcgaaattgc | tccactgaag | gagaacgtga | gtcatgtgaa cgatctggct | 2340 |
| agacagctga | caaactggg | catccagctg | agcccataca | atctgagcac actggaggac | 2400 |
| ctgaatacca | ggtggaagct | gctgcaggtg | gctgtggaag | accgggtgcg gcagctgcat | 2460 |
| gaggcccatc | gcgacttcgg | accagccagc | cagcactttc | tgagcacatc cgtgcagggg | 2520 |
| ccctgggaga | gggccatttc | tcccaacaag | gtgccctact | atattaatca cgagacccag | 2580 |
| accacttgtt | gggaccatcc | caagatgaca | gaactgtacc | agtccctggc cgatctgaac | 2640 |
| aacgtgaggt | ttagcgctta | cagaaccgct | atgaagctga | acggctgca gaaggccctg | 2700 |
| tgcctggatc | tgctgtccct | gtccgccgcc | tgcgatgccc | tggatcagca taatctgaag | 2760 |
| cagaacgatc | agccaatgga | tatcctgcag | atcatcaact | gcctgaccac tatctacgac | 2820 |
| aggctggagc | aggagcacaa | caacctggtg | aacgtgcctc | tgtgcgtgga tatgtgcctg | 2880 |
| aactggctgc | tgaacgtgta | tgacactggg | cgcaccggcc | ggatcagagt gctgagtttt | 2940 |
| aaaactggga | ttatctccct | gtgtaaggcc | cacctggagg | acaagtacag gtacctgttc | 3000 |
| aagcaggtgg | ctagtagcac | tggattttgt | gaccagcgcc | gctgggact gctgctgcat | 3060 |
| gatagtatcc | agattcctag | acagctggga | gaggtggcta | gtttcggagg atctaacatc | 3120 |
| gaacccagcg | tgcgcagctg | tttccagttt | gccaataaca | aacctgaaat cgaggctgct | 3180 |
| ctgttcctgg | attggatgcg | cctggaacca | cagagcatgg | tgtggctgcc tgtgctgcac | 3240 |
| agagtggctc | ccgccgaaac | tgccaagcac | caggctaaat | gcaacatctg caaggaatgt | 3300 |
| cccattatcg | gctttcgcta | caggagtctg | aaacatttta | actacgatat tgccagagc | 3360 |
| tgcttctttt | ccggaagagt | ggccaaagga | cacaagatgc | actaccctat ggtggaatat | 3420 |
| tgcacccaa | ctacatctgg | cgaagatgtg | cgcgattttg | ccaaggtgct gaagaataag | 3480 |
| tttcggacta | agaggtactt | cgccaagcac | ccccgcatgg | ggtatctgcc agtgcagaca | 3540 |
| gtgctggaag | gagacaatat | ggagaccgat | acaatgtga | | 3579 |

<210> SEQ ID NO 2
<211> LENGTH: 810
<212> TYPE: DNA
<213> ORGANISM: Adeno-associated virus

<400> SEQUENCE: 2

| | | | | |
|---|---|---|---|---|
| gtttaaacaa | gcttgcatgt | ctaagctaga | cccttcagat | taaaaataac tgaggtaagg | 60 |
| gcctgggtag | gggaggtggt | gtgagacgct | cctgtctctc | ctctatctgc ccatcggccc | 120 |
| tttggggagg | aggaatgtgc | ccaaggacta | aaaaaaggcc | atggagccag aggggcgagg | 180 |

| | |
|---|---|
| gcaacagacc tttcatgggc aaaccttggg gccctgctgt ctagcatgcc ccactacggg | 240 |
| tctaggctgc ccatgtaagg aggcaaggcc tggggacacc cgagatgcct ggttataatt | 300 |
| aacccagaca tgtggctgcc ccccccccc caacacctgc tgcctctaaa ataaccctg | 360 |
| tccctggtgg atcccctgca tgcgaagatc ttcgaacaag gctgtggggg actgagggca | 420 |
| ggctgtaaca ggcttggggg ccagggctta tacgtgcctg ggactcccaa agtattactg | 480 |
| ttccatgttc ccggcgaagg gccagctgtc ccccgccagc tagactcagc acttagttta | 540 |
| ggaaccagtg agcaagtcag cccttggggc agcccataca aggccatggg gctgggcaag | 600 |
| ctgcacgcct gggtccgggg tgggcacggt gcccgggcaa cgagctgaaa gctcatctgc | 660 |
| tctcaggggc ccctccctgg gacagcccc tcctggctag tcacaccctg taggctcctc | 720 |
| tatataaccc aggggcacag gggctgccct cattctacca ccacctccac agcacagaca | 780 |
| gacactcagg agccagccag cggcgcgccc | 810 |

<210> SEQ ID NO 3
<211> LENGTH: 8611
<212> TYPE: DNA
<213> ORGANISM: Adeno-associated virus

<400> SEQUENCE: 3

| | |
|---|---|
| gcccaatacg caaaccgcct ctccccgcgc gttggccgat tcattaatgc agctggcgcg | 60 |
| ctcgctcgct cactgaggcc gcccgggcaa agcccgggcg tcgggcgacc tttggtcgcc | 120 |
| cggcctcagt gagcgagcga gcgcgcagag agggagtggc caactccatc actaggggtt | 180 |
| ccttgtagtt aatgattaac cgccatgct aattatctac gtagccatgt ctagagttta | 240 |
| aacaagcttg catgtctaag ctagacccctt cagattaaaa ataactgagg taagggcctg | 300 |
| ggtaggggag gtggtgtgag acgctcctgt ctctcctcta tctgccatc ggcccttttgg | 360 |
| ggaggaggaa tgtgcccaag gactaaaaaa aggccatgga gccagagggg cgagggcaac | 420 |
| agaccttca tgggcaaacc ttggggcccct gctgtctagc atgccccact acgggtctag | 480 |
| gctgccatg taaggaggca aggcctgggg cacccgaga tgcctggtta taattaaccc | 540 |
| agacatgtgg ctgccccccc cccccaaca cctgctgcct ctaaaaataa ccctgtccct | 600 |
| ggtggatccc ctgcatgcga agatcttcga caaggctgt gggggactga gggcaggctg | 660 |
| taacaggctt gggggccagg gcttatacgt gcctgggact cccaaagtat tactgttcca | 720 |
| tgttcccggc gaagggccag ctgtcccccg ccagctagac tcagcactta gtttaggaac | 780 |
| cagtgagcaa gtcagccctt ggggcagccc atacaaggcc atggggctgg gcaagctgca | 840 |
| cgcctgggtc cggggtgggc acggtgcccg ggcaacgagc tgaaagctca tctgctctca | 900 |
| ggggcccctc cctggggaca gcccctcctg gctagtcaca ccctgtaggc tcctctatat | 960 |
| aacccagggg cacaggggct gccctcattc taccaccacc tccacagcac agacagacac | 1020 |
| tcaggagcca gccagcggcg cgcccaggta agtttagtct ttttgtcttt tatttcaggt | 1080 |
| cccggatccg gtggtggtgc aaatcaaaga actgctcctc agtggatgtt gcctttactt | 1140 |
| ctaggcctgt acggaagtgt tacttctgct ctaaaagctg cggaattgta cccgcggccg | 1200 |
| ccaccatgct gtggtgggag gaggtggagg attgttatga agggaggac gtgcagaaga | 1260 |
| agacttttac caagtgggtg aacgctcagt tcagcaaatt tgggaagcag cacatcgaga | 1320 |
| atctgttttc cgacctgcag gatgggagac ggctgctgga tctgctggaa ggactgactg | 1380 |
| gccagaagct gcccaaagag aagggagca ctagggtgca cgccctgaac aacgtgaaca | 1440 |
| aagctctgag agtgctgcag aacaacaacg tggatctggt gaatattggc agtactgata | 1500 |

-continued

| | |
|---|---|
| tcgtggacgg gaaccacaaa ctgacactgg gcctgatctg gaacattatt ctgcactggc | 1560 |
| aggtgaaaaa tgtgatgaag aacatcatgg ccgggctgca gcagaccaat ccgagaaga | 1620 |
| tcctgctgtc ttgggtgcgg cagagcaccc gcaactatcc ccaggtgaac gtgattaact | 1680 |
| tcactacatc ctggagcgac gggctggccc tgaatgctct gattcacagc cacaggcctg | 1740 |
| atctgttcga ctggaatagc gtggtgtgcc agcagtctgc cacacagcgc ctggaacatg | 1800 |
| ccttcaatat cgctcggtac cagctgggga tcgaaaaact gctggaccca gaggatgtgg | 1860 |
| acactacata cccagataaa aagtctattc tgatgtacat tactagcctg ttccaggtgc | 1920 |
| tgccacagca ggtgtctatt gaagccattc aggaggtgga aatgctgccc cgcccccca | 1980 |
| aagtgactaa agaggagcat tttcagctgc atcatcagat gcattacagc cagcagatta | 2040 |
| ccgtgagcct ggctcaggga tatgagcgca ccagtagtcc aaaaccacgg ttcaagtcct | 2100 |
| acgcttatac ccaggctgcc tacgtgacaa ctagcgaccc tactagatcc cccttttccat | 2160 |
| cccagcacct ggaggcccca gaggacaaga gctttgggtc cagcctgatg gaaagcgagg | 2220 |
| tgaatctgga tcggtaccag acagccctgg aggaggtgct gagctggctg ctgagtgctg | 2280 |
| aagacacact gcaggcccag ggcgaaattt ccaatgacgt ggaagtggtg aaggatcagt | 2340 |
| tccacacaca cgagggctat atgatggacc tgacagctca ccaggggcgc gtgggcaata | 2400 |
| tcctgcagct gggctctaaa ctgatcggca ccgggaaact gagtgaggac gaggaaacag | 2460 |
| aagtgcagga gcagatgaac ctgctgaaca gccgctggga gtgtctgaga gtggctagta | 2520 |
| tggagaagca gtccaacctg caccgggtgc tgatggacct gcagaaccag aaactgaaag | 2580 |
| agctgaacga ctggctgaca aagactgagg aacgcacaag gaagatggag gaggagccac | 2640 |
| tgggaccccga cctggaggat ctgaagagac aggtgcagca gcataaggtg ctgcaggagg | 2700 |
| atctggaaca ggagcaggtg cgggtgaact ccctgacaca tatggtggtg gtggtggacg | 2760 |
| aatctagtgg agatcacgcc accgccgccc tggaggaaca gctgaaggtg ctgggggacc | 2820 |
| ggtgggccaa catttgccgg tggaccgagg acaggtgggt gctgctgcag acatcctgc | 2880 |
| tgaaatggca gaggctgacc gaggagcagt gtctgtttag tgcttggctg agcgagaaag | 2940 |
| aggacgccgt gaacaagatc cacacaaccg gctttaagga tcagaacgaa atgctgtcta | 3000 |
| gcctgcagaa actggctgtg ctgaaggccg atctggagaa aaagaagcag agcatgggca | 3060 |
| aactgtatag cctgaaacag gacctgctga gcacccctgaa gaacaagagc gtgacccaga | 3120 |
| agacagaagc ctggctggat aactttgccc gctgctggga caacctggtg cagaaactgg | 3180 |
| agaaaagtac agctcagatc tctcaggctg tgaccacaac ccagcctagc ctgacccaga | 3240 |
| caaccgtgat ggaaaccgtg accaccgtga cacaaccgcga acagatcctg gtgaaacatg | 3300 |
| cccaggaaga gctgccacct ccacctcccc agaagaagag aaccctggag cggctgcagg | 3360 |
| agctgcagga agccactgac gaactggacc tgaagctgag gcaggccgaa gtgattaagg | 3420 |
| ggtcttggca gcctgtgggc gatctgctga ttgattccct gcaggaccac ctggaaaagg | 3480 |
| tgaaggctct gagaggcgaa attgctccac tgaaggagaa cgtgagtcat gtgaacgatc | 3540 |
| tggctagaca gctgacaaca ctgggcatcc agctgagccc atacaatctg agcacactgg | 3600 |
| aggacctgaa taccaggtgg aagctgctgc aggtggctgt ggaagaccgg gtgcggcagc | 3660 |
| tgcatgaggc ccatcgcgac ttcggaccag ccagccagca ctttctgagc acatccgtgc | 3720 |
| aggggccctg ggagagggcc atttctccca caaggtgcc ctactatatt aatcacgaga | 3780 |
| cccagaccac ttgttgggac catcccaaga tgacagaact gtaccagtcc ctggccgatc | 3840 |

-continued

```
tgaacaacgt gaggtttagc gcttacagaa ccgctatgaa gctgagacgg ctgcagaagg    3900
ccctgtgcct ggatctgctg tccctgtccg ccgcctgcga tgccctggat cagcataatc    3960
tgaagcagaa cgatcagcca atggatatcc tgcagatcat caactgcctg accactatct    4020
acgacaggct ggagcaggag cacaacaacc tggtgaacgt gcctctgtgc gtggatatgt    4080
gcctgaactg gctgctgaac gtgtatgaca ctgggcgcac cggccggatc agagtgctga    4140
gttttaaaac tgggattatc tccctgtgta aggcccacct ggaggacaag tacaggtacc    4200
tgttcaagca ggtggctagt agcactggat tttgtgacca gcgccgcctg ggactgctgc    4260
tgcatgatag tatccagatt cctagacagc tgggagaggg ggctagtttc ggaggatcta    4320
acatcgaacc cagcgtgcgc agctgtttcc agtttgccaa taacaaacct gaaatcgagg    4380
ctgctctgtt cctggattgg atgcgcctgg aaccacagag catggtgtgg ctgcctgtgc    4440
tgcacagagt ggctgccgcc gaaactgcca agcaccaggc taaatgcaac atctgcaagg    4500
aatgtcccat tatcggcttt cgctacagga gtctgaaaca ttttaactac gatatttgcc    4560
agagctgctt ctttccggaa gagtggcca aggacacaa gatgcactac cctatggtgg    4620
aatattgcac cccaactaca tctggcgaag atgtgcgcga ttttgccaag gtgctgaaga    4680
ataagtttcg gactaagagg tacttcgcca agcacccccg catggggtat ctgccagtgc    4740
agacagtgct ggaaggagac aatatggaga ccgatacaat gtgagcggcc gcaataaaag    4800
atctttattt tcattagatc tgtgtgttgg ttttttgtgt gtctagagca tggctacgta    4860
gataagtagc atggcgggtt aatcattaac tacaaggaac ccctagtgat ggagttggcc    4920
actccctctc tgcgcgctcg ctcgctcact gaggccgggc gaccaaaggt cgcccgacgc    4980
ccgggctttg cccgggcggc ctcagtgagc gagcgagcgc gccagctggc gtaatagcga    5040
agaggcccgc accgatcgcc cttcccaaca gttgcgcagc ctgaatggcg aatggaagtt    5100
ccagacgatt gagcgtcaaa atgtaggtat tccatgagc gttttccctg ttgcaatggc    5160
tggcggtaat attgttctgg atattaccag caaggccgat agtttgagtt cttctactca    5220
ggcaagtgat gttattacta atcaaagaag tattgcgaca acggttaatt gcgtgatgg    5280 acagactctt ttactcggtg gcctcactga ttataaaaac acttctcagg attctggcgt    5340
accgttcctg tctaaaatcc ctttaatcgg cctcctgttt agctcccgct ctgattctaa    5400
cgaggaaagc acgttatacg tgctcgtcaa agcaaccata gtacgcgccc tgtagcggcg    5460
cattaagcgc ggcgggtgtg gtggttacgc gcagcgtgac cgctacactt gccagcgccc    5520
tagcgcccgc tcctttcgct ttcttccctt cctttctcgc cacgttcgcc ggctttcccc    5580
gtcaagctct aaatcggggg ctccctttag ggttccgatt tagtgattta cggcacctcg    5640
accccaaaaa acttgattag ggtgatggtt cacgtagtgg gccatcgccc tgatagacgg    5700 ttttcgccc tttgacgttg gagtccacgt tctttaatag tggactcttg ttccaaactg    5760
gaacaacact caaccctatc tcggtctatt cttttgattt ataagggatt ttgccgattt    5820
cggcctattg gttaaaaaat gagctgattt aacaaaaatt taacgcgaat tttaacaaaa    5880
tattaacgtt tacaatttaa atatttgctt atacaatctt cctgtttttg ggcttttct    5940 gattatcaac cggggtacat atgattgaca tgctagtttt acgattaccg ttcatcgatt    6000
ctcttgtttg ctccagactc tcaggcaatg acctgatagc ctttgtagag acctctcaaa    6060
aatagctacc ctctccggca tgaatttatc agctagaacg gttgaatatc atattgatgg    6120
tgatttgact gtctccggcc tttctcaccc gtttgaatct ttacctacac attactcagg    6180
cattgcattt aaaatatatg agggttctaa aaattttat ccttgcgttg aaataaaggc    6240
```

```
ttctcccgca aaagtattac agggtcataa tgttttggt acaaccgatt tagctttatg    6300
ctctgaggct ttattgctta attttgctaa ttctttgcct tgcctgtatg atttattgga    6360
tgttggaagt tcctgatgcg gtattttctc cttacgcatc tgtgcggtat ttcacaccgc    6420
atatggtgca ctctcagtac aatctgctct gatgccgcat agttaagcca gccccgacac    6480
ccgccaacac ccgctgacgc gccctgacgg gcttgtctgc tcccggcatc cgcttacaga    6540
caagctgtga ccgtctccgg gagctgcatg tgtcagaggt tttcaccgtc atcaccgaaa    6600
cgcgcgagac gaaagggcct cgtgatacgc ctatttttat aggttaatgt catgataata    6660
atggtttctt agacgtcagg tggcactttt cggggaaatg tgcgcggaac cctatttgt    6720 ttatttttct aaatacattc aaatatgtat ccgctcatga acaataaacc ctgataaatg    6780
cttcaataat attgaaaaag gaagagtatg agtattcaac atttccgtgt cgcccttatt    6840 ccctttttg cggcattttg ccttcctgtt tttgctcacc cagaaacgct ggtgaaagta    6900
aaagatgctg aagatcagtt gggtgcacga gtggttaca tcgaactgga tctcaacagc    6960
ggtaagatcc ttgagagttt tcgccccgaa gaacgttttc caatgatgag cacttttaaa    7020
gttctgctat gtggcgcggt attatcccgt attgacgccg ggcaagagca actcggtcgc    7080
cgcatacact attctcagaa tgacttggtt gagtactcac cagtcacaga aaagcatctt    7140
acggatggca tgacagtaag agaattatgc agtgctgcca taaccatgag tgataacact    7200
gcggccaact tacttctgac aacgatcgga ggaccgaagg agctaaccgc ttttttgcac    7260
aacatggggg atcatgtaac tcgccttgat cgttgggaac cggagctgaa tgaagccata    7320
ccaaacgacg agcgtgacac cacgatgcct gtagcaatgg caacaacgtt gcgcaaacta    7380
ttaactggcg aactacttac tctagcttcc cggcaacaat taatagactg gatggaggcg    7440
gataaagttg caggaccact tctgcgctcg gcccttccgg ctggctggtt tattgctgat    7500
aaatctggag ccggtgagcg tgggtctcgc ggtatcattg cagcactggg gccagatggt    7560
aagccctccc gtatcgtagt tatctacacg acggggagtc aggcaactat ggatgaacga    7620
aatagacaga tcgctgagat aggtgcctca ctgattaagc attggtaact gtcagaccaa    7680
gtttactcat atatacttta gattgattta aaacttcatt tttaatttaa aaggatctag    7740
gtgaagatcc ttttgataa tctcatgacc aaaatccctt aacgtgagtt ttcgttccac    7800
tgagcgtcag accccgtaga aaagatcaaa ggatcttctt gagatccttt ttttctgcgc    7860
gtaatctgct gcttgcaaac aaaaaaacca ccgctaccag cggtggtttg tttgccggat    7920
caagagctac caactctttt tccgaaggta actggcttca gcagagcgca gataccaaat    7980
actgtccttc tagtgtagcc gtagttaggc caccacttca agaactctgt agcaccgcgt    8040
acatacctcg ctctgctaat cctgttacca gtggctgctg ccagtggcga taagtcgtgt    8100
cttaccgggt tggactcaag acgatagtta ccggataagg cgcagcggtc gggctgaacg    8160
gggggttcgt gcacacagcc cagcttggag cgaacgacct acaccgaact gagataccta    8220
cagcgtgagc tatgagaaag cgccacgctt cccgaaggga gaaaggcgga caggtatccg    8280
gtaagcggca gggtcggaac aggagagcgc acgagggagc ttccaggggg aaacgcctgg    8340
tatctttata gtcctgtcgg gtttcgccac ctctgacttg agcgtcgatt tttgtgatgc    8400
tcgtcagggg ggcggagcct atggaaaaac gccagcaacg cggcctttt acggttcctg    8460 gccttttgct ggccttttgc tcacatgttc tttcctgcgt tatcccctga ttctgtggat    8520
aaccgtatta ccgggtttga gtgagctgat accgctcgcc gcagccgaac gaccgagcgc    8580
```
agcgagtcag tgagcgacca agcggaagag c                                    8611

<210> SEQ ID NO 4
<211> LENGTH: 564
<212> TYPE: DNA
<213> ORGANISM: Adeno-associated virus

<400> SEQUENCE: 4
cagccactat gggtctaggc tgcccatgta aggaggcaag gcctggggac acccgagatg      60
cctggttata attaacccag acatgtggct gctccccccc cccaacacct gctgcctgag     120
cctcaccccc accccggtgc ctgggtctta ggctctgtac accatggagg agaagctcgc     180
tctaaaaata accctgtccc tggtgggctg tggggactg agggcaggct gtaacaggct     240
tgggggccag ggcttatacg tgcctgggac tcccaaagta ttactgttcc atgttcccgg     300
cgaagggcca gctgtccccc gccagctaga ctcagcactt agtttaggaa ccagtgagca     360
agtcagccct ggggcagcc catacaaggc catgggctg gcaagctgc acgcctgggt     420 ccggggtggg cacggtgccc gggcaacgag ctgaaagctc atctgctctc aggggccccc     480
ccctggggac agcccctcct ggctagtcac accctgtagg ctcctctata taacccaggg     540 gcacagggc tgcccccggg tcac                                            564

<210> SEQ ID NO 5
<211> LENGTH: 8409
<212> TYPE: DNA
<213> ORGANISM: Adeno associated virus

<400> SEQUENCE: 5
gcccaatacg caaaccgcct ctccccgcgc gttggccgat tcattaatgc agctggcgcg      60
ctcgctcgct cactgaggcc gcccgggcaa agcccgggcg tcgggcgacc tttggtcgcc     120
cggcctcagt gagcgagcga gcgcgcagag agggagtggc caactccatc actaggggtt     180
ccttgtagtt aatgattaac cgccatgct aattatctac gtagccatgt ctagacagcc     240
actatgggtc taggctgccc atgtaaggag gcaaggcctg ggacacccg agatgcctgg     300 ttataattaa cccagacatg tggctgctcc cccccccaa cacctgctgc ctgagcctca     360
ccccaccccc ggtgcctggg tcttaggctc tgtacaccat ggaggagaag ctcgctctaa     420
aaataaccct gtccctggtg ggctgtgggg gactgagggc aggctgtaac aggcttgggg     480
gccagggctt atacgtgcct gggactccca agtattact gttccatgtt cccggcgaag     540
ggccagctgt cccccgccag ctagactcag cacttagttt aggaaccagt gagcaagtca     600
gcccttgggg cagcccatac aaggccatgg ggctgggcaa gctgcacgcc tgggtccggg     660
gtgggcacgg tgcccgggca acgagctgaa agctcatctg ctctcagggg ccctccctg     720 ggacagcccc tcctggcta gtcacaccct gtaggctcct ctataaacc caggggcaca     780 ggggctgccc ccgggtcacc accacctcca cagcacagac agacactcag gagccagcca     840
gccaggtaag tttagtcttt ttgtcttta tttcaggtcc cggatccgt ggtggtgcaa     900 atcaaagaac tgctcctcag tggatgttgc ctttacttct aggcctgtac ggaagtgtta     960
cttctgctct aaaagctgcg gaattgtacc cgcggccgcc accatgctgt ggtgggagga    1020
ggtggaggat tgttatgaaa gggaggacgt gcagaagaag acttttacca agtgggtgaa    1080
cgctcagttc agcaaatttg gaagcagca catcgagaat ctgtttttccg acctgcagga    1140 tgggagacgc ctgctggatc tgctggaagg actgactggc cagaagctgc ccaaagaaga    1200
ggggagcact agggtgcacg ccctgaacaa cgtgaacaaa gctctgagag tgctgcagaa    1260

```
caacaacgtg gatctggtga atattggcag tactgatatc gtggacggga accacaaact   1320
gacactgggc ctgatctgga acattattct gcactggcag gtgaaaaatg tgatgaagaa   1380
catcatggcc gggctgcagc agaccaattc cgagaagatc ctgctgtctt gggtgcggca   1440
gagcacccgc aactatcccc aggtgaacgt gattaacttc actacatcct ggagcgacgg   1500
gctggccctg aatgctctga ttcacagcca caggcctgat ctgttcgact ggaatagcgt   1560
ggtgtgccag cagtctgcca cacagcgcct ggaacatgcc ttcaatatcg ctcggtacca   1620
gctggggatc gaaaaactgc tggacccaga ggatgtggac actacatacc cagataaaaa   1680
gtctattctg atgtacatta ctagcctgtt ccaggtgctg ccacagcagg tgtctattga   1740
agccattcag gaggtggaaa tgctgccccg ccccccaaa gtgactaaag aggagcattt   1800
tcagctgcat catcagatgc attacagcca gcagattacc gtgagcctgg ctcagggata   1860
tgagcgcacc agtagtccaa aaccacggtt caagtcctac gcttataccc aggctgccta   1920
cgtgacaact agcgacccta ctagatcccc ctttccatcc cagcacctgg aggcccccaga   1980 ggacaagagc tttgggtcca gcctgatgga aagcgaggtg aatctggatc ggtaccagac   2040
agccctggag gaggtgctga gctggctgct gagtgctgaa gacacactgc aggcccaggg   2100
cgaaatttcc aatgacgtgg aagtggtgaa ggatcagttc cacacacacg agggctatat   2160
gatggacctg acagctcacc aggggcgcgt gggcaatatc ctgcagctgg gctctaaact   2220
gatcggcacc gggaaactga gtgaggacga ggaaacagaa gtgcaggagc agatgaacct   2280
gctgaacagc cgctgggagt gtctgagagt ggctagtatg gagaagcagt ccaacctgca   2340
ccgggtgctg atggacctgc agaaccagaa actgaaagag ctgaacgact ggctgacaaa   2400
gactgaggaa cgcacaagga agatggagga ggagccactg gacccgacc tggaggatct   2460 gaagagacag gtgcagcagc ataaggtgct gcaggaggat ctggaacagg agcaggtgcg   2520
ggtgaactcc ctgacacata tggtggtggt ggtggacgaa tctagtggag atcacgccac   2580
cgccgccctg gaggaacagc tgaaggtgct gggggaccgg tgggccaaca tttgccggtg   2640
gaccgaggac aggtgggtgc tgctgcagga catcctgctg aaatggcaga ggctgaccga   2700
ggagcagtgt ctgtttagtg cttggctgag cgagaaaagg gacgccgtga acaagatcca   2760
cacaaccggc tttaaggatc agaacgaaat gctgtctagc ctgcagaaac tggctgtgct   2820
gaaggccgat ctggagaaaa agaagcagag catgggcaaa ctgtatagcc tgaaacagga   2880
cctgctgagc accctgaaga caagagcgt gacccagaag acagaagcct ggctggataa   2940
ctttgcccgc tgctgggaca acctggtgca gaaactggaa aaagtacag ctcagatctc   3000 tcaggctgtg accacaaccc agcctagcct gacccagaca accgtgatgg aaaccgtgac   3060
caccgtgaca cccgcgaac agatcctggt gaaacatgcc caggaagagc tgccacctcc   3120
acctccccag aagaagagaa ccctggagcg gctgcaggag ctgcaggaag ccactgacga   3180
actgaccctg aagctgaggc aggccgaagt gattaagggg tcttggcagc ctgtgggcga   3240
tctgctgatt gattccctgc aggaccacct ggaaaaggtg aaggctctga gaggcgaaat   3300
tgctccactg aaggagaacg tgagtcatgt gaacgatctg ctagacagc tgacaacact   3360 gggcatccag ctgagcccat acaatctgag cacactggag gacctgaata ccaggtggaa   3420
gctgctgcag gtggctgtgg aagacgggt gcggcagctg catgaggccc atcgcgactt   3480
cggaccagcc agccagcact ttctgagcac atccgtgcag gggccctggg agagggccat   3540
ttctcccaac aaggtgccct actatattaa tcacgagacc cagaccactt gttgggacca   3600
```

```
tcccaagatg acagaactgt accagtccct ggccgatctg aacaacgtga ggtttagcgc    3660
ttacagaacc gctatgaagc tgagacggct gcagaaggcc ctgtgcctgg atctgctgtc    3720
cctgtccgcc gcctgcgatg ccctggatca gcataatctg aagcagaacg atcagccaat    3780
ggatatcctg cagatcatca actgcctgac cactatctac gacaggctgg agcaggagca    3840
caacaacctg gtgaacgtgc ctctgtgcgt ggatatgtgc ctgaactggc tgctgaacgt    3900
gtatgacact gggcgcaccg gccggatcag agtgctgagt tttaaaactg ggattatctc    3960
cctgtgtaag gcccacctgg aggacaagta caggtacctg ttcaagcagg tggctagtag    4020
cactggattt tgtgaccagc gccgcctggg actgctgctg catgatagta tccagattcc    4080
tagacagctg ggagaggtgg ctagtttcgg aggatctaac atcgaaccca gcgtgcgcag    4140
ctgtttccag tttgccaata caaaacctga atcgaggct gctctgttcc tggattggat    4200
gcgcctggaa ccacagagca tggtgtggct gcctgtgctg cacagagtgg ctgccgccga    4260
aactgccaag caccaggcta aatgcaacat ctgcaaggaa tgtcccatta tcggctttcg    4320
ctacaggagt ctgaaacatt ttaactacga tatttgccag agctgcttct tttccggaag    4380
agtggccaaa ggacacaaga tgcactaccc tatggtggaa tattgcaccc caactacatc    4440
tggcgaagat gtgcgcgatt ttgccaaggt gctgaagaat aagtttcgga ctaagaggta    4500
cttcgccaag caccccccgca tggggtatct gccagtgcag acagtgctgg aaggagacaa    4560 tatgcgagacc gatacaatgt gagcggccgc aataaaagat ctttattttc attagatctg    4620
tgtgttggtt ttttgtgtgt ctagagcatg gctacgtaga taagtagcat ggcgggttaa    4680
tcattaacta caaggaaccc ctagtgatgg agttggccac tccctctctg cgcgctcgct    4740
cgctcactga ggccgggcga ccaaaggtcg cccgacgccc gggctttgcc cgggcggcct    4800
cagtgagcga gcgagcgcgc agctggcgt aatagcgaag aggcccgcac cgatcgccct    4860
tcccaacagt tgcgcagcct gaatggcgaa tggaagttcc agacgattga gcgtcaaaat    4920
gtaggtattt ccatgagcgt ttttcctgtt gcaatggctg gcggtaatat tgttctggat    4980
attaccagca aggccgatag tttgagttct tctactcagg caagtgatgt tattactaat    5040
caaagaagta ttgcgacaac ggttaatttg cgtgatggac agactctttt actcggtggc    5100
ctcactgatt ataaaaacac ttctcaggat tctggcgtac cgttcctgtc taaaatccct    5160
ttaatcggcc tcctgtttag ctcccgctct gattctaacg aggaaagcac gttatacgtg    5220
ctcgtcaaag caaccatagt acgcgccctg tagcggcgca ttaagcgcgg cgggtgtggt    5280
ggttacgcgc agcgtgaccg ctacacttgc cagcgcccta gcgcccgctc ctttcgcttt    5340
cttcccttcc tttctcgcca cgttcgccgg ctttccccgt caagctctaa atcggggct    5400 ccctttaggg ttccgattta gtgatttacg gcacctcgac cccaaaaaac ttgattaggg    5460
tgatggttca cgtagtgggc catcgccctg atagacggtt tttcgccctt tgacgttgga    5520
gtccacgttc tttaatagtg gactcttgtt ccaaactgga acaacactca accctatctc    5580
ggtctattct tttgatttat aagggatttt gccgatttcg gcctattggt taaaaaatga    5640
gctgatttaa caaaaattta acgcgaattt taacaaaata ttaacgttta catttaaaat    5700
atttgcttat acaatcttcc tgttttgggg ctttttctga ttatcaaccg ggtacatat    5760 gattgacatg ctagttttac gattaccgtt catcgattct cttgtttgct ccagactctc    5820
aggcaatgac ctgatagcct ttgtagagac ctctcaaaaa tagctaccct ctccggcatg    5880
aatttatcag ctagaacggt tgaatatcat attgatggtg atttgactgt ctccggcctt    5940
tctcacccgt ttgaatcttt acctacacat tactcaggca ttgcatttaa aatatatgag    6000
```

```
ggttctaaaa attttatcc ttgcgttgaa ataaaggctt ctcccgcaaa agtattacag    6060
ggtcataatg tttttggtac aaccgattta gctttatgct ctgaggcttt attgcttaat    6120
tttgctaatt ctttgccttg cctgtatgat ttattggatg ttggaagttc ctgatgcggt    6180
atttctcct tacgcatctg tgcggtattt cacaccgcat atggtgcact ctcagtacaa     6240
tctgctctga tgccgcatag ttaagccagc cccgacaccc gccaacaccc gctgacgcgc    6300
cctgacgggc ttgtctgctc ccggcatccg cttacagaca agctgtgacc gtctccggga    6360
gctgcatgtg tcagaggttt tcaccgtcat caccgaaacg cgcgagacga aagggcctcg    6420
tgatacgcct attttatag gttaatgtca tgataataat ggtttcttag acgtcaggtg    6480
gcacttttcg gggaaatgtg cgcggaaccc ctatttgttt attttctaa atacattcaa     6540
atatgtatcc gctcatgaga caataaccct gataaatgct tcaataatat tgaaaaagga    6600
agagtatgag tattcaacat ttccgtgtcg cccttattcc cttttttgcg cattttgcc     6660
ttcctgtttt tgctcaccca gaaacgctgg tgaaagtaaa agatgctgaa gatcagttgg    6720
gtgcacgagt gggttacatc gaactggatc tcaacagcgg taagatcctt gagagttttc    6780
gccccgaaga acgttttcca atgatgagca cttttaaagt tctgctatgt ggcgcggtat    6840
tatcccgtat tgacgccggg caagagcaac tcggtcgccg catacactat tctcagaatg    6900
acttggttga gtactcacca gtcacagaaa agcatcttac ggatggcatg acagtaagag    6960
aattatgcag tgctgccata accatgagtg ataacactgc ggccaactta cttctgacaa    7020
cgatcggagg accgaaggag ctaaccgctt ttttgcacaa catgggggat catgtaactc    7080
gccttgatcg ttgggaaccg gagctgaatg aagccatacc aaacgacgag cgtgacacca    7140
cgatgcctgt agcaatggca acaacgttgc gcaaactatt aactggcgaa ctacttactc    7200
tagcttcccg gcaacaatta atagactgga tggaggcgga taaagttgca ggaccacttc    7260
tgcgctcggc ccttccggct ggctggttta ttgctgataa atctggagcc ggtgagcgtg    7320
ggtctcgcgg tatcattgca gcactggggc cagatggtaa gccctcccgt atcgtagtta    7380
tctacacgac ggggagtcag gcaactatgg atgaacgaaa tagacagatc gctgagatag    7440
gtgcctcact gattaagcat tggtaactgt cagaccaagt ttactcatat atactttaga    7500
ttgatttaaa acttcatttt taatttaaaa ggatctaggt gaagatcctt tttgataatc    7560
tcatgaccaa aatcccttaa cgtgagtttt cgttccactg agcgtcagac cccgtagaaa    7620
agatcaaagg atcttcttga gatccttttt ttctgcgcgt aatctgctgc ttgcaaacaa    7680
aaaaaccacc gctaccagcg gtggtttgtt tgccggatca agagctacca actctttttc    7740
cgaaggtaac tggcttcagc agagcgcaga taccaaatac tgtccttcta gtgtagccgt    7800
agttaggcca ccacttcaag aactctgtag caccgcgtac atacctcgct ctgctaatcc    7860
tgttaccagt ggctgctgcc agtggcgata agtcgtgtct taccgggttg gactcaagac    7920
gatagttacc ggataaggcg cagcggtcgg gctgaacggg gggttcgtgc acacagccca    7980
gcttggagcg aacgacctac accgaactga gatacctaca gcgtgagcta tgagaaagcg    8040
ccacgcttcc cgaagggaga aaggcggaca ggtatccggt aagcggcagg gtcggaacag    8100
gagagcgcac gagggagctt ccagggggaa acgcctggta tctttatagt cctgtcgggt    8160
ttcgccacct ctgacttgag cgtcgatttt tgtgatgctc gtcaggggg cggagcctat     8220
ggaaaaacgc cagcaacgcg gcctttttac ggttcctggc cttttgctgg ccttttgctc    8280
acatgttctt tcctgcgtta tcccctgatt ctgtggataa ccgtattacc gggtttgagt    8340
```

<210> SEQ ID NO 6
<211> LENGTH: 5910
<212> TYPE: DNA
<213> ORGANISM: Adeno-associated virus
<220> FEATURE:
<221> NAME/KEY: promoter
<222> LOCATION: (120)..(526)
<223> OTHER INFORMATION: CMV promotor
<220> FEATURE:
<221> NAME/KEY: Intron
<222> LOCATION: (927)..(1087)
<223> OTHER INFORMATION: EF1a intron
<220> FEATURE:
<221> NAME/KEY: misc_feature
<222> LOCATION: (1088)..(1375)
<223> OTHER INFORMATION: shRNA-miR29-c
<220> FEATURE:
<221> NAME/KEY: misc_feature
<222> LOCATION: (1257)..(1284)
<223> OTHER INFORMATION: miR-29c
<220> FEATURE:
<221> NAME/KEY: Intron
<222> LOCATION: (1380)..(1854)
<223> OTHER INFORMATION: EF1a intron
<220> FEATURE:
<221> NAME/KEY: misc_feature
<222> LOCATION: (1896)..(2091)
<223> OTHER INFORMATION: polyA

<400> SEQUENCE: 6

```
gagctgatac cgctcgccgc agccgaacga ccgagcgcag cgagtcagtg agcgaccaag      8400
cggaagagc                                                              8409 cagcagctgc gcgctcgctc gctcactgag gccgcccggg caaagcccgg gcgtcgggcg        60
acctttggtc gcccggcctc agtgagcgag cgagcgcgca gagagggagt ggggttaaac       120
tcgttacata acttacggta aatggcccgc ctggctgacc gcccaacgac ccccgcccat       180
tgacgtcaat aatgacgtat gttcccatag taacgccaat agggactttc cattgacgtc       240
aatgggtgga gtatttacgg taaactgccc acttggcagt acatcaagtg tatcatatgc       300
caagtacgcc ccctattgac gtcaatgacg gtaaatggcc cgcctggcat tatgcccagt       360
acatgacctt atgggacttt cctacttggc agtacatcta cgtattagtc atcgctatta       420
ccatggtgat gcggttttgg cagtacatca atgggcgtgg atagcggttt gactcacggg       480
gatttccaag tctccacccc attgacgtca atggagtttg ttttggcac caaaatcaac       540
gggactttcc aaaatgtcgt aacaactccg ccccattgac gcaaatgggc ggtaggcgtg       600
tacggtggga ggtctatata agcagagctc gtttagtgaa ccgtcagatc gcctggagac       660
gccatccacg ctgttttgac ctccatagaa gacaccggga ccgatccagc ctccggactc       720
tagaggatcc ggtactcgag gaactgaaaa accagaaagt taactggtaa gtttagtctt       780
tttgtctttt atttcaggtc ccggatccgg tggtggtgca aatcaaagaa ctgctcctca       840
gtggatgttg cctttacttc taggcctgta cggaagtgtt acttctgctc taaaagctgc       900
ggaattgtac ccggggccga tccaccggtc tttttcgcaa cgggtttgcc gccagaacac       960
aggtaagtgc cgtgtgtggt tcccgcgggc ggcgacgggg cccgtgcgtc ccagcgcaca      1020
tgttcggcga ggcggggcct gcgagcgcgg ccaccgagaa tcggacgggg gtagtctcaa      1080
gctggccggc ctgtttgaat gaggcttcag tactttacag aatcgttgcc tgcacatctt      1140
ggaaacactt gctgggatta cttcttcagg ttaacccaac agaaggctcg agaaggtata      1200
ttgctgttga cagtgagcgc aaccgatttc aaatggtgct agagtgaagc cacagatgtc      1260
tagcaccatt tgaaatcggt tatgcctact gcctcggaat tcaaggggct actttaggag      1320
```

```
caattatctt gtttactaaa actgaatacc ttgctatctc tttgatacat tggccggcct    1380
gctctggtgc ctggcctcgc gccgccgtgt atcgccccgc cctgggcggc aaggctggcc    1440
cggtcggcac cagttgcgtg agcggaaaga tggccgcttc ccggccctgc tgcagggagc    1500
tcaaaatgga ggacgcggcg ctcggagag cgggcgggtg agtcacccac acaaaggaaa    1560
agggcctttc cgtcctcagc cgtcgcttca tgtgactcca cggagtaccg ggcgccgtcc    1620
aggcacctcg attagttctc gagcttttgg agtacgtcgt ctttaggttg ggggagggg    1680 ttttatgcga tggagtttcc ccacactgag tgggtggaga ctgaagttag gccagcttgg    1740
cacttgatgt aattctcctt ggaatttgcc ctttttgagt ttggatcttg gttcattctc    1800
aagcctcaga cagtggttca aagtttttt cttccatttc aggtgtcgtg aaaagctagc    1860
gctaccggac tcagatctcg agctcaagct gcggggatcc agacatgata agatacattg    1920
atgagtttgg acaaccaca actagaatgc agtgaaaaaa atgctttatt tgtgaaattt    1980
gtgatgctat tgctttattt gtaaccatta taagctgcaa taaacaagtt aacaacaaca    2040
attgcattca ttttatgttt caggttcagg gggaggtgtg ggaggttttt tcactagtag    2100
catggctacg tagataagta gcatggcggg ttaatcatta actacaagga accctagtg     2160 atggagttgg ccactccctc tctgcgcgct cgctcgctca ctgaggccgg gcgaccaaag    2220
gtcgcccgac gcccgggctt tgcccggcg gcctcagtga gcgagcgagc gcgccagctg    2280
gcgtaatagc gaagaggccc gcaccgatcg cccttcccaa cagttgcgca gcctgaatgg    2340
cgaatggaat tccagacgat tgagcgtcaa aatgtaggta tttccatgag cgttttcct    2400 gttgcaatgg ctggcggtaa tattgttctg gatattacca gcaaggccga tagtttgagt    2460
tcttctactc aggcaagtga tgttattact aatcaaagaa gtattgcgac aacggttaat    2520
ttgcgtgatg gacagactct tttactcggt ggcctcactg attataaaaa cacttctcag    2580
gattctggcg taccgttcct gtctaaaatc cctttaatcg gcctcctgtt tagctcccgc    2640
tctgattcta acgaggaaag cacgttatac gtgctcgtca aagcaaccat agtacgcgcc    2700
ctgtagcggc gcattaagcg cggcgggtgt ggtggttacg cgcagcgtga ccgctacact    2760
tgccagcgcc ctagcgcccg ctcctttcgc tttcttccct tcctttctcg ccacgttcgc    2820
cggctttccc cgtcaagctc taaatcgggg ctcccttta gggttccgat ttagtgcttt    2880
acggcacctc gaccccaaaa aacttgatta gggtgatggt tcacgtagtg gccatcgcc     2940 ctgatagacg ttttcgcc ctttgacgtt ggagtccacg ttctttaata gtggactctt    3000
gttccaaact ggaacaacac tcaaccctat ctcggtctat tcttttgatt tataagggat    3060
tttgccgatt tcggcctatt ggttaaaaaa tgagctgatt taacaaaaat ttaacgcgaa    3120
ttttaacaaa atattaacgt ttacaattta aatatttgct tatacaatct tcctgttttt    3180
ggggcttttc tgattatcaa ccggggtaca tatgattgac atgctagttt tacgattacc    3240
gttcatcgat tctcttgttt gctccagact ctcaggcaat gacctgatag cctttgtaga    3300
gacctctcaa aaatagctac cctctccggc atgaatttat cagctagaac ggttgaatat    3360
catattgatg gtgatttgac tgtctccggc ctttctcacc cgtttgaatc tttacctaca    3420
cattactcag gcattgcatt taaaatatat gagggttcta aaaatttta tccttgcgtt    3480 gaaataaagg cttctcccgc aaaagtatta cagggtcata atgtttttgg tacaaccgat    3540
ttagctttat gctctgaggc tttattgctt aattttgcta attctttgcc ttgcctgtat    3600
gatttattgg atgttggaat tcctgatgcg gtattttctc cttacgcatc tgtgcggtat    3660
```

-continued

```
ttcacaccgc atatggtgca ctctcagtac aatctgctct gatgccgcat agttaagcca      3720
gccccgacac ccgccaacac ccgctgacgc gccctgacgg gcttgtctgc tcccggcatc      3780
cgcttacaga caagctgtga ccgtctccgg gagctgcatg tgtcagaggt tttcaccgtc      3840
atcaccgaaa cgcgcgagac gaaagggcct cgtgatacgc ctattttttat aggttaatgt     3900
catgataata atggtttctt agacgtcagg tggcactttt cggggaaatg tgcgcggaac      3960
ccctatttgt ttattttttct aaatacattc aaatatgtat ccgctcatga gacaataacc    4020
ctgataaatg cttcaataat attgaaaaag gaagagtatg agtattcaac atttccgtgt     4080
cgccctattt ccctttttg cggcattttg ccttcctgtt tttgctcacc cagaaacgct      4140
ggtgaaagta aaagatgctg aagatcagtt gggtgcacga gtgggttaca tcgaactgga     4200
tctcaacagc ggtaagatcc ttgagagttt tcgccccgaa gaacgttttc caatgatgag     4260
cacttttaaa gttctgctat gtggcgcggt attatcccgt attgacgccg gcaagagca      4320
actcggtcgc cgcatacact attctcagaa tgacttggtt gagtactcac cagtcacaga     4380
aaagcatctt acggatggca tgacagtaag agaattatgc agtgctgcca taaccatgag     4440
tgataacact gcggccaact tacttctgac aacgatcgga ggaccgaagg agctaaccgc     4500
tttttttgcac aacatggggg atcatgtaac tcgccttgat cgttgggaac cggagctgaa    4560
tgaagccata ccaaacgacg agcgtgacac cacgatgcct gtagcaatgg caacaacgtt    4620
gcgcaaacta ttaactggcg aactacttac tctagcttcc cggcaacaat taatagactg    4680
gatggaggcg gataaagttg caggaccact tctgcgctcg gcccttccgg ctggctggtt    4740
tattgctgat aaatctggag ccggtgagcg tgggtctcgc ggtatcattg cagcactggg    4800
gccagatggt aagccctccc gtatcgtagt tatctacacg acggggagtc aggcaactat    4860
ggatgaacga aatagacaga tcgctgagat aggtgcctca ctgattaagc attggtaact    4920
gtcagaccaa gtttactcat atatacttta gattgattta aaacttcatt tttaatttaa    4980
aaggatctag gtgaagatcc ttttttgataa tctcatgacc aaaatccctt aacgtgagtt    5040
ttcgttccac tgagcgtcag accccgtaga aaagatcaaa ggatcttctt gagatccttt    5100
ttttctgcgc gtaatctgct gcttgcaaac aaaaaaacca ccgctaccag cggtggtttg    5160
tttgccggat caagagctac caactctttt tccgaaggta actggcttca gcagagcgca    5220
gataccaaat actgtccttc tagtgtagcc gtagttaggc caccacttca agaactctgt    5280
agcaccgcct acatacctcg ctctgctaat cctgttacca gtggctgctg ccagtggcga    5340
taagtcgtgt cttaccgggt tggactcaag acgatagtta ccggataagg cgcagcggtc    5400
gggctgaacg gggggttcgt gcacacagcc cagcttggag cgaacgacct acaccgaact    5460
gagataccta cagcgtgagc tatgagaaag cgccacgctt cccgaaggga gaaaggcgga    5520
caggtatccg gtaagcggca gggtcggaac aggagagcgc acgagggagc ttccaggggg    5580
aaacgcctgg tatctttata gtcctgtcgg gtttcgccac ctctgacttg agcgtcgatt    5640
tttgtgatgc tcgtcagggg ggcggagcct atggaaaaac gccagcaacg cggccttttt    5700
acggttcctg gccttttgct ggccttttgc tcacatgttc tttcctgcgt tatcccctga    5760
ttctgtggat aaccgtatta ccgcctttga gtgagctgat accgctcgcc gcagccgaac    5820
gaccgagcgc agcgagtcag tgagcgagga agcggaagag cgcccaatac gcaaaccgcc    5880
tctccccgcg cgttggccga ttcattaatg                                      5910
```

<210> SEQ ID NO 7
<211> LENGTH: 296

<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(8)
<223> OTHER INFORMATION: FSE-I cut site
<220> FEATURE:
<221> NAME/KEY: misc_feature
<222> LOCATION: (9)..(136)
<223> OTHER INFORMATION: miR-30 backbone
<220> FEATURE:
<221> NAME/KEY: misc_feature
<222> LOCATION: (139)..(160)
<223> OTHER INFORMATION: miR-29c target (sense) strand
<220> FEATURE:
<221> NAME/KEY: misc_feature
<222> LOCATION: (161)..(175)
<223> OTHER INFORMATION: miR-29c target (sense) strand
<220> FEATURE:
<221> NAME/KEY: misc_feature
<222> LOCATION: (176)..(199)
<223> OTHER INFORMATION: miR-30 stem loop
<220> FEATURE:
<221> NAME/KEY: misc_feature
<222> LOCATION: (200)..(288)
<223> OTHER INFORMATION: miR-29c guide (antisense) strand
<220> FEATURE:
<221> NAME/KEY: misc_feature
<222> LOCATION: (289)..(296)
<223> OTHER INFORMATION: miR-30 backbone

<400> SEQUENCE: 7
ggccggcctg tttgaatgag gcttcagtac tttacagaat cgttgcctgc acatcttgga      60
aacacttgct gggattactt cttcaggtta acccaacaga aggctcgaga aggtatattg     120
ctgttgacag tgagcgcaac cgatttcaaa tggtgctaga gtgaagccac agatgtctag     180
caccatttga aatcggttat gcctactgcc tcggaattca aggggctact ttaggagcaa     240
ttatcttgtt tactaaaact gaataccttg ctatctcttt gatacattgg ccggcc         296

<210> SEQ ID NO 8
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 8
accgatttca aatggtgcta ga                                               22

<210> SEQ ID NO 9
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 9
tctagcacca tttgaaatcg gtta                                             24

<210> SEQ ID NO 10
<211> LENGTH: 407
<212> TYPE: DNA
<213> ORGANISM: Artificial Sequence
<220> FEATURE:
<223> OTHER INFORMATION: CMV promotor

<400> SEQUENCE: 10

-continued

```
ctcgttacat aacttacggt aaatggcccg cctggctgac cgcccaacga cccccgccca        60
ttgacgtcaa taatgacgta tgttcccata gtaacgccaa tagggacttt ccattgacgt       120
caatgggtgg agtatttacg gtaaactgcc cacttggcag tacatcaagt gtatcatatg       180
ccaagtacgc ccoctattga cgtcaatgac ggtaaatggc ccgcctggca ttatgcccag       240
tacatgacct tatgggactt tcctacttgg cagtacatct acgtattagt catcgctatt       300
accatggtga tgcggttttg gcagtacatc aatgggcgtg gatagcggtt tgactcacgg       360
ggatttccaa gtctccaccc cattgacgtc aatgggagtt tgttttg                    407
```